(12) United States Patent
Leong et al.

(10) Patent No.: US 10,975,114 B2
(45) Date of Patent: Apr. 13, 2021

(54) BIS 2'-5'-RR-(3'F-A)(3'F-A) CYCLIC DINUCLEOTIDE COMPOUND AND USES THEREOF

(71) Applicants: ADURO BIOTECH, INC., Berkeley, CA (US); NOVARTIS AG, Basel (CH)

(72) Inventors: Justin Leong, Union City, CA (US); Chudi Obioma Ndubaku, Oakland, CA (US); Jeffrey McKenna, Carlisle, MA (US)

(73) Assignees: CHINOOK THERAPEUTICS, INC., Seattle, WA (US); NOVARTIS AG, Basel (CH)

( * ) Notice: Subject to any disclaimer, the term of this patent is extended or adjusted under 35 U.S.C. 154(b) by 0 days.

(21) Appl. No.: 16/609,126

(22) PCT Filed: Apr. 26, 2018

(86) PCT No.: PCT/IB2018/052918
§ 371 (c)(1),
(2) Date: Oct. 28, 2019

(87) PCT Pub. No.: WO2018/198076
PCT Pub. Date: Nov. 1, 2018

(65) Prior Publication Data
US 2020/0199169 A1 Jun. 25, 2020

Related U.S. Application Data

(60) Provisional application No. 62/491,879, filed on Apr. 28, 2017, provisional application No. 62/578,172, filed on Oct. 27, 2017.

(51) Int. Cl.
| | | |
|---|---|---|
| *A01N 43/04* | (2006.01) | |
| *A61K 31/70* | (2006.01) | |
| *C07H 21/04* | (2006.01) | |
| *A61P 35/04* | (2006.01) | |
| *A61K 39/00* | (2006.01) | |
| *A61K 39/39* | (2006.01) | |
| *A61K 45/06* | (2006.01) | |

(52) U.S. Cl.
CPC .......... *C07H 21/04* (2013.01); *A61K 39/0011* (2013.01); *A61K 39/39* (2013.01); *A61P 35/04* (2018.01); *A61K 45/06* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 4,978,672 | A | 12/1990 | Bowman et al. |
| 5,637,483 | A | 6/1997 | Dranoff et al. |
| 5,698,432 | A | 12/1997 | Oxford |
| 5,811,097 | A | 9/1998 | Allison et al. |
| 5,904,920 | A | 5/1999 | Dranoff et al. |
| 5,985,290 | A | 11/1999 | Jaffee et al. |
| 6,033,674 | A | 3/2000 | Jaffee et al. |
| 6,111,090 | A | 8/2000 | Gorman et al. |
| 6,277,368 | B1 | 8/2001 | Hiserodt et al. |
| 6,350,445 | B1 | 2/2002 | Jaffee et al. |
| 6,464,973 | B1 | 10/2002 | Levitsky et al. |
| 6,689,607 | B2 | 2/2004 | Ni et al. |
| 7,025,962 | B1 | 4/2006 | Gorman et al. |
| 7,169,791 | B2 | 1/2007 | Breitenstein et al. |
| 7,473,761 | B2 | 1/2009 | Albert et al. |
| 7,482,367 | B2 | 1/2009 | Aikawa et al. |
| 7,592,326 | B2 | 9/2009 | Karaolis |
| 7,598,257 | B2 | 10/2009 | Rodgers et al. |
| 7,618,632 | B2 | 11/2009 | Collins et al. |
| 7,709,458 | B2 | 5/2010 | Karaolis et al. |
| 7,767,675 | B2 | 8/2010 | Zhuo et al. |
| 7,812,135 | B2 | 10/2010 | Smith et al. |
| 7,867,493 | B2 | 1/2011 | Damiano et al. |
| 7,943,743 | B2 | 5/2011 | Korman et al. |
| 8,008,449 | B2 | 8/2011 | Korman et al. |
| 8,012,469 | B2 | 9/2011 | Levitsky et al. |
| 8,039,479 | B2 | 10/2011 | Michellys et al. |
| 8,354,509 | B2 | 1/2013 | Carven |
| 8,372,858 | B2 | 2/2013 | Michellys et al. |
| 8,388,967 | B2 | 3/2013 | Smith et al. |
| 8,415,355 | B2 | 4/2013 | Besong et al. |
| 8,420,645 | B2 | 4/2013 | Weng et al. |
| 8,519,129 | B2 | 8/2013 | Marsilje, III et al. |
| 8,546,336 | B2 | 10/2013 | Chen et al. |
| 8,552,002 | B2 | 10/2013 | Ding et al. |
| 8,552,003 | B2 | 10/2013 | Chen et al. |

(Continued)

FOREIGN PATENT DOCUMENTS

| | | |
|---|---|---|
| EP | 0296122 A2 | 12/1988 |
| EP | 1441737 A1 | 8/2004 |

(Continued)

OTHER PUBLICATIONS

Ablasser et al., cGAS produces 2'-5'-linked cdn second messenger that activates STING. Nature. Jun. 20, 2013;498(7454):380-384.

Amman et al., A Simple Multinuclear NMR Thermometer. J Magn Reson. 1982;46(2):319-321.

Aslanidis and de Jong, Ligation-independent cloning of PCR products (LIC-PCR). Nucleic Acids Res. Oct. 25, 1990;18(20):6069-6074.

(Continued)

*Primary Examiner* — Patrick T Lewis
(74) *Attorney, Agent, or Firm* — Acuity Law Group, PC; Michael A. Whittaker

(57) ABSTRACT

The present invention provides the cyclic dinucleotide compound 2'2'-RR-(3'F-A)(3'F-A) as a highly active immune stimulator that activates DCs via the cytoplasmic receptor known as STING (Stimulator of Interferon Genes), and compositions and uses thereof.

17 Claims, 7 Drawing Sheets
Specification includes a Sequence Listing.

(56) References Cited

U.S. PATENT DOCUMENTS

| | | | |
|---|---|---|---|
| 8,552,156 B2 | 10/2013 | Takayanagi et al. |
| 8,562,997 B2 | 10/2013 | Jaiswal et al. |
| 8,586,023 B2 | 11/2013 | Shiku et al. |
| 8,591,886 B2 | 11/2013 | Ponath et al. |
| 8,609,089 B2 | 12/2013 | Langermann et al. |
| 8,685,980 B2 | 4/2014 | Besong et al. |
| 8,709,424 B2 | 4/2014 | Schebye et al. |
| 8,728,476 B2 | 5/2014 | Van Den Berg |
| 8,735,551 B2 | 5/2014 | Garner et al. |
| 8,895,705 B2 | 11/2014 | Medema et al. |
| 2007/0142401 A1 | 6/2007 | Auberson et al. |
| 2010/0028330 A1 | 2/2010 | Collins et al. |
| 2010/0056576 A1 | 3/2010 | Burger et al. |
| 2010/0105667 A1 | 4/2010 | Furet et al. |
| 2010/0150946 A1 | 6/2010 | Jooss et al. |
| 2010/0310602 A1 | 12/2010 | Reed et al. |
| 2011/0150892 A1 | 6/2011 | Thudium et al. |
| 2012/0039906 A1 | 2/2012 | Olive |
| 2012/0114649 A1 | 5/2012 | Langermann et al. |
| 2012/0252785 A1 | 10/2012 | Griffin et al. |
| 2013/0225574 A1 | 8/2013 | Caravatti et al. |
| 2014/0044728 A1 | 2/2014 | Takayanagi et al. |
| 2014/0072566 A1 | 3/2014 | Kwon |
| 2014/0242095 A1 | 8/2014 | Wang et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2016/0108123 A1 | 4/2016 | Freeman et al. |

FOREIGN PATENT DOCUMENTS

| | | |
|---|---|---|
| EP | 1682103 A1 | 7/2006 |
| EP | 1870399 A1 | 12/2007 |
| EP | 0920505 B1 | 6/2008 |
| EP | 2099447 B1 | 11/2012 |
| EP | 2051990 B1 | 2/2013 |
| EP | 2581113 A1 | 4/2013 |
| EP | 1866339 B1 | 5/2013 |
| EP | 1947183 B1 | 7/2013 |
| EP | 2344474 B1 | 9/2015 |
| EP | 2474545 B1 | 11/2016 |
| EP | 2606070 B1 | 12/2016 |
| WO | 9749395 A1 | 12/1997 |
| WO | 9835958 A1 | 8/1998 |
| WO | 9903854 A1 | 1/1999 |
| WO | 9920758 A1 | 4/1999 |
| WO | 9940196 A1 | 8/1999 |
| WO | 0103720 A2 | 1/2001 |
| WO | 0210192 A2 | 2/2002 |
| WO | 0222577 A2 | 3/2002 |
| WO | 03037347 A1 | 5/2003 |
| WO | 03077914 A1 | 9/2003 |
| WO | 2004005281 A1 | 1/2004 |
| WO | 2004045532 A2 | 6/2004 |
| WO | 2004060319 A2 | 7/2004 |
| WO | 2004072051 A1 | 8/2004 |
| WO | 2005007190 A1 | 1/2005 |
| WO | 2005039549 A1 | 5/2005 |
| WO | 2005055808 A2 | 6/2005 |
| WO | 2005115451 A2 | 12/2005 |
| WO | 2006083289 A2 | 8/2006 |
| WO | 2006121168 A1 | 11/2006 |
| WO | 2006122806 A2 | 11/2006 |
| WO | 2007005874 A2 | 1/2007 |
| WO | 2007024945 A1 | 3/2007 |
| WO | 2007030377 A1 | 3/2007 |
| WO | 2007054279 A2 | 5/2007 |
| WO | 2007070514 A1 | 6/2007 |
| WO | 2007084786 A1 | 7/2007 |
| WO | 2007121484 A2 | 10/2007 |
| WO | 2007131201 A2 | 11/2007 |
| WO | 2007133822 A1 | 11/2007 |
| WO | 2008016893 A1 | 2/2008 |
| WO | 2008073687 A2 | 6/2008 |
| WO | 2008106692 A1 | 9/2008 |
| WO | 2009114335 A2 | 9/2009 |
| WO | 2009115562 A2 | 9/2009 |
| WO | 2009141386 A1 | 11/2009 |
| WO | 2010002655 A2 | 1/2010 |
| WO | 2010003118 A1 | 1/2010 |
| WO | 2010007120 A1 | 1/2010 |
| WO | 2010019570 A2 | 2/2010 |
| WO | 2010026124 A1 | 3/2010 |
| WO | 2010027827 A2 | 3/2010 |
| WO | 2010029082 A1 | 3/2010 |
| WO | 2010060937 A2 | 6/2010 |
| WO | 2010077634 A1 | 7/2010 |
| WO | 2010101849 A1 | 9/2010 |
| WO | 2010104833 A1 | 9/2010 |
| WO | 2010149755 A1 | 12/2010 |
| WO | 2011025927 A1 | 3/2011 |
| WO | 2011028683 A1 | 3/2011 |
| WO | 2011051726 A2 | 5/2011 |
| WO | 2011066342 A2 | 6/2011 |
| WO | 2011076786 A1 | 6/2011 |
| WO | 2011090754 A1 | 7/2011 |
| WO | 2011101409 A1 | 8/2011 |
| WO | 2011155607 A1 | 12/2011 |
| WO | 2012022814 A1 | 2/2012 |
| WO | 2013039954 A1 | 3/2013 |
| WO | 2013079174 A1 | 6/2013 |
| WO | 2013111105 A1 | 8/2013 |
| WO | 2013124826 A1 | 8/2013 |
| WO | 2013171639 A1 | 11/2013 |
| WO | 2013171640 A1 | 11/2013 |
| WO | 2013171641 A1 | 11/2013 |
| WO | 2013171642 A1 | 11/2013 |
| WO | 2013184757 A1 | 12/2013 |
| WO | 2013185052 | 12/2013 |
| WO | 2014008218 A1 | 1/2014 |
| WO | 2014012479 A1 | 1/2014 |
| WO | 2014018632 A1 | 1/2014 |
| WO | 2014072493 A1 | 5/2014 |
| WO | 2014085318 A1 | 6/2014 |
| WO | 2014093936 A1 | 6/2014 |
| WO | 2014099824 | 6/2014 |
| WO | 2014141104 A1 | 9/2014 |
| WO | 2014151616 A1 | 9/2014 |
| WO | 2014160160 A2 | 10/2014 |
| WO | 2014179335 A1 | 11/2014 |
| WO | 2014189805 A1 | 11/2014 |
| WO | 2015026684 A1 | 2/2015 |
| WO | 2015066188 A1 | 5/2015 |
| WO | 2015069770 | 5/2015 |
| WO | 2015138600 A2 | 9/2015 |
| WO | 2015185565 A1 | 12/2015 |
| WO | 2016096174 A1 | 6/2016 |
| WO | 2016145102 | 9/2016 |
| WO | 2017027645 | 2/2017 |
| WO | 2017027646 A1 | 2/2017 |
| WO | 2017059224 | 4/2017 |
| WO | 2017075477 A1 | 5/2017 |

OTHER PUBLICATIONS

Bala et al., PLGA Nanoparticles in Drug Delivery: The State of the Art. Crit Rev Ther Drug Carrier Syst. 2004;21(5):387-422.
Barber, Cytoplasmic DNA innate immune pathways. Immunol Rev. Sep. 2011;243(1):99-108.
Burdette and Vance, STING and the innate immune response to nucleic acids in the cytosol. Nat Immunol. Jan. 2013;14(1):19-26.
Burdette et al., STING is a direct innate immune sensor of cyclic di-GMP. Nature. Sep. 25, 2011;478(7370):515-518.
Caskey et al., Synthetic double-stranded RNA induces innate immune responses similar to a live viral vaccine in humans. J Exp Med. Nov. 21, 2011;208(12):2357-2366.
Civril et al., Structural mechanism of cytosolic DNA sensing by cGAS. Nature. Jun. 20, 2013;498(7454):332-337.
Coffman et al., Vaccine adjuvants: putting innate immunity to work. Immunity. Oct. 29, 2010;33(4):492-503.
Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.

(56) References Cited

OTHER PUBLICATIONS

Crimmins et al., Listeria monocytogenes multidrug resistance transporters activate a cytosolic surveillance pathway of innate immunity. Proc Natl Acad Sci U S A. Jul. 22, 2008;105(29):10191-10196.
Davies et al., Coordinated Regulation of Accessory Genetic Elements Produces Cyclic Di-Nucleotides for V. cholerae Virulence. Cell. Apr. 13, 2012;149(2):358-370.
Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.
Din et al., Effective use of nanocarriers as drug delivery systems for the treatment of selected tumors. Int J Nanomedicine. Oct. 5, 2017;12:7291-7309.
Diner et al., The Innate Immune DNA Sensor cGAS Produces a Noncanonical Cyclic Dinucleotide that Activates Human STING. Cell Rep. May 30, 2013;3(5):1355-1361.
Dubensky and Reed, Adjuvants for cancer vaccines. Semin Immunol. Jun. 2010;22(3):155-161.
Eager and Nemunaitis, GM-CSF Gene-Transduced Tumor Vaccines. Mol Ther. Jul. 2005;12(1):18-27.
Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.
Gao et al., Cyclic [G(20,50)pA(30,50)p] is the Metazoan Second Messenger Produced by DNA-Activated Cyclic GMP-AMP Synthase. Cell. May 23, 2013;153(5):1094-1107.
Gao et al., Structure-Function Analysis of STING Activation by c[G(2',5')pA(3',5')p] and Targeting by Antiviral DMXAA. Cell. Aug. 15, 2013;154(4):748-762.
Hamid et al., Safety and Tumor Responses with Lambrolizumab (Anti-PD-1) in Melanoma. N Engl J Med. Jul. 11, 2013;369(2):134-144.
Hughes, Nanostructure-mediated Drug Delivery. Nanomedicine. Mar. 2005;1(1):22-30.
Ireton and Gale, RIG-I Like Receptors in Antiviral Immunity and Therapeutic Applications. Viruses. Jun. 2011;3(6):906-919.
Ishikawa and Barber, STING an Endoplasmic Reticulum Adaptor that Facilitates Innate Immune Signaling. Nature. Oct. 2, 2008;455(7213):674-678.
Iwasaki and Medzhitov, Regulation of adaptive immunity by the innate immune system. Science. Jan. 15, 2010;327(5963):291-295.
Jin et al., Identification and characterization of a loss-of-function human MPYS variant. Genes Immun. Jun. 2011;12(4):263-269.
Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kranzusch et al., Structure of Human cGAS Reveals a Conserved Family of Second-Messenger Enzymes in Innate Immunity. Cell Rep. May 30, 2013;3(5):1362-1368.
Leber et al., Distinct TLR- and NLR-Mediated Transcriptional Responses to an Intracellular Pathogen. PLoS Pathog. Jan. 2008;4(1):e6.
Mccune et al., Active specific immunotherapy with tumor cells and Corynebacterium parvum: A phase I study. Cancer. May 1979;43(5):1619-1623.
Mcwhirter et al., A host type I interferon response is induced by cytosolic sensing of the bacterial second messenger cyclic-di-GMP. J Exp Med. Aug. 31, 2009;206(9):1899-1911.
Muderhwa et al., Oil-in-water liposomal emulsions: Characterization and potential use in vaccine delivery. J Pharm Sci. Dec. 1999;88(12):1332-1339.
Nelson and Griswold, A computer program for calculating antibody affinity constants. Comput Methods Programs Biomed. Jul.-Aug. 1988;27(1):65-68.
Niesen et al, The use of differential scanning fluorimetry to detect ligand interactions that promote protein stability. Nat Protoc. 2007;2(9):2212-2221.
Pandey et. al., Microbial Sensing by Toll-Like Receptors and Intracellular Nucleic Acid Sensors. Cold Spring Harb Perspect Biol. Oct. 9, 2014;7(1):a016246.
Pulendran and Ahmed, Immunological Mechanisms of Vaccination. Nat Immunol. Jun. 2011;12(6):509-517.
Reed et al., New horizons in adjuvants for vaccine development. Trends Immunol. Jan. 2009;30(1):23-32.
Römling et al., Cyclic di-GMP: the First 25 Years of a Universal BacterialSecond Messenger. Microbiol Mol Biol Rev. Mar. 2013;77(1):1-52.
Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.
Strbo et al., Secreted heat shock protein gp96-Ig: next-generation vaccines for cancer and infectious diseases. Immunol Res. Dec. 2013;57(1-3):311-325.
Sun et al., Cyclic GMP-AMP Synthase Is a Cytosolic DNA Sensor That Activates the Type I Interferon Pathway. Science. Feb. 15, 2013;339(6121):786-791.
Van Erp et al., Application of a sol particle immunoassay to the determination of affinity constants of monoclonal antibodies. J Immunoassay. 1991;12(3):425-443.
Vance et al., Patterns of Pathogenesis: Discrimination of Pathogenic and Nonpathogenic Microbes by the Innate Immune System. Cell Host Microbe. Jul. 23, 2009;6(1):10-21.
Ward et al., Binding activities of a repertoire of single immunoglobulin variable domains secreted from *Escherichia coli*. Nature. Oct. 12, 1989;341(6242):544-546.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Cyclic di-AMP Is Critical for Listeria monocytogenes Growth, Cell Wall Homeostasis, and Establishment of Infection. MBio. May 28, 2013;4(3):e00282-13 (10 pages).
Woodward et al., c-di-AMP secreted by intracellular Listeria monocytogenes activates a host type I interferon response. Science. Jun. 25, 2010;328(5986):1703-1705.
Woodward et al., Supporting online material May 27, 2010 on Science Express DOI: 10.1126/science.1189801 (15 pages).
Wu et al., Corrected Supplemental Materials for Cyclic GMP-AMP is an Endogeneous Second Messenger in Innate Immune Signaling by Cytosolic DNA. Science, Jan. 10, 2013 :21 pages.
Wu et al., Cyclic GMP-AMP is an Endogeneous Second Messenger in Innate Immune Signaling by Cytosolic DNA. Science. Feb. 15, 2013;339(6121):826-830—includes supplemental material (15 pages total).
Xiao and Fitzgerald, The cGAS-STING Pathway for DNA Sensing. Mol Cell. Jul. 25, 2013;51(2):135-139.
Yamazaki et al., Cutting Edge: Tumor Secreted Heat Shock-Fusion Protein Elicits CD8 Cells for Rejection. J Immunol. Nov. 15, 1999;163(10):5178-5182.
Yan et al., Synthesis and immunostimulatory properties of the phosphorothioate analogues of cdiGMP. Bioorg Med Chem Lett. Oct. 15, 2008;18(20):5631-5634.
Yarmush et al., Coupling of antibody-binding fragments to solid-phase supports: site-directed binding of F(ab')2 fragments. J Biochem Biophys Methods. Dec. 1992;25(4):285-297.
Yi et al., Single Nucleotide Polymorphisms of Human STING Can Affect Innate Immune Response to Cyclic Dinucleotides. PLoS One. Oct. 21, 2013;8(10):e77846.
Zhang et al., Cyclic GMP-AMP Containing Mixed Phosphodiester Linkages is an Endogenous High-Affinity Ligand for STING. Mol Cell. Jul. 25, 2013;51(2):226-235.
Zhao et al., Thiophosphate Analogs of c-di-GMP: Impact on Polymorphism. Nucleosides Nucleotides Nucleic Acids. May 2009;28(5):352-378.

SEQUENCE LISTING

<160> NUMBER OF SEQ ID NOS: 22

<210> SEQ ID NO 1
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Gln Val Gln Leu Val Glu Ser Gly Gly Gly Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

```
Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
            435                 440

<210> SEQ ID NO 2
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 447
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 3

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 4
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 5
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Val Asp Tyr Trp Gly Gln Gly Thr
            100                 105                 110

Leu Val Thr Val Ser Ser
            115

<210> SEQ ID NO 6
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 7
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tacttccaat ccaatgcagc cccagctgag atctctg                          37

<210> SEQ ID NO 8
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 8
ttatccactt ccaatgttat tattatcaag agaaatccgt gcggag        46

<210> SEQ ID NO 9
<211> LENGTH: 240
<212> TYPE: PRT
<213> ORGANISM: Homo sapiens

<400> SEQUENCE: 9

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Gly Asp Arg Ala Gly Ile
                85                  90                  95

Lys Asp Arg Val Tyr Ser Asn Ser Ile Tyr Glu Leu Leu Glu Asn Gly
            100                 105                 110

Gln Arg Ala Gly Thr Cys Val Leu Glu Tyr Ala Thr Pro Leu Gln Thr
        115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Arg Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
            180                 185                 190

His Leu Arg Gln Glu Glu Lys Glu Glu Val Thr Val Gly Ser Leu Lys
        195                 200                 205

Thr Ser Ala Val Pro Ser Thr Ser Thr Met Ser Gln Glu Pro Glu Leu
    210                 215                 220

Leu Ile Ser Gly Met Glu Lys Pro Leu Pro Leu Arg Thr Asp Phe Ser
225                 230                 235                 240

<210> SEQ ID NO 10
<211> LENGTH: 240
<212> TYPE: PRT
<213> ORGANISM: Homo sapiens

<400> SEQUENCE: 10

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

```
Arg Phe Leu Asp Lys Leu Pro Gln Gln Thr Gly Asp His Ala Gly Ile
                85                  90                  95

Lys Asp Arg Val Tyr Ser Asn Ser Ile Tyr Glu Leu Leu Glu Asn Gly
            100                 105                 110

Gln Arg Ala Gly Thr Cys Val Leu Glu Tyr Ala Thr Pro Leu Gln Thr
        115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Arg Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
            180                 185                 190

His Leu Arg Gln Glu Glu Lys Glu Glu Val Thr Val Gly Ser Leu Lys
        195                 200                 205

Thr Ser Ala Val Pro Ser Thr Ser Thr Met Ser Gln Glu Pro Glu Leu
    210                 215                 220

Leu Ile Ser Gly Met Glu Lys Pro Leu Pro Leu Arg Thr Asp Phe Ser
225                 230                 235                 240

<210> SEQ ID NO 11
<211> LENGTH: 240
<212> TYPE: PRT
<213> ORGANISM: Homo sapiens

<400> SEQUENCE: 11

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Ala Asp Arg Ala Gly Ile
                85                  90                  95

Lys Asp Arg Val Tyr Ser Asn Ser Ile Tyr Glu Leu Leu Glu Asn Gly
            100                 105                 110

Gln Arg Ala Gly Thr Cys Val Leu Glu Tyr Ala Thr Pro Leu Gln Thr
        115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Gln Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
            180                 185                 190

His Leu Arg Gln Glu Glu Lys Glu Glu Val Thr Val Gly Ser Leu Lys
        195                 200                 205

Thr Ser Ala Val Pro Ser Thr Ser Thr Met Ser Gln Glu Pro Glu Leu
```

Leu Ile Ser Gly Met Glu Lys Pro Leu Pro Leu Arg Thr Asp Phe Ser
225                 230                 235                 240

<210> SEQ ID NO 12
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Gly Ser Ser His His His His His His Gly Ser Ser Met Ala Ser
1               5                   10                  15

Met Ser Asp Ser Glu Val Asn Gln Glu Ala Lys Pro Glu Val Lys Pro
            20                  25                  30

Glu Val Lys Pro Glu Thr His Ile Asn Leu Lys Val Ser Asp Gly Ser
        35                  40                  45

Ser Glu Ile Phe Phe Lys Ile Lys Lys Thr Thr Pro Leu Arg Arg Leu
    50                  55                  60

Met Glu Ala Phe Ala Lys Arg Gln Gly Lys Glu Met Asp Ser Leu Arg
65                  70                  75                  80

Phe Leu Tyr Asp Gly Ile Arg Ile Gln Ala Asp Gln Thr Pro Glu Asp
                85                  90                  95

Leu Asp Met Glu Asp Asn Asp Ile Ile Glu Ala His Arg Glu Gln Ile
            100                 105                 110

Gly Gly Ile Glu Glu Asn Leu Tyr Phe Gln Ser Asn Ala Ala Pro Ala
        115                 120                 125

Glu Ile Ser Ala Val Cys Glu Lys Gly Asn Phe Asn Val Ala His Gly
    130                 135                 140

Leu Ala Trp Ser Tyr Tyr Ile Gly Tyr Leu Arg Leu Ile Leu Pro Glu
145                 150                 155                 160

Leu Gln Ala Arg Ile Arg Thr Tyr Asn Gln His Tyr Asn Asn Leu Leu
                165                 170                 175

Arg Gly Ala Val Ser Gln Arg Leu Tyr Ile Leu Leu Pro Leu Asp Cys
            180                 185                 190

Gly Val Pro Asp Asn Leu Ser Met Ala Asp Pro Asn Ile Arg Phe Leu
        195                 200                 205

Asp Lys Leu Pro Gln Gln Thr Gly Asp Arg Ala Gly Ile Lys Asp Arg
    210                 215                 220

Val Tyr Ser Asn Ser Ile Tyr Glu Leu Leu Glu Asn Gly Gln Arg Ala
225                 230                 235                 240

Gly Thr Cys Val Leu Glu Tyr Ala Thr Pro Leu Gln Thr Leu Phe Ala
                245                 250                 255

Met Ser Gln Tyr Ser Gln Ala Gly Phe Ser Arg Glu Asp Arg Leu Glu
            260                 265                 270

Gln Ala Lys Leu Phe Cys Arg Thr Leu Glu Asp Ile Leu Ala Asp Ala
        275                 280                 285

Pro Glu Ser Gln Asn Asn Cys Arg Leu Ile Ala Tyr Gln Glu Pro Ala
    290                 295                 300

Asp Asp Ser Ser Phe Ser Leu Ser Gln Glu Val Leu Arg His Leu Arg
305                 310                 315                 320

Gln Glu Glu Lys Glu Glu Val Thr Val Gly Ser Leu Lys Thr Ser Ala
                325                 330                 335

```
Val Pro Ser Thr Ser Thr Met Ser Gln Glu Pro Glu Leu Leu Ile Ser
            340                 345                 350

Gly Met Glu Lys Pro Leu Pro Leu Arg Thr Asp Phe Ser
            355                 360                 365

<210> SEQ ID NO 13
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Gly Ser Ser His His His His His His Gly Ser Ser Met Ala Ser
1               5                   10                  15

Met Ser Asp Ser Glu Val Asn Gln Glu Ala Lys Pro Glu Val Lys Pro
            20                  25                  30

Glu Val Lys Pro Glu Thr His Ile Asn Leu Lys Val Ser Asp Gly Ser
            35                  40                  45

Ser Glu Ile Phe Phe Lys Ile Lys Lys Thr Thr Pro Leu Arg Arg Leu
    50                  55                  60

Met Glu Ala Phe Ala Lys Arg Gln Gly Lys Glu Met Asp Ser Leu Arg
65                  70                  75                  80

Phe Leu Tyr Asp Gly Ile Arg Ile Gln Ala Asp Gln Thr Pro Glu Asp
                85                  90                  95

Leu Asp Met Glu Asp Asn Asp Ile Ile Glu Ala His Arg Glu Gln Ile
            100                 105                 110

Gly Gly Ile Glu Glu Asn Leu Tyr Phe Gln Ser Asn Ala Ala Pro Ala
            115                 120                 125

Glu Ile Ser Ala Val Cys Glu Lys Gly Asn Phe Asn Val Ala His Gly
130                 135                 140

Leu Ala Trp Ser Tyr Tyr Ile Gly Tyr Leu Arg Leu Ile Leu Pro Glu
145                 150                 155                 160

Leu Gln Ala Arg Ile Arg Thr Tyr Asn Gln His Tyr Asn Asn Leu Leu
                165                 170                 175

Arg Gly Ala Val Ser Gln Arg Leu Tyr Ile Leu Leu Pro Leu Asp Cys
            180                 185                 190

Gly Val Pro Asp Asn Leu Ser Met Ala Asp Pro Asn Ile Arg Phe Leu
            195                 200                 205

Asp Lys Leu Pro Gln Gln Thr Gly Asp His Ala Gly Ile Lys Asp Arg
    210                 215                 220

Val Tyr Ser Asn Ser Ile Tyr Glu Leu Leu Glu Asn Gly Gln Arg Ala
225                 230                 235                 240

Gly Thr Cys Val Leu Glu Tyr Ala Thr Pro Leu Gln Thr Leu Phe Ala
                245                 250                 255

Met Ser Gln Tyr Ser Gln Ala Gly Phe Ser Arg Glu Asp Arg Leu Glu
            260                 265                 270

Gln Ala Lys Leu Phe Cys Arg Thr Leu Glu Asp Ile Leu Ala Asp Ala
            275                 280                 285

Pro Glu Ser Gln Asn Asn Cys Arg Leu Ile Ala Tyr Gln Glu Pro Ala
    290                 295                 300

Asp Asp Ser Ser Phe Ser Leu Ser Gln Glu Val Leu Arg His Leu Arg
305                 310                 315                 320
```

```
Gln Glu Glu Lys Glu Glu Val Thr Val Gly Ser Leu Lys Thr Ser Ala
            325                 330                 335

Val Pro Ser Thr Ser Thr Met Ser Gln Glu Pro Glu Leu Leu Ile Ser
        340                 345                 350

Gly Met Glu Lys Pro Leu Pro Leu Arg Thr Asp Phe Ser
        355                 360                 365

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
gctgagacag gagctttgg                                                 19

<210> SEQ ID NO 15
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
agccagagag gttcaagga                                                 19

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ggccaatgac ctgggtctca                                                20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
cacccagaat agcatccagc                                                20

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
tcagagttgg gtatcagagg c                                              21
```

```
<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
atctggtgtg ctgggaagag g                                             21

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Pro Ser Tyr Val Tyr His Gln Phe
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Val Val Pro Pro
1               5

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 22

His His His His His His
1               5
```

BIS 2'-5'-RR-(3'F-A)(3'F-A) CYCLIC DINUCLEOTIDE COMPOUND AND USES THEREOF

RELATED APPLICATIONS

This application is a National Phase of PCT/IB2018/052918 filed Apr. 26, 2018 which claims priority to, and the benefit of, U.S. Application Ser. Nos. 62/491,879, filed Apr. 28, 2017 and 62/578,172, filed Oct. 27, 2017. The contents of each of these applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 11, 2018, is named PAT057968-WO-PCT_SL.txt and is 30,090 bytes in size.

BACKGROUND OF THE INVENTION

The following discussion of the background of the invention is merely provided to aid the reader in understanding the invention and is not admitted to describe or constitute prior art to the present invention.

New insights into the mechanisms underlying immune-evasion, together with combination treatment regimens that potentiate the potency of therapeutic vaccination, either directly or indirectly, through combination with immune checkpoint inhibitors or other therapies, have served as a basis for the development of vaccines or immune modulators that can prime or boost an effective adaptive immune response. These modulators consist of tumor-specific CD4$^+$ and CD8$^+$ T cells specific for a targeted malignancy, resulting in an antitumor response and clinical benefit. How the innate immune system is engaged by targeted ligands shapes the development of an adaptive response and lends itself to the design of vaccines and immunomodulators (Reed et al., Trends Immunol., 30: 23-32, 2009; Dubensky and Reed, Semin. Immunol., 22: 155-61, 2010; Kastenmuller et al., J. Clin. Invest., 121: 1782-1796, 2011; Coffman et al., Immunity, 33: 492-503, 2010).

The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). It is now recognized that STING is a component of the host cytosolic surveillance pathway (Vance et al., Cell Host & Microbe, 6:10-21, 2009), that senses infection with intracellular pathogens and in response induces the production of IFN-β, leading to the development of an adaptive protective pathogen-specific immune response consisting of both antigen-specific CD4$^+$ and CD8$^+$ T cells as well as pathogen-specific antibodies.

Cells expressing human STING (hSTING) reportedly respond poorly to stimulation with bacterial CDNs cGAMP, c-di-AMP and c-di-GMP having bis-(3',5') linkages, but are responsive to the endogenously produced cGAS product, ML cGAMP (Diner et al., Cell Reports, 3:1355-1361, 2013). Thus, it has been suggested that the 2',5'-3',5' molecules represent much more potent physiological ligands in terms of hSTING targeting (Zhang et al., Mol. Cell. 51:226-35, 2013; Xiao and Fitzgerald, Mol. Cell 51:135-39, 2013).

There are therapeutic applications for compounds that target hSTING as either an agonist (e.g., increasing the tumor-specific CD4$^+$ and CD8$^+$ T cells specific for a targeted malignancy, or improving a response to vaccination) or as an antagonist (e.g., decreasing a type I interferon response associated with autoimmune disease). Thus there is a desire for improved compounds for the modulation of hSTING.

SUMMARY OF THE INVENTION

It is an object of the present invention to provide compositions and methods which modulate immune responses to diseases. It is a further object of the invention to provide compositions and methods which provide a bis 2'-5' linked cyclic dinucleotide that exhibits improved characteristics when employed for modulation of mammalian, and preferably human, STING. It is yet a further object of the invention to provide a bis 2'-5' linked cyclic dinucleotide that activate hSTING, and compositions and methods thereof for the treatment of cancer.

In a first aspect, the present invention provides the compound dithio-(Rp,Rp)-cyclic-[3'F-A(2',5')p-3'F-A(2',5')p], also referred to as 2'2'-RR-(3'F-A)(3'F-A) or bis 2'-5'-RR-(3'F-A)(3'F-A), or named (1S,3R,6R,8R,9S,11R,14R,16R,17R,18R)-8,16-bis(6-amino-9H-purin-9-yl)-17,18-difluoro-3,11-dimercapto-2,4,7,10,12,15-hexaoxa-3,11-diphosphatricyclo[12.2.1.1$^{6,9}$]octadecane 3,11-dioxide, having the structure:

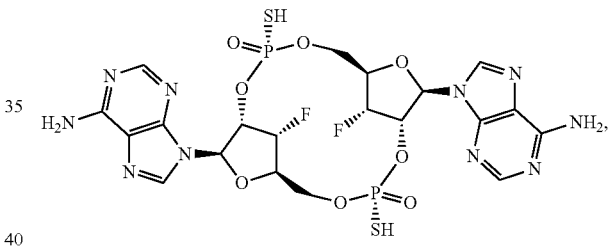

or a tautomer, pharmaceutically acceptable salt, pharmaceutically acceptable solvate or pharmaceutically acceptable hydrate thereof.

In some embodiments of the first aspect, the compound of the invention includes pharmaceutically acceptable salts, pharmaceutically acceptable solvates or pharmaceutically acceptable hydrates of 2'2'-RR-(3'F-A)(3'F-A) or a tautomer thereof, including any pharmaceutically acceptable solvates or pharmaceutically acceptable hydrates of any pharmaceutically acceptable salts of 2'2'-RR-(3'F-A)(3'F-A) or a tautomer thereof. In some embodiments, the compound of the invention includes pharmaceutically acceptable solvates, pharmaceutically acceptable hydrates or pharmaceutically acceptable salts of 2'2'-RR-(3'F-A)(3'F-A). In some embodiments, the compound of the invention is a pharmaceutically acceptable salt of 2'2'-RR-(3'F-A)(3'F-A) or a tautomer thereof, or a pharmaceutically acceptable solvate or pharmaceutically acceptable hydrate thereof. In some embodiments, the compound of the invention is a pharmaceutically acceptable salt of 2'2'-RR-(3'F-A)(3'F-A) or a tautomer thereof.

In some embodiments, the pharmaceutically acceptable salt is selected from the group consisting of the sodium, potassium, calcium, magnesium, zinc, aluminum, ammonium, diethylamine, isopropylamine, olamine, benzathine, benethamine, tromethamine (2-amino-2-(hydroxymethyl)

propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine, lysine and arginine salt.

In some embodiments, 2'2'-RR-(3'F-A)(3'F-A) is provided as the disodium salt thereof. In some embodiments, 2'2'-RR-(3'F-A)(3'F-A) is provided as the disodium salt thereof, or a pharmaceutically acceptable solvate or pharmaceutically acceptable hydrate thereof.

In some embodiments, 2'2'-RR-(3'F-A)(3'F-A) or a tautomer, pharmaceutically acceptable salt, pharmaceutically acceptable solvate or pharmaceutically acceptable hydrate thereof is a STING agonist.

In a second aspect, the present invention provides a pharmaceutical composition comprising 2'2'-RR-(3'F-A)(3'F-A), as described in the first aspect, and any embodiments thereof as described herein above, including any tautomers, pharmaceutically acceptable salts, pharmaceutically acceptable solvates, or pharmaceutically acceptable hydrates thereof, and a delivery vehicle which enhances cellular uptake and/or stability of the compound. In some embodiments, the delivery vehicle comprises one or more agents selected from the group consisting of adjuvants, lipids, liposomes, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers. In some embodiments, the delivery vehicle is a nanoparticle comprising one or more agents selected from the group consisting of adjuvants, lipids, liposomes, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In a third aspect, the present invention provides a pharmaceutical composition comprising 2'2'-RR-(3'F-A)(3'F-A), as described in the first aspect and any embodiments thereof, including any tautomers, pharmaceutically acceptable salts, pharmaceutically acceptable solvates, or pharmaceutically acceptable hydrates thereof, and a pharmaceutically acceptable excipient.

In a first embodiment of the third aspect, the pharmaceutical composition does not include an agent that enhances cellular permeability of 2'2'-RR-(3'F-A)(3'F-A) or a tautomer, pharmaceutically acceptable salt, pharmaceutically acceptable solvate or pharmaceutically acceptable hydrate thereof.

In a second embodiment of the third aspect, the pharmaceutical composition does not include an agent that enhances cellular uptake of 2'2'-RR-(3'F-A)(3'F-A) or a tautomer, pharmaceutically acceptable salt, pharmaceutically acceptable solvate or pharmaceutically acceptable hydrate thereof.

In a third embodiment of the third aspect, the pharmaceutical composition further comprises a delivery vehicle which enhances cellular uptake and/or stability of the compound. In some embodiments, the delivery vehicle comprises one or more agents selected from the group consisting of adjuvants, lipids, liposomes, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers. In some embodiments, the delivery vehicle is a nanoparticle comprising one or more agents selected from the group consisting of adjuvants, lipids, liposomes, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In some embodiments of the second or third aspect and any of the above embodiments thereof, the pharmaceutical composition further comprises one or more additional pharmaceutically active components selected from the group consisting of an immune checkpoint inhibitor (e.g., CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies PDR001 (Novartis), nivolumab, pembrolizumab or pidilizumab; PD-1 inhibitor AMP-224; anti-CTLA-4 antibody ipilimumab; anti-PD-L1 antibodies BMS-936559, MPDL3280A, MEDI4736, or avelumab; Vista inhibitors including anti-Vista antibodies; B7-H3 inhibitors including anti-B7-H3 antibodies; and CD70 inhibitors including anti-CD70 antibodies); Co-stimulatory checkpoint receptor agonist (e.g., CD40 agonists, including an anti-CD40 antibody; CD137 agonists, including an anti-CD137 antibody; GITR agonists, including an anti-GITR antibody; OX40 agonists, including an anti-OX40 antibody); a TLR agonist (e.g., CpG or monophosphoryl lipid A); an inactivated or attenuated bacteria which induce innate immunity (e.g., inactivated or attenuated *Listeria monocytogenes*); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent. In some embodiments, the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist. In some embodiments, the immune checkpoint inhibitor is an anti-PD-1 antibody, an anti-PD-L1 antibody, an anti-CTLA-4 antibody, an anti-TIM-3 antibody, an anti-Vista antibody, an anti-BTLA antibody, an anti-B7-H3 antibody, an anti-CD70 antibody, an anti-KIR antibody or an anti-LAG-3 antibody. In some embodiments, the immune checkpoint inhibitor is selected from the group consisting of nivolumab, pembrolizumab, pidilizumab, PDR001, MEDI0680, REGN2810, AMP-224, ipilimumab, BMS-936559, MPDL3280A, MEDI4736, and avelumab. In some embodiments, the TLR agonist is CpG or monophosphoryl lipid A.

In some embodiments of the second or third aspect and any of the above embodiments thereof, the pharmaceutical composition further comprises an inactivated tumor cell which expresses and secretes one or more cytokines which stimulate dendritic cell induction, recruitment and/or maturation, or which expresses and secretes one or more heat shock proteins, including gp96-Ig fusion proteins. In some embodiments, the one or more cytokines is selected from the group consisting of GM-CSF, CCL20, CCL3, IL-12p70 and FLT-3 ligand. In some embodiments, the tumor cell is inactivated by treatment with radiation. In some embodiments, the one or more cytokines is selected from the group consisting of GM-CSF, CCL20, CCL3, IL-12p70 and FLT-3 ligand, and the tumor cell is inactivated by treatment with radiation. In some embodiments, the inactivated tumor cell expresses and secretes a gp96-Ig fusion protein.

In some embodiments of the second or third aspect and any of the above embodiments thereof, the pharmaceutical composition further comprises one or more antigens selected for the purposes of inducing an immune response against said one or more antigen(s) when the composition is administered to an individual. In some embodiments, the antigen is a recombinant protein antigen. In some embodiments, the antigen is a recombinant protein antigen related to an infectious disease, a malignancy, or an allergan. In some embodiments, the one or more antigens are one or more antigens in Table 1.

In some embodiments of the second or third aspect and any of the above embodiments thereof, the pharmaceutical composition is formulated as aqueous or oil-in-water emulsions.

In a fourth aspect, the invention provides a method for treating an individual suffering from a cancer, wherein the method comprises administering to the individual in need thereof an effective amount of 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above. In some embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is administered non-parenterally or parenterally. In some embodiments, the administration is subcutaneous, intramuscular, intradermal, mucosal, vaginal, cervical, peri-tumoral, intra-tumoral, or directly into the tumor-draining lymph node(s). In some embodiments, the administration is mucosal, preferably oral.

In a first embodiment of the fourth aspect, the individual receiving such treatment may be suffering from a cancer selected from the group consisting of a colorectal cancer, an aero-digestive squamous cancer, a lung cancer (small cell lung cancer, non-small cell lung cancer), a brain cancer, a liver cancer (e.g., hepatocellular carcinoma), a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma (e.g., Hodgkin lymphoma, non-Hodgkin lymphoma), and a multiple myeloma.

In a second embodiment of the fourth aspect and of the first embodiment thereof, the method for treating an individual suffering from a cancer further comprises administering one or more additional cancer therapies. In some embodiments, the one or more additional cancer therapies comprise radiation therapy, surgery, a chemotherapy, or an immunotherapy (for example, without limitation, an immunomodulator, an immune checkpoint inhibitor, a cellular immunotherapy, or a cancer vaccine). In some embodiments, the one or more additional cancer therapies comprise an inactivated tumor cell that expresses and secretes one or more cytokines or one or more heat shock proteins. In some embodiments, the cytokine is selected from the group consisting of GM-CSF, CCL20, CCL3, IL-12p70, and FLT-3 ligand. In some embodiments the heat shock protein is a gp96-Ig protein. In some embodiments, the method comprises administering one or more additional cancer therapies selected from the group consisting of a chemotherapeutic agent; an immune checkpoint inhibitor; a TLR agonist; a vaccine selected to stimulate an immune response to one or more cancer antigens, a therapeutic antibody that induces antibody-dependent cellular cytotoxicity; an immunomodulatory cell line; an inactivated or attenuated bacteria that induces innate immunity; an antigen selected for the purpose of inducing an immune response, and a composition that mediates innate immune activation via Toll-like Receptors (TLRs), (NOD)-like receptors (NLRs), Retinoic acid inducible gene-based (RIG)-I-like receptors (RLRs), C-type lectin receptors (CLRs) or pathogen-associated molecular patterns ("PAMPs"). In some embodiments, the immune checkpoint inhibitor is an anti-PD-1 antibody, an anti-PD-L1 antibody, an anti-CTLA-4 antibody, an anti-TIM-3 antibody, an anti-Vista antibody, an anti-BTLA antibody, an anti-B7-H3 antibody, an anti-CD70 antibody, an anti-KIR antibody or an anti-LAG-3 antibody. In some embodiments, the immune checkpoint inhibitor is PDR001 (Novartis). In some embodiments, the TLR agonist is CpG or monophosphoryl lipid A. In some embodiments, the therapeutic antibody that induces antibody-dependent cellular cytotoxicity is rituximab, ibritumomab, tositumomab, cetuximab, trastuzumab, brentuximab vedotin, alemtuzumab, oncolym, ipilimumab, vitaxin, or bevacizumab.

In some embodiments of the fourth aspect and first and second embodiments thereof, the individual suffers from a cancer expressing a cancer antigen, and the method for treating said individual further comprises administering to the individual a primary therapy to remove or kill cancer cells expressing the cancer antigen, wherein the administration of the primary therapy is simultaneously with, prior to or following administration of 2'2'-RR-(3'F-A)(3'F-A) or a tautomer, pharmaceutically acceptable salt, pharmaceutically acceptable solvate, or pharmaceutically acceptable hydrate thereof, or a composition thereof. In some embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is administered as a neoadjuvant therapy to the primary therapy. In preferred embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is administered following the primary therapy. In some embodiments, the primary therapy comprises surgery to remove the cancer cells from the mammal, radiation therapy to kill the cancer cells in the mammal, or both surgery and radiation therapy.

In a fifth aspect, the invention provides a method of treating a disease in an individual, comprising administering to the individual in need thereof i) an effective amount of 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above; and ii) an effective amount of one or more therapeutic antibodies that induce antibody-dependent cellular cytotoxicity, wherein the disease is selected from the group consisting of a cancer, acute rejection of an organ transplant, Type I diabetes mellitus, rheumatoid arthritis, psoriasis, Crohn's disease, restenosis and allergic asthma. In some embodiments, the cancer is selected from the group consisting of lymphoma (e.g., B-cell lymphoma), breasts cancer, chronic lymphocytic leukemia, colorectal cancer, melanoma, non-small cell lung carcinoma, small cell lung cancer, bladder cancer, prostate cancer and other solid tumors. In some embodiments, the therapeutic antibody is selected from the group consisting of muromonab-CD3, infliximab, daclizumab, omalizumab, abciximab, rituximab, ibritumomab, tositumomab, cetuximab, trastuzumab, brentuximab vedotin, alemtuzumab, oncolym, ipilimumab, vitaxin, and bevacizumab.

In a sixth aspect, the invention provides a method for the treatment of disorders in which shifting of Th1 to Th2 immunity confers clinical benefit, wherein the method comprises administering to the individual in need thereof 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4, IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

In a seventh aspect, the invention provides a method for treating an individual suffering from a chronic infectious disease, wherein the method comprises administering to the individual in need thereof an effective amount of 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above. In some embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is administered in combination with another agent for use in treating the chronic infectious disease. In some embodiments, the chronic infectious disease is selected from the group consisting of HBV infection, HCV infection, HPV infection, HSV infection and hepatocellular cancer.

2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above, may be administered to individuals in need thereof, as described in the methods of the fourth through seventh aspects and any embodiments thereof as described herein above, by a variety of parenteral and non-parenteral routes in formulations containing pharmaceutically acceptable excipients (e.g., carriers, adjuvants, vehicles and the like). Preferred non-parenteral routes include mucosal (e.g., oral, vaginal, nasal, cervical, etc.) routes. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peri-tumoral routes.

2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein may be co-administered to individuals in need thereof, as described in the methods of the fourth through seventh aspects and any embodiments thereof as described herein above, with one or more additional pharmaceutically active components such as adjuvants, lipids, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers, immune checkpoint inhibitors (e.g., CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies PDR001, nivolumab, pembrolizumab or pidilizumab; PD-1 inhibitor AMP-224; anti-CTLA-4 antibody ipilimumab; anti-PD-L1 antibodies BMS-936559, MPDL3280A, MEDI4736, or avelumab; Vista inhibitors including anti-Vista antibodies; B7-H3 inhibitors including anti-B7-H3 antibodies; and CD70 inhibitors including anti-CD70 antibodies), inactivated or attenuated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), or pathogen-associated molecular patterns ("PAMPs"), or chemotherapeutic agents.

In an eighth aspect, the invention provides 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above, for use as adjuvants in combination with a therapeutic or prophylactic vaccine. In some embodiments, the vaccine is selected to stimulate an immune response to one or more predetermined antigens. In some embodiments, the vaccine comprises one or more antigens, including a recombinant protein antigen related to an infectious disease, a malignancy, or an allergan. In some embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is used simultaneously with, prior to or following the vaccine. In some embodiments, 2'2'-RR-(3'F-A)(3'F-A) or a tautomer, pharmaceutically acceptable salt, pharmaceutically acceptable solvate, or pharmaceutically acceptable hydrate thereof, or a composition thereof is formulated in the same composition as the vaccine.

In a first embodiment of the eighth aspect, the vaccine comprises an inactivated or attenuated bacteria or virus comprising the one or more antigens of interest, one or more purified antigens, live viral or bacterial delivery vectors recombinantly engineered to express and/or secrete the one or more antigens, antigen presenting cell (APC) vectors comprising cells that are loaded with the one or more antigens or transfected with a composition comprising a nucleic acid encoding the one or more antigens, liposomal antigen delivery vehicles, or naked nucleic acid vectors encoding the one or more antigens. In some embodiments, the vaccine is an anti-bacterial, anti-viral, or anti-cancer therapeutic or prophylactic vaccine. In some embodiments, the one or more antigens are one or more antigens selected from the group consisting of a viral antigen, a bacterial antigen and a cancer antigen.

In some embodiments of the eighth aspect and first embodiment thereof, the vaccine comprises an inactivated tumor cell that expresses and secretes one or more cytokines. In some embodiments, the cytokine is selected from the group consisting of GM-CSF, CCL20, CCL3, IL-12p70, and FLT-3 ligand.

In some embodiments of the eighth aspect and first embodiment thereof, the vaccine comprises an inactivated tumor cell that expresses and secretes one or more heat shock proteins. In some embodiments, the heat shock protein is gp96-Ig fusion protein.

In a ninth aspect, the invention provides 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above, for use in treating a disease or indication as described in any of the fourth through eighth aspects and any embodiments thereof as described herein above. In a preferred embodiment, 2'2'-RR-(3'F-A)(3'F-A) or a tautomer, pharmaceutically acceptable salt, pharmaceutically acceptable solvate, or pharmaceutically acceptable hydrate thereof is for use in treating a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma and a multiple myeloma.

In a tenth aspect, the invention provides 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above, for use in the preparation of a medicament for the treatment of a disease or indication as described in any of the fourth through eighth aspects and any embodiments thereof as described herein above. In a preferred embodiment, 2'2'-RR-(3'F-A)(3'F-A) or a tautomer, pharmaceutically acceptable salt, pharmaceutically acceptable solvate, or pharmaceutically acceptable hydrate thereof is for use in preparation of a medicament for the treatment of a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma and a multiple myeloma.

In an eleventh aspect, the invention provides a kit that includes 2'2'-RR-(3'F-A)(3'F-A), as described in the first aspect and any embodiments thereof as described herein above, including any tautomers, pharmaceutically acceptable salts, pharmaceutically acceptable solvates, or pharmaceutically acceptable hydrates thereof, or compositions thereof as described in the second or third aspect and any embodiments thereof as described herein above. In some embodiments, 2'2'-RR-(3'F-A)(3'F-A) or a tautomer, pharmaceutically acceptable salt, pharmaceutically acceptable solvate, or pharmaceutically acceptable hydrate thereof, or a compositions thereof is packaged, e.g., in a vial, bottle or similar container, which may be further packaged, e.g., within a box, envelope, or similar container. In some embodiments, 2'2'-RR-(3'F-A)(3'F-A) or a tautomer, pharmaceutically acceptable salt, pharmaceutically acceptable solvate, or pharmaceutically acceptable hydrate thereof, or a compositions thereof is approved by the U.S. Food and Drug Administration or similar regulatory agency for administration to a mammal, e.g., a human. In one embodiment, such a kit includes written instructions for use and/or other indication that 2'2'-RR-(3'F-A)(3'F-A) or a tautomer, pharmaceutically acceptable salt, pharmaceutically acceptable solvate, or pharmaceutically acceptable hydrate thereof, or a compositions thereof is suitable or approved for administration to a mammal, e.g., a human, for a suitable disease or condition. In some embodiments, the compound or composition is packaged in unit dose or single dose form, e.g., single dose pills, capsules, or the like.

DETAILED DESCRIPTION OF THE INVENTION

Figure 1:
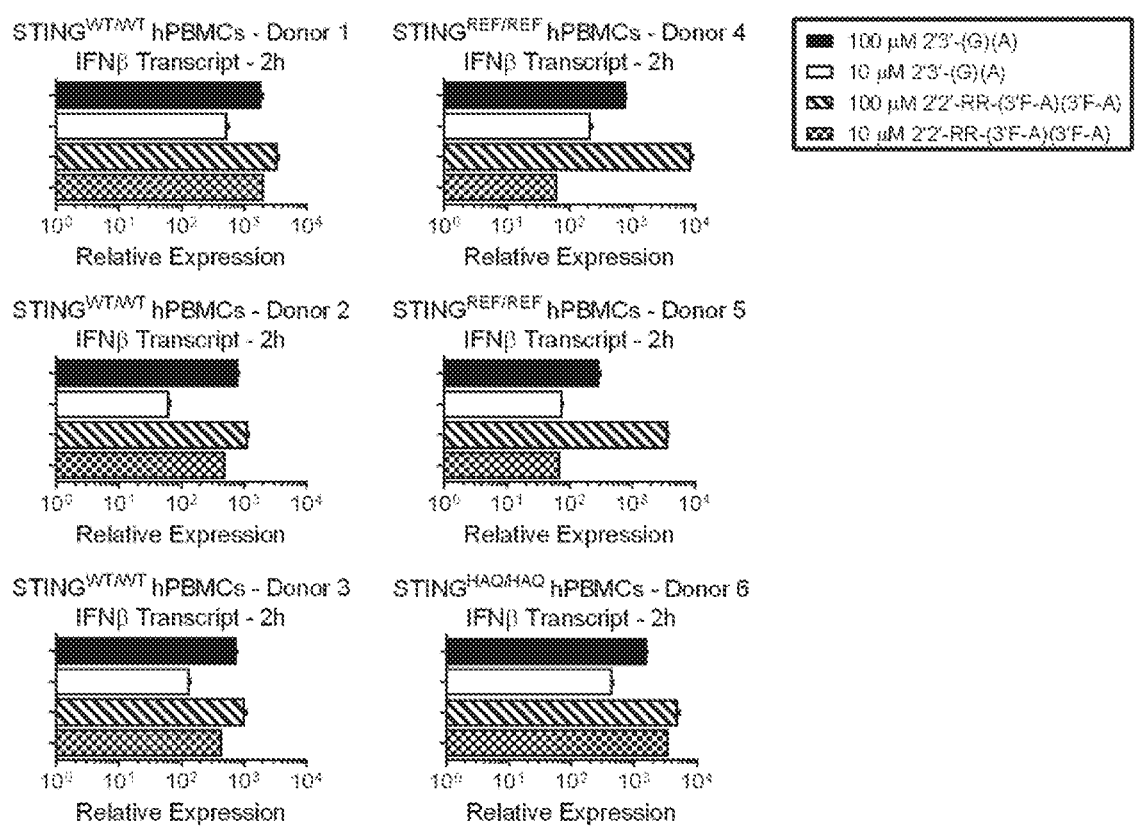
FIG. 1 depicts relative IFNβ expression by 6 donor human PBMCs at 2 hours following stimulation with 10 μM or 100 μM of 2'3'-(G)(A) or 2'2'-RR-(3'F-A)(3'F-A).
Figure 2A:
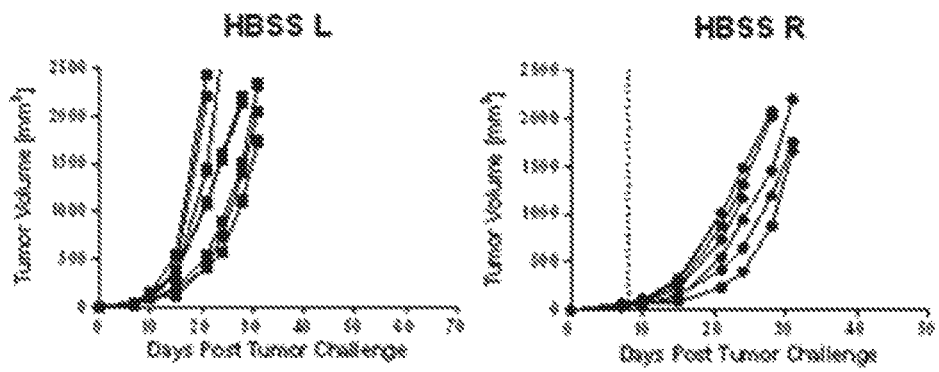
FIGS. 2A-2E depict the tumor volume in injected and distal tumors in a 4T1 mammary carcinoma mouse model, following a single intratumoral injection of Compound 8 at 0.1 μg (2B), 1 μg (2C), 10 μg (2D) or 100 μg (2E) compared to HBSS vehicle control (2A).
Figure 2B:
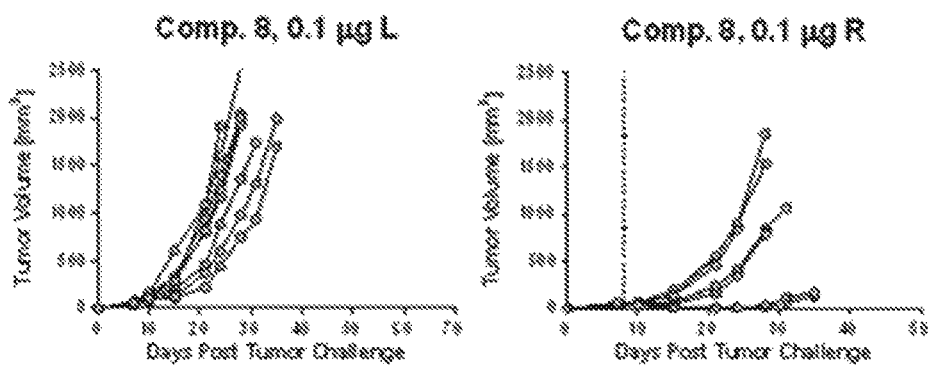
Figure 2C:
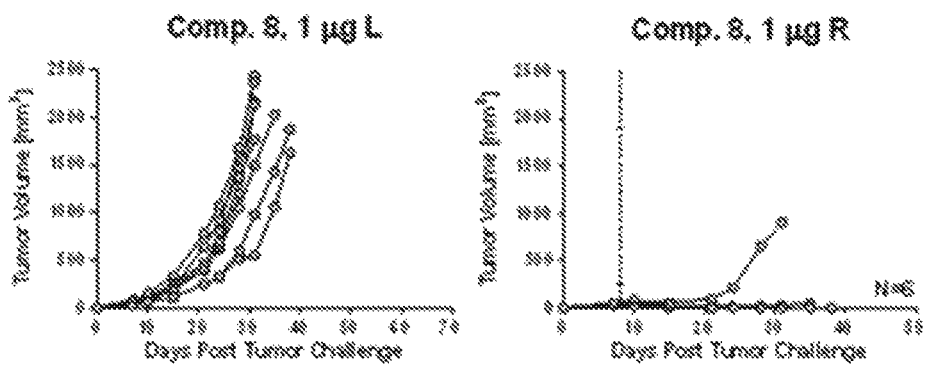
Figure 2D:
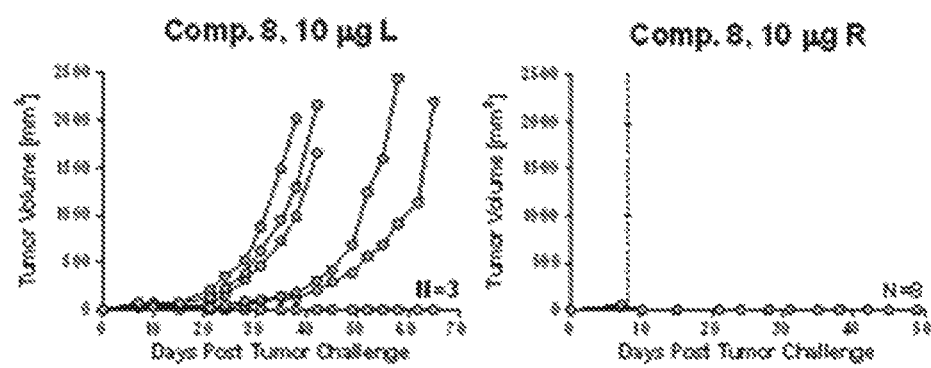
Figure 2E:
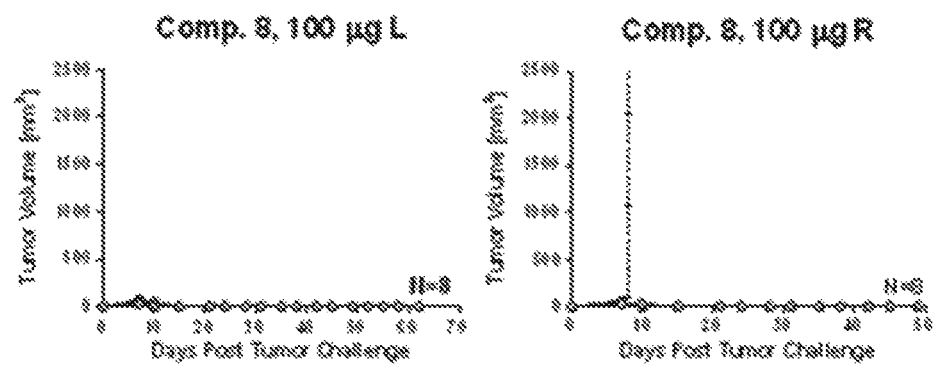

The present invention relates to 2'2'-RR-(3'F-A)(3'F-A) and the production and use thereof as an immune stimulator that activate DCs via a cytoplasmic receptor known as STING (Stimulator of Interferon Genes).

Conserved microbial structures known as Pathogen-Associated Molecular Patterns (PAMPs) are sensed by host cell Pattern Recognition Receptors (PRRs with germ-line encoded specificity), triggering a downstream signaling cascade resulting in the induction of cytokines and chemokines, and initiation of a specific adaptive immune response (Iwasaki and Medzhitov, Science 327, 291-5, 2010). How the innate immune system is engaged by PAMPs presented from an infectious agent shapes the development of an adaptive response appropriate to combat the invading pathogen from causing disease.

One objective in the design of immune modulators and adjuvants is to select defined PAMPs or synthetic molecules which activate designated PRRs and initiate a desired response. Adjuvants such as monophosphoryl lipid A (MPL) and CpG are microbial-derived PAMPs recognized by Toll-like receptors (TLRs), a class of PRRs that signal through MyD88 and TRIF adaptor molecules and mediate induction of NF-κB dependent proinflammatory cytokines (Pandey et. al., Cold Spring Harb Perspect Biol 2015:7: a016246). MPL (TLR-4 agonist) and CpG (TLR-9 agonist) are the most clinically advanced adjuvants, and are components of vaccines that are approved or pending approval by the FDA (Einstein et al., Human Vaccines, 5: 705-19, 2009; Ahmed et al., Nature Immunol. 12: 509-17, 2011). While TLRs present on the cell surface (e.g., TLR-4) and endosomes (e.g., TLR-9) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system can sense productively replicating pathogenic microbes by monitoring the cytosol (Vance et al., Cell Host & Microbe 6: 10-21, 2009). This provides a rationale for the use of agonists that activate PRRs comprising the cytosolic surveillance pathway and may be an effective strategy for the design of effective vaccines for eliciting cellular immunity, an immune correlate of protection against intracellular pathogens and therapeutic benefit in cancer.

Type I interferons (IFN-α, IFN-β) are the signature cytokines induced by two distinct TLR-independent cytosolic signaling pathways. In the first pathway, various forms of single-stranded and double-stranded (ds) RNA are sensed by RNA helicases, including retinoic acid-inducible gene I (RIG-I) and melanoma differentiation-associated gene 5 (MDA-5), and through the IFN-β promoter stimulator 1 (IPS-1) adaptor protein mediate phosphorylation of the IRF-3 transcription factor, leading to induction of IFN-β (Ireton and Gale, Viruses 3: 906-19, 2011). IPS-1$^{-/-}$ deficient mice have increased susceptibility to infection with RNA viruses. Sensors that signal through the IPS-1 pathway are directly targeted for inactivation by various viral proteins, demonstrating a requirement of this cytosolic host defense pathway to control productive virus infection. Synthetic dsRNA, such as polyinosinic:polycytidylic acid (poly (I:C) and poly ICLC, an analog that is formulated with poly L lysine to resist RNase digestion, is an agonist for both TLR3 and MDA5 pathways, is a powerful inducer of IFN-β, and is currently being evaluated in several diverse clinical settings (Caskey et al., J. Exp. Med. 208: 2357-77, 2011).

STING (Stimulator of Interferon Genes) is a central mediator for the second cytosolic pathway that triggers type 1 interferon, in response to sensing cytosolic double-stranded (ds) DNA from infectious pathogens or aberrant host cells (Danger Associated Molecular Patterns, DAMPS) (Barber, Immunol. Rev 243: 99-108, 2011). Alternatively known as TMEM173, MITA, ERIS, and MPYS, STING was discovered using cDNA expression cloning methods as a MyD88-independent host cell defense factor expressed in macrophages, dendritic cells (DCs) and fibroblasts was found to induce expression of IFN-β and NF-κB dependent pro-inflammatory cytokines in response to sensing cytoplasmic DNA, in response to infection with herpes simplex virus (Ishikawa and Barber, Nature 455: 674-79, 2008).

Cyclic dinucleotides (CDNs) have been studied as ubiquitous small molecule second messengers synthesized by bacteria which regulate diverse processes including motility and formation of biofilms (Romling et al., Micrb. Mol. Biol. Rev., 77: 1-52, 2013). CDNs are also a ligand for STING (Burdette et al., Nature 478: 515-18, 2011). In response to binding CDNs, STING activates signaling through the TBK-1/IRF-3 axis and NF-κB axis and induces the expression of IFN-β and other co-regulated genes (Burdette and Vance, Nat Immunol. 14: 19-26, 2013; McWhirter et al., J. Exp. Med. 206: 1899-1911, 2009). Cyclic (c)-di-AMP is secreted by multidrug resistance efflux pumps from the intracellular bacterium *Listeria monocytogenes* into the cytosol of infected host antigen presenting cells, and is correlated with $CD4^+$ and $CD8^+$ T cell-mediated protection in the mouse listeriosis model (Woodward et al., Science 328, 1703-05, 2010; Crimmins et al., Proc. Natl. Acad. Sci. USA 105: 10191-10196, 2008). Induction of IFN-β in Lm-infected macrophages is dependent upon activation of the STING signaling pathway, and the level of type I IFN induced by c-di-AMP in macrophages from MyD88$^{-/-}$ Trif$^{-/-}$ or C57BL/6 parental mice is indistinguishable (Leber et al., PLoS Pathog 4(1): e6. doi:10.1371, 2008; Witte et al., mBio 4: e00282-13, 2012). In contrast, IFN-β is not induced by CDNs in macrophages derived from goldenticket (gt) mice encoding a nonfunctional mutant STING protein (Sauer et al., Infect. Immun. 79: 688-94, 2011). The extracellular bacterium, *Vibrio cholera*, produces a hybrid c-GMP-AMP (cGAMP) molecule, which also induces the STING pathway (Davies et al., Cell 149: 358-70, 2012). The activation of innate immunity with these ubiquitous second messengers suggests that sensing CDNs may be integral to host defense against bacterial infection.

While STING was discovered as being the critical sensor for inducing the production of IFN-β in response to infection with herpes simplex virus, how the DNA from this viral pathogen was detected in the cytoplasm initially remained elusive. This conundrum was solved with the discovery of cyclic GMP-AMP synthase (cGAS), a host cell nucleotidyl transferase that directly binds dsDNA, and in response synthesizes a second messenger, cyclic GMP-AMP (cGAMP), which activates the STING pathway and induces IFN-β expression (Sun et al., Science 339: 786-91, 2013; Wu et al., Science 339: 826-30, 2013). Cells without a functional cGAS are unable to express IFN-β in response to stimulation with cytosolic DNA. It was later shown that cells expressing a particular STING allele were non-responsive to stimulation by CDNs, but responsive to stimulation with dsDNA in a cGAS-dependent and TLR9 (MyD88)-independent manner (Diner et. al., 2013). This observation was incompatible with a mechanism defined by cGAS synthesizing STING-activating CDN ligands in response to sensing cytosolic dsDNA. This apparent paradox was resolved by several independent investigators, who demonstrated that cGAS produces a non-canonical CDN (c-GMP-AMP; cGAMP) that activates STING alleles that are non-responsive to canonical CDNs (Civril et al., Nature 498: 332-37, 2013, Diner et al., 2013, Gao et al., 2013, Ablasser et al., Nature 498: 380-84, 2013, Kranzusch et al., Cell Reports 3: 1362-68, 2013, Zhang et al., Mol. Cell. 51: 226-35, 2013). cGAMP thus functions as a second messenger that binds to and activates STING. Unlike the CDN second messengers produced by bacteria, in which the two purine nucleosides are joined by a phosphate bridge with bis-(3',5') linkages, the internucleotide phosphate bridge in the cyclic-GMP-AMP synthesized by cGAS is joined by non-canonical 2',5' and 3',5' linkages (alternatively termed "mixed" linkages or ML), represented c[G(2',5')pA(3',5')p]. These 2',5'-3',5' molecules bind STING with nM affinity, some 300-fold better than bacterial c-di-GMP. Thus, it has been suggested that the 2',5'-3',5' molecules represent much more potent physiological ligands in terms of STING targeting. Zhang et al., 2013; see also, Xiao and Fitzgerald, Mol. Cell 51: 135-39, 2013. The differences in internucleotide phosphate bridge structures between CDNs produced by bacteria [canonical bis-(3',5') linkages] and by host cell cGAS (non-canonical 2',5' and 3',5' linkages) indicates that the STING receptor evolved to distinguish between CDNs produced by bacteria or by host cell cGAS.

Human STING has known polymorphisms, including alleles encoding histidine at position 232, which are refractory to canonical CDNs, but not non-canonical CDNs (Diner et al., Cell Reports, 3:1355-1361, 2013, Jin et al., Genes and Immunity, 12:263-9, 2011). Single nucleotide polymorphisms in the hSTING gene have been shown to affect the responsiveness to bacterial-derived canonical CDNs (Diner et al., 2013; Gao et al., Cell, 154:748-762, 2013; Conlon et. al., J. Immunol., 190:5216-5225, 2013). Five haplotypes of hSTING have been identified (WT, REF, HAQ, AQ and Q alleles), which vary at amino acid positions 71, 230, 232 and 293 (Jin et al., 2011; Yi et al., PLOS One 8(10):e77846, 2013). Cells expressing hSTING reportedly respond poorly to stimulation with bacterial CDNs cGAMP, c-di-AMP and c-di-GMP having bis-(3',5') linkages, but are responsive to the endogenously produced cGAS product, ML cGAMP (Diner et al., 2013). Therefore, the published literature indicates that for broad activation of all human STING alleles it is desirable that the CDN internucleotide phosphate bridge have a non-canonical, mixed linkage c[G(2',5')pA(3', 5')p] structure. Examples of cyclic purine dinucleotides are described in some detail in, e.g., U.S. Pat. Nos. 7,709,458 and 7,592,326; WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18: 5631 (2008). 2'2'-RR-(3'F-A) (3'F-A) as described herein, having bis-(2',5') linkages, demonstrates high potency and surprisingly shows less variation in binding to different allelic variants of hSTING than canonical and mixed linkage di-fluoro substituted CDNs such as 3'3'-RR-(2'F-A)(2'F-A) and 2'3'-RR-(3'F-A)(2'F-A), as well as the natural ligand 2'3'-(G)(A). Thus 2'2'-RR-(3'F-A)(3'F-A) provides a STING activating compound for therapeutic use that can be dosed more effectively independently of the allelic variation within a subject.

Native CDN molecules are sensitive to degradation by phosphodiesterases that are present in host cells, for example in antigen presenting cells, which take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-β), correlated with weaker vaccine potency, as defined by the magnitude of a measured antigen-specific immune response.

Definitions

As used herein, the following definitions shall apply unless otherwise indicated. The abbreviations used herein have their conventional meaning within the chemical and biological arts. The chemical structures set forth herein are constructed according to the standard rules of chemical valency known in the chemical arts.

Unless otherwise stated or depicted, 2'2'-RR-(3'F-A)(3'F-A) is meant to include the free base form or non-salt form, a pharmaceutically acceptable salt, pharmaceutically acceptable solvate, or pharmaceutically acceptable hydrate thereof. Unless otherwise stated or depicted, 2'2'-RR-(3'F-A)(3'F-A) depicted herein is also meant to include any tautomeric forms of the structure as within the scope of the invention. Exemplary tautomeric forms can be

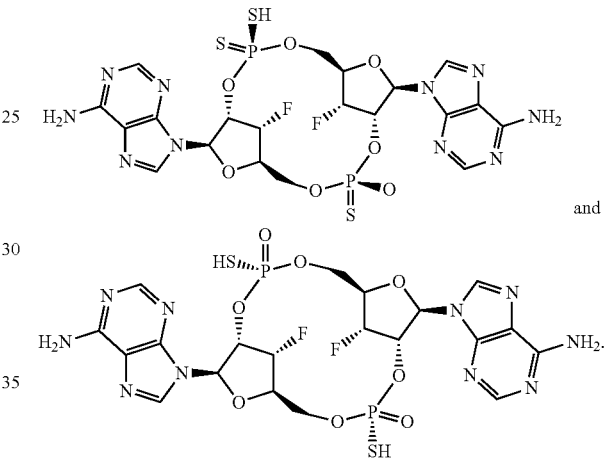

and

Additionally, unless otherwise stated, structures depicted herein are also meant to include compounds that differ only in the presence of one or more isotopically enriched atoms. For example, 2'2'-RR-(3'F-A)(3'F-A) having the structures as presented herein including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" or "co-administered" it is not meant to be implied that two or more agents be administered as a single composition. Although administration as a single composition is contemplated by the present invention, such agents may be delivered to a single subject as separate administrations, which may be at the same or different times, and which may be by the same route or different routes of administration. By "administered simultaneously" it is meant to be implied that two or more agents be administered at essentially the same time, although not necessarily administered as a single composition or by the same route of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) receptor can encompass GM-CSF, a mutant or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g., Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

By "an agent that enhances permeability" or "an agent that enhances uptake" as used herein as it relates to cell permeability or uptake of compound by cells, is an agent that enhances the permeability of a cell to a compound or enhances the uptake of a compound by the cell, either in vitro, or in vivo. The compound of the present invention, e.g., 2'2'-RR-(3'F-A)(3'F-A) as described herein can be compared to a reference compound in an in vitro cell based assay, wherein the assay may be performed with or without an agent, such as digitonin, or by electroporation, that allows for the compound to be taken up by the cell. The 2'2'-RR-(3'F-A)(3'F-A) as described herein is surprisingly active in such cell based assays without the need for such an agent that enhances permeability of the cell or enhances uptake of the compound by the cell, for example in the THP-1 cell assay as described herein in Example 5. Compositions comprising the 2'2'-RR-(3'F-A)(3'F-A) as described herein can be formulated without an agent that enhances permeability of the cell or enhances uptake of the compound by the cell, for example without a delivery vehicle that enhances permeability of the cell or enhances cellular uptake. Such additives or delivery vehicles include, without limitation, lipid or lipid-like adjuvants, liposomes, interbilayer cross-linked multilamellar vesicles, nanocarriers, nanoparticles and the like, such as nanoparticles comprising Poly(lactic acid) (PLA), Poly(glycolic acid) (PGA), and/or their copolymers such as biodegradable poly(D,L-lactic-co-glycolic acid) [PLGA]-based or poly anhydride-based nanoparticles or microparticles.

By "substantially purified" with regard to the compound of the present invention, e.g., 2'2'-RR-(3'F-A)(3'F-A) is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or a combination thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4 M^{-1}$ and about $10^8 M^{-1}$. Affinity is calculated as $K_B=1/K_d=k_{on}/k_{off}$ ($k_{off}$ is the dissociation rate constant, $K_{on}$ is the association rate constant, $K_B$ is the equilibrium binding constant, and $K_d$ is the equilibrium dissociation constant or $K_D$).

Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot Affinity measurement by Scatchard analysis is well known in the art. See, e.g., van Erp et al., *J. Immunoassay* 12: 425-43, 1991; Nelson and Griswold, *Comput Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" or "individual" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

Cyclic Dinucleotides

Prokaryotic as well as eukaryotic cells use various small molecules for cell signaling and intra- and intercellular communication. Cyclic purine nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyzed by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. Burdette et al., Nature 478: 515-18, 2011 demonstrated that STING binds directly to cyclic diguanylate monophosphate, but not to other unrelated nucleotides or nucleic acids.

2'2'-RR-(3'F-A)(3'F-A) of the present invention as described herein is a potent STING agonist for all known hSTING variants. It has been shown for both canonical and mixed link CDNs that substitution with mono or di-fluoro at the 2'OH or 3'OH positions of these CDNs improves their potency against hSTING. Surprisingly, the di-fluoro substitution of 2'2'-RR-(3'F-A)(3'F-A) provides a potent hSTING agonist with less variability across WT, HAQ and REF alleles than either the analogous di-fluoro compound of the canonical CDN, 3'3'-RR-(2'F-A)(2'F-A), or the mixed link CDN 2'3'-RR-(3'F-A)(2'F-A), which allows for more consistent dosing of 2'2'-RR-(3'F-A)(3'F-A) and better safety profile independent of the subject's hSTING variant. The properties of these CDN compounds are demonstrated in Examples 4 and 5 below. The $T_m$ shift in a DSF assay is used to assess hSTING binding in WT, HAQ or REF variants or an ITC assay is used to assess hSTING binding in WT or REF in Example 4. The EC50 in a THP1 cell assay in the absence of digitonin is used to assess the cellular activity against hSTING HAQ in Example 5.

2'2'-RR-(3'F-A)(3'F-A) of the present invention as described herein comprises phosphorothioate in both internucleotide bonds, in which one of the nonbridging oxygens is replaced by a sulfur. The sulfurization of the internucleotide bond dramatically reduces the action of endo-and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage is inherently chiral. The skilled artisan will recognize that the phosphates in this structure may each exist in R or S forms. Thus, Rp,Rp, Sp,Sp, Sp,Rp, and Rp,Sp forms are possible. 2'2'-RR-(3'F-A)(3'F-A) of the present invention is the Rp,Rp form.

The term "substantially pure" as used herein with regard to 2'2'-RR-(3'F-A)(3'F-A) refers to the Rp,Rp form which is at least 75% pure relative to other possible stereochemistries at the chiral phosphorus centers indicated in 2'2'-RR-(3'F-A)(3'F-A) as described herein. By way of example, "substantially pure 2'2'-RR-(3'F-A)(3'F-A)" would be at least 75% pure with regard to the Rp,Sp and Sp,Sp forms, i.e., with respect to 2'2'-RS-(3'F-A)(3'F-A) and 2'2'-SS-(3'F-A)(3'F-A). In preferred embodiments, a substantially pure 2'2'-RR-(3'F-A)(3'F-A) is at least 85% pure, at least 90% pure, at least 95% pure, at least 97% pure, and at least 99% pure. Similarly, any of the other isomers can be substantially pure with respect to the other three isomers, e.g., substantially pure Rp,Rp form relative to the Rp,Sp and Sp,Sp forms. Such a substantially pure preparation may also include other components as described hereinafter that are advantageous for patient treatment, e.g., in combination with other agents, excipients, and the like, provided that all 2'2'-RR-(3'F-A)(3'F-A) within the preparation is substantially pure RR stereochemistry at these chiral centers.

The compound of the present invention, such as 2'2'-RR-(3'F-A)(3'F-A) and compositions thereof described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the 2'2'-RR-(3'F-A)(3'F-A) and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The compound of the present invention, such as 2'2'-RR-(3'F-A)(3'F-A) and compositions thereof described herein may be administered before, after, and/or simultaneously with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisole, vaccinia virus, Bacille Calmette-Guerin (BCG), liposomes, alum, Freund's complete or incomplete adjuvant, detoxified endotoxins, mineral oils, surface active substances such as lipolecithin, lecithins, lysolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of Quillaja saponaria and Corynebacterium parvum (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g., same formulation) such that they are administered at the same time by the same route of administration.

Because of the adjuvant properties of 2'2'-RR-(3'F-A)(3'F-A), its use may also be combined with other therapeutic modalities including other vaccines, adjuvants, antigen, antibodies, and immune modulators. Examples are provided below.

Adjuvants

In addition to the compound of the present invention, such as 2'2'-RR-(3'F-A)(3'F-A) and compositions thereof described herein, the compositions or methods of the present invention may further comprise one or more additional substances which, because of their nature, can act to stimulate or otherwise utilize the immune system to respond to the cancer antigens present on the targeted tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), and/or pathogen-associated molecular patterns ("PAMPs"). Examples of PAMPs include lipoproteins, lipopolypeptides, peptidoglycans, zymosan, lipopolysaccharide, neisserial porins, flagellin, profilin, galactoceramide, galactosylceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

Immune Checkpoint Inhibitors

The compound of the present invention, such as 2'2'-RR-(3'F-A)(3'F-A) as described herein can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist. In some embodiments, the immune checkpoint inhibitor is selected from the group consisting of an anti-CTLA-4 antibody, an anti-PD-1 antibody, an anti-Tim-3 antibody, an anti-Vista antibody, an anti-BTLA antibody, an anti-B7-H3 antibody, an anti-CD70 antibody, an anti-LAG-3 antibody, or an anti-TIGIT antibody.

The compound of the present invention, such as 2'2'-RR-(3'F-A)(3'F-A) as described herein can be used in combination with CTLA-4 pathway antagonists. In some embodiments, the combination is used to treat a solid tumor or a hematologic malignancy. CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma. In some embodiments, the CTLA-4 pathway antagonist is an anti-CTLA-4 antibody molecule selected from the group consisting of tremelimumab and ipilimumab. In some embodiments, the anti-CTLA-4 antibody is an anti-CTLA-4 antibody as disclosed in e.g., U.S. Pat. No. 5,811,097.

Ipilimumab (Yervoy™, a CTLA-4 antibody, also known as MDX-010, CAS No. 477202-00-9) and tremelimumab (IgG2 monoclonal antibody available from Pfizer, formerly known as ticilimumab, CP-675,206) are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1 (PD-1), B and T lymphocyte attenuator, transforming growth factor beta β, interleukin-10, and vascular endothelial growth factor.

In some embodiments, the compound of the present invention, such as 2'2'-RR-(3'F-A)(3'F-A) as described herein can be used in combination with an anti-CTLA-4 antibody and an anti-PD-1 antibody. In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

The compound of the present invention, such as 2'2'-RR-(3'F-A)(3'F-A) as described herein can be used in combination with PD-1 pathway antagonists. In some embodiments, the combination is used to treat a solid tumor or a hematologic malignancy. PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. Anti-PD-1 antibody molecules (e.g., Nivolumab (Opdivo™), pembrolizumab (Keytruda™) and pidilizumab), and AMP-224 have been reported in the literature to be examples of PD-1 pathway blockers which may find use in the present invention. In some embodiments, the PD-1 pathway antagonist is an anti-PD-1 antibody molecule selected from the group consisting of nivolumab, pembrolizumab or pidilizumab.

In some embodiments, the anti-PD-1 antibody is nivolumab. Alternative names for nivolumab include MDX-1106, MDX-1106-04, ONO-4538, or BMS-936558. In some embodiments, the anti-PD-1 antibody is nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is nivolumab, and having a sequence disclosed herein (or a sequence substantially identical or similar thereto, e.g., a sequence at least 85%, 90%, 95% identical or higher to the sequence specified).

The heavy chain amino acid sequence of nivolumab is as follows:

(SEQ ID NO: 1)
QVQLVESGGGVVQPGRSLRLDCKASGITFSNSGMHWVRQAPGKGLETAWAV

IWYDGSKRYYADSVKGRFTISRDNSKNTLFLQMNSLRAEDTAVYYCATNDD

YTNGQGTLVTVSSASTKGPSVFPLAPCSRSTSESTAALGCLVKDYFPEPVT

VSTAMSGALTSGVHTFPAVLQSSGLYSLSSVVTVPSSSLGTKTYTCNVDHK

PSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTKN

QVSLTCLVKGFYPSDIAVEWESNGQPENNYKTTPPVLDSGSFFLYSRLTV

DKSRWQEGNVESCSVMHEALHNHYTQKSLSLSLGK

The light chain amino acid sequence of nivolumab is as follows:

(SEQ ID NO: 2)
EIVLTQSPATLSLSPGERATLSCRASQSVSSYLAWYQQKPGQAPRLLIYDA

SNRATGIPARFSGSGSGTDFTLTISSLEPEDFAVYYCQQSSNWPRTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

In some embodiments, the anti-PD-1 antibody is pembrolizumab. Pembrolizumab (also referred to as lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England *Journal of Medicine* 369 (2): 134-44, U.S. Pat. No. 8,354,509 and WO2009/114335. In one embodiment, the inhibitor of PD-1 is pembrolizumab, and having a sequence disclosed herein (or a sequence substantially identical or similar thereto, e.g., a sequence at least 85%, 90%, 95% identical or higher to the sequence specified).

The heavy chain amino acid sequences of pembrolizumab is as follows:

(SEQ ID NO: 3)
QVQLVQSGVE VKKPGASVKV SCKASGYTFT NYYMYWVRQA PGQGLEWMGG 50

INPSNGGTNF NEKFKNRVTL TTDSSTTTAY MELKSLQFDD TAVYYCARRD 100

YRFDMGFDYW GQGTTVTVSS ASTKGPSVFP LAPCSRSTSE STAALGCLVK 150

DYFPEPVTVS WNSGALTSGV HTFPAVLQSS GLYSLSSVVT VPSSSLGTKT 200

YTCNVDHKPS NTKVDKRVES KYGPPCPPCP APEFLGGPSV FLFPPKPKDT 250

LMISRTPEVT CVVVDVSQED PEVQFNWYVD GVEVHNAKTK PREEQFNSTY 300

RVVSVLTVLH QDWLNGKEYK CKVSNKGLPS SIEKTISKAK GQPREPQVYT 350

LPPSQEEMTK NQVSLTCLVK GFYPSDIAVE WESNGQPENN YKTTPPVLDS 400

DGSFFLYSRL TVDKSRWQEG NVFSCSVMHE ALHNHYTQKS LSLSLGK 447

The light chain amino acid sequences of pembrolizumab is as follows:

(SEQ ID NO: 4)
EIVLTQSPAT LSLSPGERAT LSCRASKGVS TSGYSYLHWY QQKPGQAPRL 50

LIYLASYLES GVPARFSGSG SGTDFTLTIS SLEPEDFAVY YCQHSRDLPL 100

TFGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200

THQGLSSPVT KSFNRGEC 218

In some embodiments, the anti-PD-1 antibody is pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

In some embodiments, the anti-PD-1 antibody is AMP 514 (Amplimmune), or an anti-PD-1 antibody as disclosed in U.S. Pat. No. 8,609,089, US 2010028330, and/or US 20120114649.

In some embodiments the PD-1 pathway antagonist is an anti-PD-1 antibody molecule disclosed in US 2015/0210769, published on Jul. 30, 2015, and entitled "Antibody Molecules to PD-1 and Uses Thereof".

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described in US 2015/0210769, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 therein, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1 therein.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-PD-1 antibody molecule includes: (a) a heavy chain variable region (VH) comprising a VHCDR1 amino acid sequence of SEQ ID NO: 4; a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; (b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769; (c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769.

In another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each as disclosed in Table 1 of US 2015/0210769.

In some embodiments the PD-1 pathway antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342) is a PD-L2 Fc fusion soluble receptor that blocks the interaction between PD-1 and B7-H1.

In some embodiments the PD-1 pathway antagonist is a PD-L1 or PD-L2 inhibitor. In some embodiments the PD-L1 or PD-L2 inhibitor is an anti-PD-L1 antibody or an anti-PD-L2 antibody.

In some embodiments, the PD-L1 inhibitor is an anti-PD-L1 antibody. Exemplary non-limiting combinations and uses of the anti-PD-L1 antibody molecules are disclosed in US 2016/0108123, published Apr. 21, 2016, entitled "Antibody Molecules to PD-L1 and Uses Thereof".

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1. In another embodiment, the anti-PD-L1 antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195, each disclosed in Table 1 of US 2016/0108123.

In some embodiments, the anti-PD-L1 inhibitor is chosen from YW243.55.570, MPDL3280A, MEDI-4736, MSB-0010718C, or MDX-1105. In some embodiments, the PD-L1 inhibitor is an anti-PD-L1 antibody MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed therein (or a sequence substantially identical or similar thereto, e.g., a sequence at least 85%, 90%, 95% identical or higher to the sequence specified).

The heavy chain amino acid sequence (SEQ ID NO: 24 as disclosed in WO2013/079174) of MSB0010718C includes at least the following:

```
                                           (SEQ ID NO: 5)
EVQLLESGGGLVQPGGSLRLSCAASGFTFSSYIMMWVRQAPGKGLEWVSSI

YPSGGITFYADKGRFTISRDNSKNTLYLQMNSLRAEDTAVYYCARIKLGTV

TTVDYWGQGTLVTVSS
```

The light chain amino acid sequence (SEQ ID NO: 25 as disclosed in WO2013/079174) of MSB0010718C includes at least the following:

```
                                           (SEQ ID NO: 6)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVL
```

In one embodiment, the PD-L1 inhibitor is YW243.55.S70. The YW243.55.S70 antibody is an anti-PD-L1 antibody as described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DClg; Amplimmune; e.g., disclosed in WO2010/027827 and WO2011/066342

The compound of the present invention, such as 2'2'-RR-(3'F-A)(3'F-A) as described herein can be used in combination with TIM-3 pathway antagonists. In some embodiments, the combination is used to treat a solid tumor or a hematologic malignancy. In some embodiments, the TIM-3 pathway antagonist is an anti-TIM-3 antibody. In some embodiments, anti-TIM-3 antibody molecules are disclosed in US 2015/0218274, published on Aug. 6, 2015, entitled "Antibody Molecules to TIM-3 and Uses Thereof".

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, AB TIM3-hum16, ABTIM3-hum17, AB TIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described in US 2015/0218274, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Table 1-4 therein.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein.

In one embodiment, the anti-TIM-3 antibody molecule includes: (a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274.

In some embodiments, the TIM-3 pathway antagonist is an anti-TIM-3 antibody as disclosed in U.S. Pat. No. 8,552,156, WO 2011/155607, EP 2581113 or U.S Publication No.: 2014/044728.

The compound of the present invention, such as 2'2'-RR-(3'F-A)(3'F-A) as described herein can be used in combination with LAG-3 pathway antagonists. In some embodiments, the combination is used to treat a solid tumor or a hematologic malignancy. In some embodiments, the LAG-3 pathway antagonist is an anti-LAG-3 antibody. In some embodiments the anti-LAG-3 antibody molecules are disclosed in US 2015/0259420, filed Mar. 13, 2015, entitled "Antibody Molecules to LAG-3 and Uses Thereof".

In one embodiment, the anti-LAG-3antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each as disclosed in Table 1 of US 2015/0259420.

In another embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each as disclosed in Table 1 of US 2015/0259420.

In one embodiment, the anti-LAG-3 antibody molecule comprises the VHCDR1 amino acid sequence of SEQ ID NO: 1 as disclosed in Table 1 of US 2015/0259420. In another embodiment, the anti-LAG-3 antibody molecule comprises the VHCDR1 amino acid sequence of SEQ ID NO: 4 as disclosed in Table 1 of US 2015/0259420. In yet another embodiment, the anti-LAG-3 antibody molecule comprises the VHCDR1 amino acid sequence of SEQ ID NO: 286, as disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

T-cell Receptor Agonists

The compound of the present invention, such as 2'2'-RR-(3'F-A)(3'F-A) as described herein can be used in combination with a T-cell receptor agonist, such as a CD28 agonist, an OX40 agonist, a GITR agonist, a CD137 agonist, a CD27 agonist or an HVEM agonist.

The compound of the present invention, such as 2'2'-RR-(3'F-A)(3'F-A) as described herein can be used in combination with a CD27 agonist. Exemplary CD27 agonists include an anti-CD27 agonistic antibody, e.g., as described in PCT Publication No. WO 2012/004367.

The compound of the present invention, such as 2'2'-RR-(3'F-A)(3'F-A) as described herein can be used in combination with a GITR agonist. In some embodiments, the combination is used to treat a solid tumor or a hematologic malignancy. Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479. In some embodiments, the GITR agonist is GWN323 (NVS), BMS-986156, MK-4166 or MK-1248 (Merck), TRX518 (Leap Therapeutics), INCAGN1876 (Incyte/Agenus), AMG 228 (Amgen) or INBRX-110 (Inhibrx). In one embodiment, the GITR agonist is an anti-GITR antibody molecule. In one embodiment, the GITR agonist is an anti-GITR antibody molecule as described in WO 2016/057846, published on Apr. 14, 2016, entitled "Compositions and Methods of Use for Augmented Immune Response and Cancer Therapy," incorporated by reference with respect to such GITR agonists.

In one embodiment, the compound of the present invention, such as 2'2'-RR-(3'F-A)(3'F-A) as described herein is used in combination with a GITR agonist used in combination with a PD-1 inhibitor, e.g., as described in WO2015/026684.

In another embodiment, the compound of the present invention, such as 2'2'-RR-(3'F-A)(3'F-A) as described herein is used in combination with a GITR agonist used in combination with a TLR agonist, e.g., as described in WO2004060319, and International Publication No.: WO2014012479.

TLR Agonists

The compound of the present invention, such as 2'2'-RR-(3'F-A)(3'F-A) as described herein can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g., CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the compound of the present invention, such as 2'2'-RR-(3'F-A)(3'F-A) and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

The compound of the present invention, such as 2'2'-RR-(3'F-A)(3'F-A) as described herein can be used in combination with therapeutic antibodies. In some embodiments, the mechanism of action of the therapeutic antibody is Antibody-Dependent Cell-Mediated Cytotoxicity (ADCC)/phagocytosis (ADCP). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the compound of the present invention, such as 2'2'-RR-(3'F-A)(3'F-A).

Muromonab-CD3: Used to prevent acute rejection of organ, e.g., kidney, transplants. The humanized versions show promise in inhibiting the autoimmune destruction of beta cells in Type 1 diabetes mellitus.

Infliximab (Remicade®) and adalimumab (Humira®): Bind to tumor necrosis factor-alpha (TNF-α). Used in some inflammatory diseases such as rheumatoid arthritis, psoriasis, Crohn's disease.

Omalizumab (Xolair®). Binds to IgE thus preventing IgE from binding to mast cells. Used against allergic asthma.

Daclizumab (Zenapax®). Binds to part of the IL-2 receptor exposed at the surface of activated T cells. Used to prevent acute rejection of transplanted kidneys.

Rituximab (trade name=Rituxan®). Binds to the CD20 molecule found on most B-cells and is used to treat B-cell lymphomas.

Ibritumomab (trade name=Zevalin®). This is a monoclonal antibody against the CD20 molecule on B cells (and lymphomas) conjugated to isotopes. Given to the lymphoma patient supplemented with Rituxan.

Tositumomab (Bexxar®). This is a conjugate of a monoclonal antibody against CD20 and the radioactive isotope iodine-131 (I311).

Cetuximab (Erbitux®). Blocks HER1, a receptor for epidermal growth factor (EGF) that is found on some tumor cells (some breast cancers, lymphomas).

Trastuzumab (Herceptin®). Blocks HER2, a growth factor receptor over-expressed in some 20% of breast cancers.

Brentuximab Vedotin (Adcetris®). A conjugate of a monoclonal antibody that binds CD30, a cell-surface molecule expressed by the cells of some lymphomas but not found on the normal stem cells needed to repopulate the bone marrow.

Alemtuzumab (Campath-1H®). Binds to CD52, a molecule found on lymphocytes and depletes both T cells and B cells. Has produced complete remission of chronic lymphocytic leukemia and shows promise in preventing rejection of kidney transplants.

Lym-1 (Oncolym®). Binds to the HLA-DR-encoded histocompatibility antigen that can be expressed at high levels on lymphoma cells.

Ipilimumab (Yervoy®) that acts to enhance the body's own immune response to tumors.

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Used for the treatment of colorectal cancers.

Abciximab (ReoPro®). Inhibits the clumping of platelets by binding the receptors on their surface that normally are linked by fibrinogen. Helpful in preventing reclogging of the coronary arteries in patients who have undergone angioplasty.

Additional therapeutic antibodies that may be used in combination with the compound of the present invention, such as 2'2'-RR-(3'F-A)(3'F-A) as described herein include a prolactin receptor (PRLR) inhibitor, e.g., as disclosed in U.S. Pat. No. 7,867,493, a HERS inhibitor, e.g., as disclosed in PCT Publication No. WO 2012/022814, an EGFR2 and/or EGFR4 inhibitor, e.g., as disclosed in PCT Publication No. WO 2014/160160, an M-CSF inhibitor, e.g., as disclosed in PCT Publication No. WO 2004/045532, an anti-APRIL antibody, e.g., as disclosed in U.S. Pat. No. 8,895,705, or an anti-SIRPα antibody e.g., as disclosed in U.S. Pat. No. 8,728,476, WO2015138600 and US20140242095, an anti-CD47 antibody, e.g., as disclosed in U.S. Pat. No. 8,562,997.

In one embodiment, the combination includes, e.g., a combination comprising a compound of the present invention, such as 2'2'-RR-(3'F-A)(3'F-A) as described herein, used in combination with a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, the compound of the present invention, such as 2'2'-RR-(3'F-A)(3'F-A) is used in combination with human monoclonal antibody molecule (Compound A26) described in U.S. Pat. No. 7,867,493 to treat a disorder such as, a cancer, a prostate cancer, or a breast cancer.

In another embodiment, the combination includes, e.g., a combination comprising a compound of the present invention, such as 2'2'-RR-(3'F-A)(3'F-A) as described herein, used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, the compound of the present invention, such as 2'2'-RR-(3'F-A)(3'F-A) is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer. In some embodiments, Compound A31 is a human monoclonal antibody molecule. In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination includes, e.g., a combination comprising a compound of the present invention, such as 2'2'-RR-(3'F-A)(3'F-A) as described herein, used in combination with an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425 as described therein), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, the compound of the present invention, such as 2'2'-RR-(3'F-A)(3'F-A) is used in combination with Compound A32, or in further combination with a compound as described in Table 2 herein, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer. In some embodiments, Compound A32 is an antibody molecule drug conjugate against an FGFR2 and/or FGFR4, e.g., mAb 12425.

In another embodiment, the combination includes, e.g., a combination comprising a compound of the present invention, such as 2'2'-RR-(3'F-A)(3'F-A) described herein, used in combination with an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, the compound of the present invention, such as 2'2'-RR-(3'F-A)(3'F-A) is used in combination with Compound A33, or a compound as described in PCT Publication No. WO 2004/045532, to treat a disorder such as a cancer, a prostate cancer, a breast cancer, or pigmented villonodular synovitis (PVNS). In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833 describes suitable liposomal preparations. Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammonium propane, and nod-like receptor agonists. Advantageously, these liposomal formulations can be used to deliver the compound of the present invention, such as 2'2'-RR-(3'F-A)(3'F-A) and compositions thereof described herein in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, Liposome Methods and Protocols (Methods in Molecular Biology), Humana Press, 2002; Gregoriadis, Liposome Technology, $3^{rd}$ Edition, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-((22, 2004; Nanomedicine: Nanotechnology, Biology and Medicine 1:22-30, 2005; Din et al., International Journal of Nanomedicine, 12:7291-7309, 2017, the disclosures of which are hereby incorporated by reference as it relates to nanoparticles and nanocarriers.

Chemotherapeutic Agents

In additional embodiments of the methods described herein, the compound of the present invention, such as 2'2'-RR-(3'F-A)(3'F-A) as described herein is used in combination with chemotherapeutic agents (e.g., small molecule pharmaceutical compounds). Thus the methods further involve administering to the subject an effective amount of one or more chemotherapeutic agents as an additional treatment or a combination treatment. In certain embodiments the one or more chemotherapeutic agents is selected from the group consisting of an indoleamine 2,3-dioxygenase (IDO 1) inhibitor (e.g., epacadostat and navoximod), abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl- L-valyl-L-proly-1-Lproline-t-butylamide (SEQ ID NO: 21), cachectin, cemadotin, chlorambucil, cyclophosphamide, 3',4'-didehydro-4'-deoxy-8'-norvin-caleukoblastine, docetaxel, doxetaxel, cyclophosphamide, carboplatin, carmustine, cisplatin, cryptophycin, cyclophosphamide, cytarabine, dacarbazine (DTIC), dactinomycin, daunorubicin, decitabine, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), enzalutamide, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, estramustine phosphate, tamoxifen, tasonermin, taxol, tretinoin, vinblastine, vincristine, vindesine sulfate, and vinflunine.

In additional embodiments of the methods described herein, a compound of the present invention, such as 2'2'-RR-(3'F-A)(3'F-A) as described herein is used in combination with chemotherapeutic agents and/or additional agents for treating the indications as described in the methods herein. In some embodiments, the compound of the present invention, such as 2'2'-RR-(3'F-A)(3'F-A) as described herein is used in combination with one or more agents selected from the group consisting of sotrastaurin, nilotinib, 5-(2,4-dihydroxy-5-isopropylphenyl)-N-ethyl-4-(4-(morpholinomethyl)phenypisoxazole-3-carboxamide, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl)amino)pyrimidin-4-yl)-1-methylurea, 8-(2,6-difluoro-3,5-dimethoxyphenyl)-N-(4-((dimethylamino)methyl)-1H-imidazol-2-yl)quinoxaline-5-carboxamide, (S)-N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl(((1R,4S)-4-(4-methyl-3-oxopiperazin-1-yl)cyclohexyl)methyDamino)phenyl)-1,2-dihydroisoquinolin-3(4H)-one, deferasirox, letrozole, (4S,5R)-3-(2'-amino-2-morpholino-4'-(trifluoromethyl)-[4,5$^1$-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolinamide, imatinib mesylate, 2-fluoro-N-methyl-4-(7-(quinolin-6-ylmethypimidazo[1,2-b][1,2,4]triazin-2-yl)benzamide, ruxolitinib, panobinostat, osilodrostat, (S)-N-((S)-1-cyclohexyl-2-((S)-2-(4-(4-fluorobenzoyl) thiazol-2-yl)pyrrolidin-1-yl)-2-oxoethyl)-2-(methylamino)propanamide, (S)-N-((S)-1-cyclohexyl-24 (S)-2-(4-(4-fluorobenzoyl)thiazol-2-yl)pyrrolidin-1-yl)-2-oxoethyl)-2-(methylamino)propanamide, ceritinib, 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide, midostaurin, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine, pasireotide diaspartate, (R,E)-N-(7-chloro-1-(1-(4-(dimethylamino)but-2-enoyDazepan-3-yl)-1H-benzo[d]imidazol-2-yl)-2-methylisonicotinamide, N$^6$-(2-isopropoxy-5-methyl-4-(1-methylpiperidin-4-yl)phenyl)-N$^4$-(2-(isopropylsulfonyl)phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl) piperidin-1-yl)thietane 1,1-dioxide, 5-chloro-N$^2$-(2-fluoro-5-methyl-4-(1-(tetrahydro-2H-pyran-4-yl)piperidin-4-yl) phenyl)-N$^4$-(5-methyl-1H-pyrazol-3-yl)pyrimidine-2,4-diamine, 5-chloro-N2-(4-(1-ethylpiperidin-4-yl)-2-fluoro-5-methylphenyl)-N$^4$-(5-methyl-1H-pyrazol-3-yl)pyrimidine-2,4-diamine, valspodar, and vatalanib succinate.

In one embodiment, the combination includes, e.g., a combination comprising a compound of the present invention, such as 2'2'-RR-(3'F-A)(3'F-A) as described herein, used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, the compound of the present invention, such as 2'2'-RR-(3'F-A)(3'F-A) is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis. In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination includes, e.g., a combination comprising a compound of the present invention, such as 2'2'-RR-(3'F-A)(3'F-A) as described herein, used in combination with a BCR-ABL inhibitor, TASIGNA (Compound A2, nilotinib), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, the compound of the present invention, such as 2'2'-RR-(3'F-A)(3'F-A) is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension. In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the combination includes, e.g., a combination comprising a compound of the present invention, such as 2'2'-RR-(3'F-A)(3'F-A) as described herein, used in combination with an HSP90 inhibitor, such as a compound disclosed in PCT Publication No. WO 2010/060937 or WO 2004/072051, to treat a disorder, e.g., a disorder described herein. In one embodiment, the HSP90 inhibitor is a compound disclosed in PCT Publication No. WO 2010/060937 or WO 2004/072051. In one embodiment, the compound of the present invention, such as 2'2'-RR-(3'F-A)(3'F-A) is used in combination with a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination includes, e.g., a combination comprising a compound of the present invention, such as 2'2'-RR-(3'F-A)(3'F-A) as described herein, used in combination with an inhibitor of PI3K and/or mTOR, such as 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41) or a compound disclosed in PCT Publication No. WO 2006/122806, to treat a disorder, e.g., a disorder described herein. In one embodiment, the PI3K and/or mTOR inhibitor is 8-(6-Methoxy-pyridin-3-yl)-3-methyl-1-(4-piperazin-1-yl-3-trifluoromethyl-phenyl)-1,3-dihydro-imidazop,5-c]quinolin-2-one (Compound A41) or a compound disclosed in PCT Publication No. WO 2006/122806. In one embodiment, the compound of the present invention, such as 2'2'-RR-(3'F-A)(3'F-A) is used in combination with 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41) or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination includes, e.g., a combination comprising a compound of the present invention, such as 2'2'-RR-(3'F-A)(3'F-A) as described herein, used in combination with an FGFR inhibitor, such as a compound disclosed in U.S. Pat. No. 8,552,002, to treat a disorder, e.g., a disorder described herein. In one embodiment, the FGFR inhibitor is a compound disclosed in U.S. Pat. No. 8,552,002. In one embodiment, the compound of the present invention, such as 2'2'-RR-(3'F-A)(3'F-A) is used in combination with a compound as described in U.S. Pat. No. 8,552,002, to treat a disorder such as a digestive/gastrointestinal cancer, a hematological cancer, or a solid tumor. In one embodiment, the FGFR inhibitor is administered at a dose of about 100-125 mg (e.g., per day), e.g., about 100 mg or about 125 mg.

In another embodiment, the combination includes, e.g., a combination comprising a compound of the present invention, such as 2'2'-RR-(3'F-A)(3'F-A) as described herein, used in combination with a PI3K inhibitor, such as a compound disclosed in PCT Publication No. WO 2007/084786, to treat a disorder, e.g., a disorder described herein. In one embodiment, the PI3K inhibitor is a compound disclosed in PCT Publication No. WO 2007/084786. In one embodiment, the compound of the present invention, such as 2'2'-RR-(3'F-A)(3'F-A) is used in combination with a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer. In one embodiment, the PI3K inhibitor is administered ata dose of about 100 mg (e.g., per day).

In another embodiment, the combination includes, e.g., a combination comprising a compound of the present invention, such as 2'2'-RR-(3'F-A)(3'F-A) as described herein, used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386, to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yOquinoxaline-5-carboxamide (Compound A7) or a compound disclosed in PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yOquinoxaline-5-carboxamide (Compound A7). In one embodiment, the compound of the present invention, such as 2'2'-RR-(3'F-A)(3'F-A) is used in combination with 8-(2,6-difluoro-3,5-dimethoxyphenyl)-N-(4-((dimethylamino)methyl)-1H-imidazol-2-yOquinoxaline-5-carboxamide (Compound A7), or a compound disclosed in PCT Publication No. WO 2009/141386, to treat a disorder such as a cancer characterized by angiogenesis. In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment the combination includes, e.g., a combination comprising a compound of the present invention, such as 2'2'-RR-(3'F-A)(3'F-A) as described herein, used in combination with a PI3K inhibitor, (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082, to treat a disorder, e.g., a disorder described herein. In one embodiment, the PI3K inhibitor is (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, the compound of the present invention, such as 2'2'-RR-(3'F-A)(3'F-A) is used in combination with (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer. In one embodiment, the PI3K inhibitor or (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination includes, e.g., a combination comprising a compound of the present invention, such as 2'2'-RR-(3'F-A)(3'F-A) as described herein, used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, the compound of the present invention, such as 2'2'-RR-(3'F-A)(3'F-A) is used in combination with a compound disclosed in PCT Publication No. WO 2010/149755, to treat prostate cancer.

In another embodiment, the combination includes, e.g., a combination comprising a compound of the present invention, such as 2'2'-RR-(3'F-A)(3'F-A) as described herein, used in combination with an HDM2 inhibitor, (S)-1-(4-chlorophenyl)-7-isopropoxy-6-methoxy-2-(4-(methyl(((1R,4S)-4-(4-methyl-3-oxopiperazin-1-yl)cyclohexyl)methypamino)phenyl)-1,2-dihydroisoquinolin-3(4H)-one (Compound A10) or a compound disclosed in PCT Publication No. WO 2011/076786, to treat a disorder, e.g., a disorder described herein). In one embodiment, the HDM2 inhibitor is (S)-1-(4-chlorophenyl)-7-isopropoxy-6-methoxy-2-(4-(methyl(((1R,4S)-4-(4-methyl-3-oxopiperazin-1-yl)cyclohexyl)methypamino)phenyl)-1,2-dihydroisoquinolin-3(4H)-one (Compound A10) or a compound disclosed in PCT Publication No. WO 2011/076786. In one embodiment, the compound of the present invention, such as 2'2'-RR-(3'F-A)(3'F-A) is used in combination with (S)-1-(4-chlorophenyl)-7-isopropoxy-6-methoxy-2-(4-(methyl(((1R,4S)-4-(4-methyl-3-oxopiperazin-1-yl)cyclohexyl)methypamino)phenyl)-1,2-dihydroisoquinolin-3(4H)-one (Compound A10), or a compound disclosed in PCT Publication No. WO 2011/076786, to treat a disorder such as a solid tumor. In one embodiment, the HDM2 inhibitor or (S)-1-(4-chlorophenyl)-7-isopropoxy-6-methoxy-2-(4-(methyl(((1R,4S)-4-(4-methyl-3-oxopiperazin-1-yl)cyclohexyl)methypamino)phenyl)-1,2-dihydroisoquinolin-3 (4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination includes, e.g., a combination comprising a compound of the present invention, such as 2'2'-RR-(3'F-A)(3'F-A) as described herein, used in combination with an iron chelating agent, Deferasirox (also known as EXJADE; Compound A11), or a compound disclosed in PCT Publication No. WO 1997/049395, to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, the compound of the present invention, such as 2'2'-RR-(3'F-A)(3'F-A) is used in combination with Deferasirox (Compound A11), or a compound disclosed in PCT Publication No. WO 1997/049395, to treat iron overload, hemochromatosis, or myelodysplasia.

In another embodiment, the combination includes, e.g., a combination comprising a compound of the present invention, such as 2'2'-RR-(3'F-A)(3'F-A) as described herein, used in combination with an aromatase inhibitor, Letrozole (also known as FEMARA; Compound A12), or a compound disclosed in U.S. Pat. No. 4,978,672, to treat a disorder, e.g., a disorder described herein. In one embodiment, the aromatase inhibitor is Letrozole (Compound A12) or a compound disclosed in U.S. Pat. No. 4,978,672. In one embodiment, the compound of the present invention, such as 2'2'-RR-(3'F-A)(3'F-A) is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination includes, e.g., a combination comprising a compound of the present invention, such as 2'2'-RR-(3'F-A)(3'F-A) as described herein, used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826, to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, the compound of the present invention, such as 2'2'-RR-(3'F-A)(3'F-A) is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination includes, e.g., a combination comprising a compound of the present invention, such as 2'2'-RR-(3'F-A)(3'F-A) as described herein, used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, the compound of the present invention, such as 2'2'-RR-(3'F-A)(3'F-A) is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination includes, e.g., a combination comprising a compound of the present invention, such as 2'2'-RR-(3'F-A)(3'F-A) as described herein, used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2007/121484, to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2007/121484. In one embodiment, the compound of the present invention, such as 2'2'-RR-(3'F-A)(3'F-A) is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2007/121484, to treat a disorder such as cancer.

In another embodiment, the combination includes, e.g., a combination comprising a compound of the present invention, such as 2'2'-RR-(3'F-A)(3'F-A) as described herein, used in combination with an apoptosis inducer and/or an angiogenesis inhibitor, such as Imatinib mesylate (also known as GLEEVEC; Compound A16) or a compound disclosed in PCT Publication No. WO1999/003854, to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, the compound of the present invention, such as 2'2'-RR-(3'F-A)(3'F-A) is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis. In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination includes, e.g., a combination comprising a compound of the present invention, such as 2'2'-RR-(3'F-A)(3'F-A) as described herein, used in combination with a JAK inhibitor, 2-fluoro-N-methyl-4-(7-(quinolin-6-ylmethy)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, the compound of the present invention, such as 2'2'-RR-(3'F-A)(3'F-A) is used in combination with 2-fluoro-N-methyl-4-(7-(quinolin-6-ylmethypimidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia. In one embodiment, the JAK inhibitor or a 2-fluoro-N-methyl-4-(7-(quinolin-6-ylmethy)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination includes, e.g., a combination comprising a compound of the present invention, such as 2'2'-RR-(3'F-A)(3'F-A) as described herein, used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, the compound of the present invention, such as 2'2'-RR-(3'F-A)(3'F-A) is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia. In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination includes, e.g., a combination comprising a compound of the present invention, such as 2'2'-RR-(3'F-A)(3'F-A) as described herein, used in combination with a histone deacetylase (HDAC) inhibitor. In some embodiments, the HDAC inhibitor is selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745. In some embodiments, the combination comprising the compound of the present invention, such as 2'2'-RR-(3'F-A)(3'F-A) as described herein, is used in combination with a histone deacetylase (HDAC) inhibitor, Panobinostat (Compound A19), or a compound disclosed in PCT Publication No. WO 2014/072493, to treat a disorder, e.g., a disorder described herein. In one embodiment, the HDAC inhibitor is Panobinostat (Compound A19) or a compound disclosed in PCT Publication No. WO 2014/072493. In one embodiment, the compound of the present invention, such as 2'2'-RR-(3'F-A)(3'F-A) is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In one embodiment, the HDAC inhibitor or Panobinostat (Compound A19) is administered at a dose of about 20 mg (e.g., per day).

In another embodiment, the combination includes, e.g., a combination comprising a compound of the present invention, such as 2'2'-RR-(3'F-A)(3'F-A) as described herein, used in combination with an inhibitor of one or more of cytochrome P450 (e.g., 11B2), aldosterone or angiogenesis, Osilodrostat (Compound A20), or a compound disclosed in PCT Publication No. WO2007/024945, to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, the compound of the present invention, such as 2'2'-RR-(3'F-A)(3'F-A) is used in combination with Osilodrostat (Compound A20), or a compound disclosed in PCT Publication No. WO2007/024945, to treat a disorder such as Cushing's syndrome, hypertension, or heart failure therapy.

In another embodiment, the combination includes, e.g., a combination comprising a compound of the present invention, such as 2'2'-RR-(3'F-A)(3'F-A) as described herein, used in combination with a IAP inhibitor, (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No.

8,552,003, to treat a disorder, e.g., a disorder described herein. In one embodiment, the IAP inhibitor is (S)-N-((S)-1-cyclohexyl-2-((S)-2-(4-(4-fluorobenzoyOthiazol-2-yl)pyrrolidin-1-yl)-2-oxoethyl)-2-(methylamino)propanamide (Compound A21) or a compound disclosed in U.S. Pat. No. 8,552,003. In one embodiment, the compound of the present invention, such as 2'2'-RR-(3'F-A)(3'F-A) is used in combination with (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder. In one embodiment, the IAP inhibitor or (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the combination includes, e.g., a combination comprising a compound of the present invention, such as 2'2'-RR-(3'F-A)(3'F-A) as described herein, used in combination a Smoothened (SMO) inhibitor, such as (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120, to treat a disorder, e.g., a disorder described herein. In one embodiment, the SMO inhibitor is (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, the compound of the present invention, such as 2'2'-RR-(3'F-A)(3'F-A) is used in combination with (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation. In certain embodiments, the SMO inhibitor is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination includes, e.g., a combination comprising a compound of the present invention, such as 2'2'-RR-(3'F-A)(3'F-A) as described herein, used in combination with an Alk inhibitor, ceritinib (also known as ZYKADIA; Compound A23) or a compound disclosed in PCT Publication No. WO 2007/131201, to treat a disorder, e.g., a disorder described herein. In one embodiment, the Alk inhibitor is centinib (Compound A23) or a compound disclosed in PCT Publication No. WO 2007/131201. In one embodiment, the compound of the present invention, such as 2'2'-RR-(3'F-A)(3'F-A) is used in combination with coritmib (Compound A23), or a compound disclosed in PCT Publication No. WO 2007/131201, to treat a disorder such as non-small cell lung cancer or solid tumors. In one embodiment, the Alk inhibitor or ceritinib (Compound A23) is administered at a dose of approximately 750 mg, e.g., once daily.

In another embodiment, the combination includes, e.g., a combination comprising a compound of the present invention, such as 2'2'-RR-(3'F-A)(3'F-A) as described herein, used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980, to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. Nos. 8,415,355 or 8,685,980. In one embodiment, the compound of the present invention, such as 2'2'-RR-(3'F-A)(3'F-A) is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980, to treat a disorder such as a lymphoma, a neurologic cancer, a melanoma, a breast cancer, or a solid tumor. In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the combination includes, e.g., a combination comprising a compound of the present invention, such as 2'2'-RR-(3'F-A)(3'F-A) as described herein, used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124, to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, the compound of the present invention, such as 2'2'-RR-(3'F-A)(3'F-A) is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination includes, e.g., a combination comprising a compound of the present invention, such as 2'2'-RR-(3'F-A)(3'F-A) as described herein, used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849, to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, the compound of the present invention, such as 2'2'-RR-(3'F-A)(3'F-A) is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, 2-(2',3-dimethyl-[2,4'-bipyridin]-5-yl)-N-(5-

(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the combination includes, e.g., a combination comprising a compound of the present invention, such as 2'2'-RR-(3'F-A)(3'F-A) as described herein, used in combination with a BRAF inhibitor, e.g., a compound disclosed in PCT Publication No. WO 2011/025927, to treat a disorder, e.g., a disorder described herein. In one embodiment, the BRAF inhibitor is a compound disclosed in PCT Publication No. WO 2011/025927. In one embodiment, the compound of the present invention, such as 2'2'-RR-(3'F-A)(3'F-A) is used in combination with a compound disclosed in PCT Publication No. WO 2011/025927, to treat a disorder such as a non-small cell lung cancer, a melanoma, or a colorectal cancer. In one embodiment, the BRAF inhibitor is administered at a dose of about 200-300, 200-400, or 300-400 mg, e.g., per day. In one embodiment, the compound is administered at a dose of about 200, about 300 or about 400 mg.

In another embodiment, the combination includes, e.g., a combination comprising a compound of the present invention, such as 2'2'-RR-(3'F-A)(3'F-A) as described herein, used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, the compound of the present invention, such as 2'2'-RR-(3'F-A)(3'F-A) is used in combination with 7-cyclopentyl-N,N-dimethyl-2-((5-((lR,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination includes, e.g., a combination comprising a compound of the present invention, such as 2'2'-RR-(3'F-A)(3'F-A) as described herein, used in combination with a MEK inhibitor, e.g., a compound disclosed in PCT Publication No. WO 2003/077914, to treat a disorder, e.g., a disorder described herein. In one embodiment, the MEK inhibitor is a compound disclosed in PCT Publication No. WO 2003/077914. In one embodiment, the compound of the present invention, such as 2'2'-RR-(3'F-A)(3'F-A) is used in combination with a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer. In one embodiment, the MEK inhibitor is administered at a dose of about 45 mg, e.g., twice daily.

In another embodiment, the combination includes, e.g., a combination comprising a compound of the present invention, such as 2'2'-RR-(3'F-A)(3'F-A) as described herein, used in combination an inhibitor of one or more of c-KIT, histamine release, Flt3 (e.g., FLK2/STK1) or PKC, Midostaurin (Compound A35) or a compound disclosed in PCT Publication No. WO 2003/037347, to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, the compound of the present invention, such as 2'2'-RR-(3'F-A)(3'F-A) is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related macular degeneration, a diabetic complication, or a dermatologic disorder.

In another embodiment, the combination includes, e.g., a combination comprising a compound of the present invention, such as 2'2'-RR-(3'F-A)(3'F-A) as described herein, used in combination with a TOR inhibitor (e.g., mTOR inhibitor), Everolimus (also known as AFINITOR; Compound A36) or a Compound disclosed in PCT Publication No. WO 2014/085318, to treat a disorder, e.g., a disorder described herein). In one embodiment, the TOR inhibitor is Everolimus (Compound A36) or a Compound disclosed in PCT Publication No. WO 2014/085318. In one embodiment, the compound of the present invention, such as 2'2'-RR-(3'F-A)(3'F-A) is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer. In one embodiment, the TOR inhibitor or Everolimus is (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the combination includes, e.g., a combination comprising a compound of the present invention, such as 2'2'-RR-(3'F-A)(3'F-A) as described herein, used in combination with an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377, to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, the compound of the present invention, such as 2'2'-RR-(3'F-A)(3'F-A) is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination includes, e.g., a combination comprising a compound of the present invention, such as 2'2'-RR-(3'F-A)(3'F-A) as described herein, used in combination with a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761, to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, the compound of the present invention, such as 2'2'-RR-(3'F-A)(3'F-A) is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a neurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the combination includes, e.g., a combination comprising a compound of the present invention, such as 2'2'-RR-(3'F-A)(3'F-A) as described herein, used in combination with a signal transduction modulator and/or angiogenesis inhibitor, e.g., a compound disclosed in PCT Publication No. WO 2009/115562, to treat a disorder, e.g., a disorder described herein. In one embodiment, the signal transduction modulator and/or angiogenesis inhibitor is a compound disclosed in PCT Publication No. WO 2009/115562. In one embodiment, the compound of the present invention, such as 2'2'-RR-(3'F-A)(3'F-A) is used in combination with a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination includes, e.g., a combination comprising a compound of the present invention, such as 2'2'-RR-(3'F-A)(3'F-A) as described herein, used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, to treat a disorder, e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, the compound of the present invention, such as 2'2'-RR-(3'F-A)(3'F-A) is used in combination with (R,E)-N-(7-chloro-1-(1-(4-(dimethylamino) but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor. In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the combination includes, e.g., a combination comprising a compound of the present invention, such as 2'2'-RR-(3'F-A)(3'F-A) as described herein, used in combination with an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687, to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, the compound of the present invention, such as 2'2'-RR-(3'F-A)(3'F-A) is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination includes, e.g., a combination comprising a compound of the present invention, such as 2'2'-RR-(3'F-A)(3'F-A) as described herein, used in combination with an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655, to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, the compound of the present invention, such as 2'2'-RR-(3'F-A)(3'F-A) is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpipe ridin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the combination includes, e.g., a combination comprising a compound of the present invention, such as 2'2'-RR-(3'F-A)(3'F-A) as described herein, used in combination with a P-Glycoprotein 1 inhibitor, Valspodar (also known as AMDRAY; Compound A46) or a compound disclosed in EP 296122, to treat a disorder, e.g., a disorder described herein. In one embodiment, the P-Glycoprotein 1 inhibitor is Valspodar (Compound A46) or a compound disclosed in EP 296122. In one embodiment, the compound of the present invention, such as 2'2'-RR-(3'F-A)(3'F-A) is used in combination with Valspodar (Compound A46), or a compound disclosed in EP 296122, to treat a disorder such as a cancer or a drug-resistant tumor.

In another embodiment, the combination includes, e.g., a combination comprising a compound of the present invention, such as 2'2'-RR-(3'F-A)(3'F-A) as described herein, used in combination with one or more of a VEGFR inhibitor, Vatalanib succinate (Compound A47) or a compound disclosed in WO 98/35958, to treat a disorder, e.g., a disorder described herein. In one embodiment, the VEGFR inhibitor is Vatalanib succinate (Compound A47) or a compound disclosed in WO 98/35958. In one embodiment, the compound of the present invention, such as 2'2'-RR-(3'F-A)(3'F-A) is used in combination with Vatalanib succinate (Compound A47), or a compound disclosed in EP 296122, to treat cancer.

In another embodiment, the combination includes, e.g., a combination comprising a compound of the present invention, such as 2'2'-RR-(3'F-A)(3'F-A) as described herein, used in combination with an IDH inhibitor or a compound disclosed in WO2014/141104, to treat a disorder, e.g., a disorder described herein. In one embodiment, the IDH inhibitor is a compound disclosed in PCT Publication No. WO2014/141104. In one embodiment, the compound of the present invention, such as 2'2'-RR-(3'F-A)(3'F-A) is used in combination with a compound disclosed in WO2014/141104 to treat a disorder such as a cancer.

In another embodiment, the combination includes, e.g., a combination comprising a compound of the present invention, such as 2'2'-RR-(3'F-A)(3'F-A) as described herein, used in combination with a BCL-ABL inhibitor or a compound disclosed in PCT Publication No. WO2013/171639, WO2013/171640, WO2013/171641, or WO2013/171642, to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, the compound of the present invention, such as 2'2'-RR-(3'F-A)(3'F-A) is used in combination with a compound disclosed in PCT Publication No. WO2013/171639, WO2013/171640, WO2013/171641, or WO2013/171642 to treat a disorder such as a cancer.

In another embodiment, the combination includes, e.g., a combination comprising a compound of the present invention, such as 2'2'-RR-(3'F-A)(3'F-A) as described herein, used in combination with a c-RAF inhibitor or a compound disclosed in PCT Publication No. WO2014/151616, to treat a disorder, e.g., a disorder described herein. In one embodiment, the c-RAF inhibitor is Compound A50 or a compound disclosed in PCT Publication No. WO2014/151616. In one embodiment, the compound of the present invention, such as 2'2'-RR-(3'F-A)(3'F-A) is used in combination with a compound disclosed in PCT Publication No. WO2014/151616 to treat a disorder such as a cancer.

In another embodiment, the combination includes, e.g., a combination comprising a compound of the present invention, such as 2'2'-RR-(3'F-A)(3'F-A) as described herein, used in combination with an ERK1/2 ATP competitive inhibitor or a compound disclosed in PCT Publication No. WO2015/066188, to treat a disorder, e.g., a disorder described herein. In one embodiment, the ERK1/2 ATP competitive inhibitor is a compound disclosed in PCT Publication No. WO2015/066188. In one embodiment, the compound of the present invention, such as 2'2'-RR-(3'F-A)(3'F-A) is used in combination with Compound A51 or a compound disclosed in PCT Publication No. WO2015/066188 to treat a disorder such as a cancer. In some embodiments, the combination includes, e.g., a combination comprising the compound of the present invention, such as 2'2'-RR-(3'F-A)(3'F-A) as described herein, and Compound A51 or a compound disclosed in PCT Publication No. WO2015/066188, is administered in combination with one or more agents selected from, Compound A8, Compound A17, Compound A23, Compound A24, Compound A27, and Compound A33.

In another embodiment, the combination includes, e.g., a combination comprising a compound of the present invention, such as 2'2'-RR-(3'F-A)(3'F-A) as described herein, used in combination with an anti-cancer agent having a known activity in an immune cell assay, e.g., in one or more of a huMLR assay, a T cell proliferation assay, and a B-cell proliferation assay, where such assays are known in the art, and can be used to demonstrate the compounds used in combination will not inhibit an immune response (i.e., demonstrate little or no inhibition in such assays). An IC50 in such assays can be determined for the compounds to be used in combination with the compound of the present invention, such as 2'2'-RR-(3'F-A)(3'F-A). In embodiments, the anti-cancer agent has an IC50 of, e.g., >1 µM, 1-4 µM, or greater than 4 µM, e.g., 4-10 µM or 4-20 µM, or greater than 20 µM. In embodiments, the second therapeutic agent is chosen from one or more of: Compound A16, Compound A17, Compound A21, Compound A25, Compound A28, Compound A48, and Compound A49.

In some embodiments, the Compound A28 (or a compound related to Compound A28) is administered at a dose of approximately 5-10 or 10-30 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

TABLE 2

Therapeutic agents that can be administered in combination with the
2'2'-RR-(3'F-A)(3'-F-A) as described herein.

| Compound designation/ generic name | Patent/Reference | Compound Structure |
| --- | --- | --- |
| A1 Sotrastaurin | EP 1682102 US 2007/142401 WO 2005/039549 | (structure shown) |
| A2 Nilotinib HCl monohydrate TASIGNA ® | WO 2004/005281 U.S. Pat. No. 7,169,791 | (structure shown) HCl·H₂O |
| A7 | WO 2009/141386 US 2010/0105667 | (structure shown) |

TABLE 2-continued

Therapeutic agents that can be administered in combination with the 2'2'-RR-(3'F-A)(3'-F-A) as described herein.

| Compound designation/ generic name | Patent/Reference | Compound Structure |
|---|---|---|
| A8 | WO 2010/029082 | 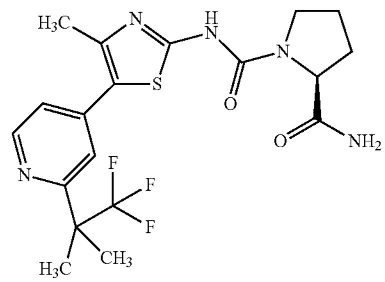 [SMILES: Cc1nc(NC(=O)N2CCC[C@H]2C(N)=O)sc1-c1ccnc(C(C)(C)C(F)(F)F)c1] |
| A10 | WO 2011/076786 | 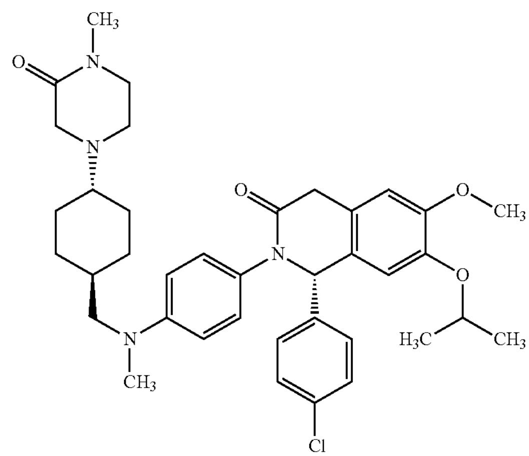 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] |
| A11 Deferasirox EXJADE ® | WO 1997/049395 | 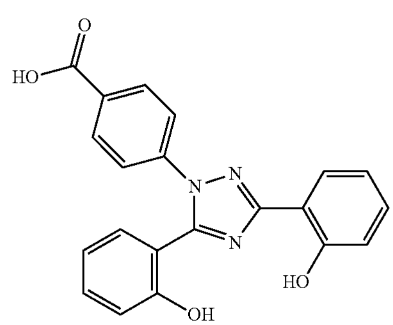 [SMILES: O=C(O)c1ccc(-n2nc(-c3ccccc3O)nc2-c2ccccc2O)cc1] |
| A12 Letrozole FEMARA ® | U.S. Pat. No. 4,978,672 | 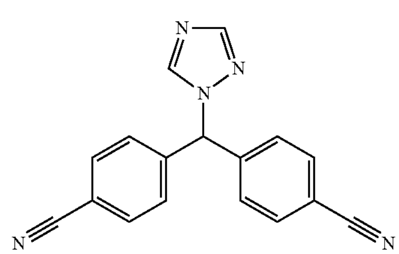 [SMILES: N#Cc1ccc(C(c2ccc(C#N)cc2)n2cncn2)cc1] |

TABLE 2-continued
Therapeutic agents that can be administered in combination with the 2'2'-RR-(3'F-A)(3'F-A) as described herein.
| Compound designation/ generic name | Patent/Reference | Compound Structure |
|---|---|---|
| A13 | WO 2013/124826<br>US 2013/0225574 | 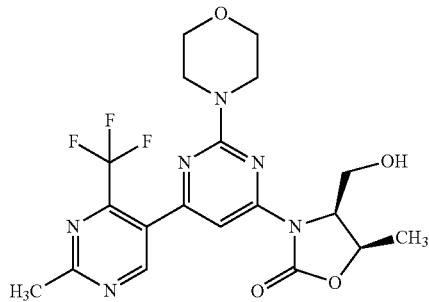 |
| A14 | WO 2013/111105 | 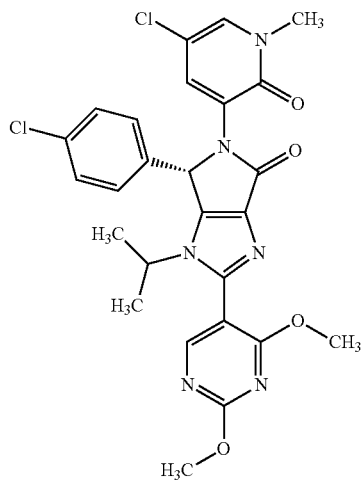 [SMILES: COc1ncc(-c2nc3c(n2C(C)C)[C@H](c2ccc(Cl)cc2)N(c2cc(Cl)cn(C)c2=O)C3=O)c(OC)n1] |
| A15 | WO 2007/121484 | 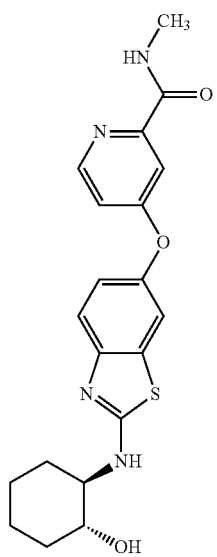 [SMILES: CNC(=O)c1cc(Oc2ccc3nc(N[C@@H]4CCCC[C@H]4O)sc3c2)ccn1] |

TABLE 2-continued
Therapeutic agents that can be administered in combination with the 2'2'-RR-(3'F-A)(3'-F-A) as described herein.
| Compound designation/ generic name | Patent/Reference | Compound Structure |
|---|---|---|
| A16 Imatinib mesylate GLEEVEC ® | WO 1999/003854 | 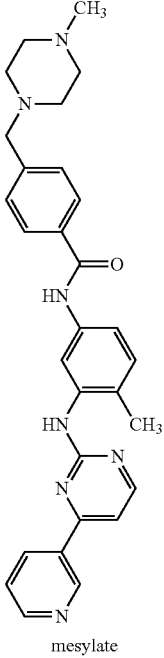 [SMILES: Cc1ccc(NC(=O)c2ccc(CN3CCN(C)CC3)cc2)cc1Nc1nccc(-c2cccnc2)n1]<br>mesylate |
| A17 | EP 2099447<br>U.S. Pat. No. 7,767,675<br>U.S. Pat. No. 8,420,645 | 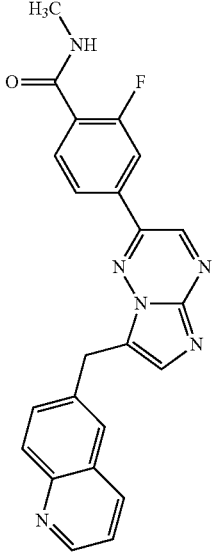<br>dihydrochloric salt |

TABLE 2-continued
Therapeutic agents that can be administered in combination with the 2'2'-RR-(3'F-A)(3'F-A) as described herein.
| Compound designation/generic name | Patent/Reference | Compound Structure |
|---|---|---|
| A18 Ruxolitinib phosphate JAKAFI ® | WO 2007/070514 EP 2474545 U.S. Pat. No. 7,598,257 WO 2014/018632 | 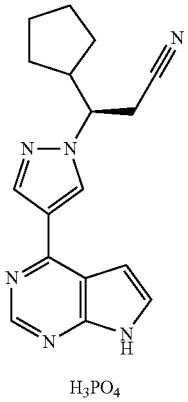 |
| A19 Panobinostat | WO 2014/072493 WO 2002/022577 EP 1870399 | 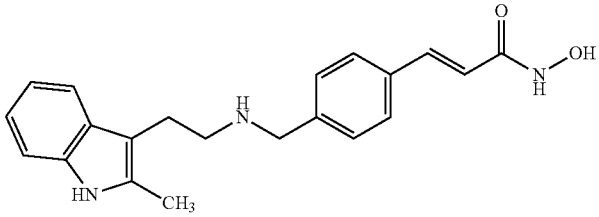 [SMILES: Cc1[nH]c2ccccc2c1CCNCc1ccc(/C=C/C(=O)NO)cc1] |
| A20 Osilodrostat | WO 2007/024945 | 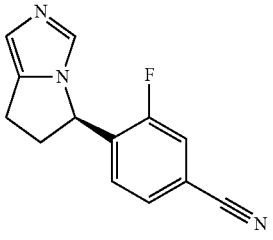 [SMILES: N#Cc1ccc([C@H]2CCc3cncn32)c(F)c1] |
| A21 | WO 2008/016893 EP 2051990 U.S. Pat. No. 8,546,336 | 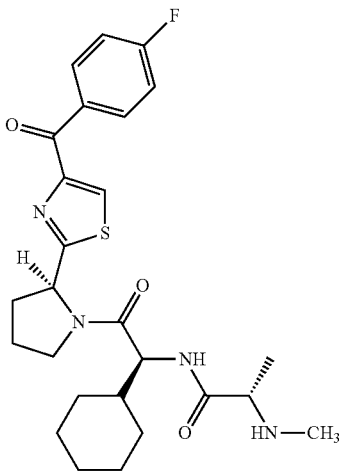 [SMILES: CN[C@@H](C)C(=O)N[C@H](C(=O)N1CCC[C@H]1c1nc(C(=O)c2ccc(F)cc2)cs1)C1CCCCC1] |

TABLE 2-continued
Therapeutic agents that can be administered in combination with the 2'2'-RR-(3'F-A)(3'F-A) as described herein.
| Compound designation/ generic name | Patent/Reference | Compound Structure |
|---|---|---|
| A23 Ceritinib ZYKADIA™ | WO 2008/073687 U.S. Pat. No. 8,039,479 | 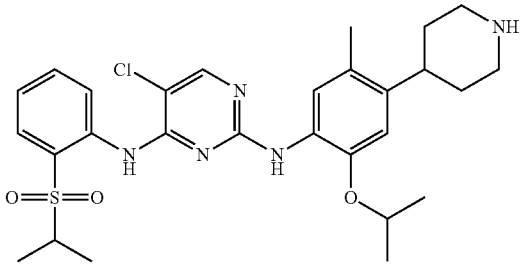 [SMILES: Cc1cc(Nc2ncc(Cl)c(Nc3ccccc3S(=O)(=O)C(C)C)n2)c(OC(C)C)cc1C1CCNCC1] |
| A24 | U.S. Pat. No. 8,415,355 U.S. Pat. No. 8,685,980 | 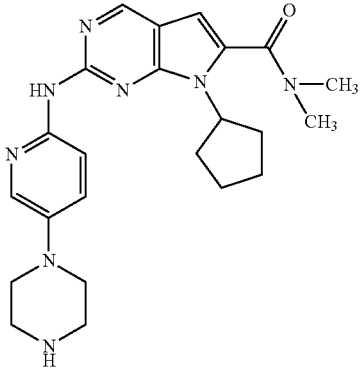 [SMILES: CN(C)C(=O)c1cc2cnc(Nc3ccc(N4CCNCC4)cn3)nc2n1C1CCCC1] |
| A25 | WO 2010/007120 | 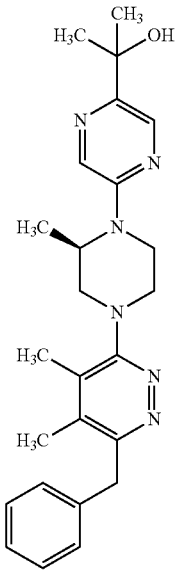 [SMILES: Cc1c(Cc2ccccc2)nnc(N2CCN(c3cnc(C(C)(C)O)cn3)[C@H](C)C2)c1C] |

TABLE 2-continued
Therapeutic agents that can be administered in combination with the 2'2'-RR-(3'F-A)(3'-F-A) as described herein.
| Compound designation/ generic name | Patent/Reference | Compound Structure |
| --- | --- | --- |
| A26 | U.S. Pat. No. 7,867,493 | Human monoclonal antibody to PRLR |
| A27 | WO 2010/026124<br>EP 2344474<br>US 2010/0056576<br>WO2008/106692 | 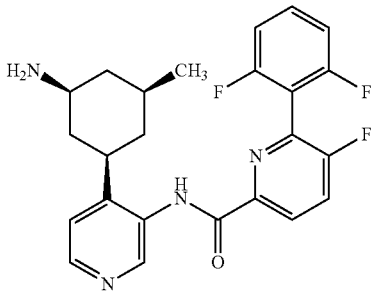 [SMILES: C[C@@H]1C[C@H](N)C[C@H](c2ccncc2NC(=O)c2ccc(F)c(-c3c(F)cccc3F)n2)C1] |
| A28 | WO 2010/101849 | 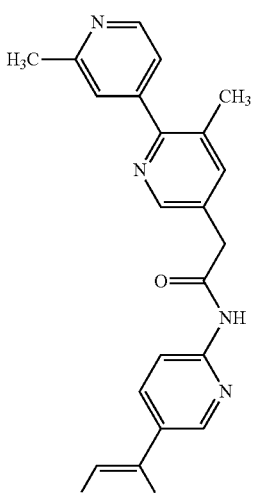 |
| A30 | WO 2011/101409 | 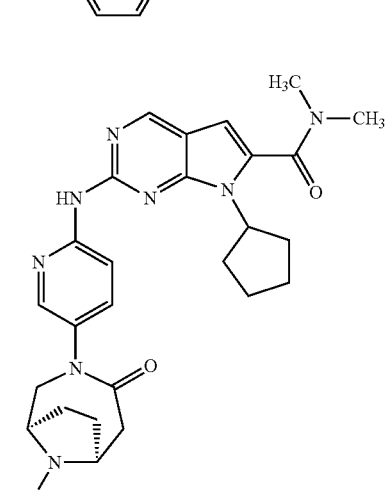 |

TABLE 2-continued

Therapeutic agents that can be administered in combination with the
2'2'-RR-(3'F-A)(3'-F-A) as described herein.

| Compound designation/ generic name | Patent/Reference | Compound Structure |
| --- | --- | --- |
| A31 | WO 2012/022814<br>EP 2606070<br>U.S. Pat. No. 8,735,551 | Human monoclonal antibody to HER3 |
| A32 | WO 2014/160160<br>Ab: 12425 (see Table 1, paragraph [00191])<br>Linker: SMCC (see paragraph [00117]<br>Payload: DM1 (see paragraph [00111]<br>See also Claim 29 | Antibody Drug Conjugate (ADC) |
| A33 | WO 2004/045532 | Monoclonal antibody or Fab to M-CSF |
| A35<br>Midostaurin | WO 2003/037347<br>EP 1441737<br>US 2012/252785 | 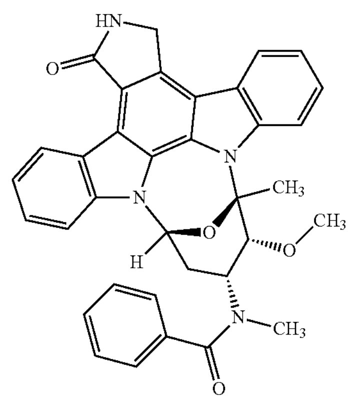 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] |
| A36<br>Everolimus<br>AFINITOR ® | WO 2014/085318 | 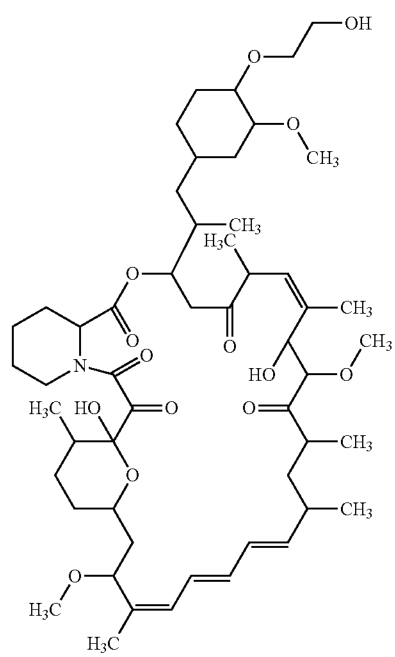 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] |

TABLE 2-continued

Therapeutic agents that can be administered in combination with the 2'2'-RR-(3'F-A)(3'-F-A) as described herein.

| Compound designation/ generic name | Patent/Reference | Compound Structure |
|---|---|---|
| A37 | WO 2007/030377<br>U.S. Pat. No. 7,482,367 | 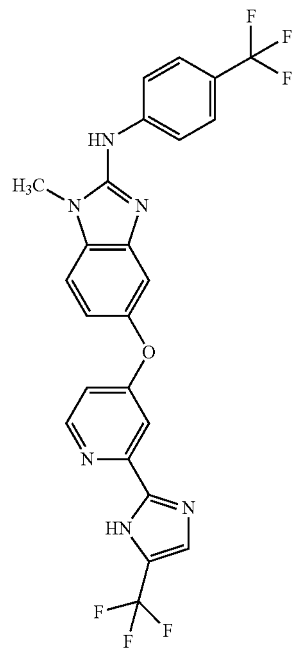 [SMILES: Cn1c(Nc2ccc(C(F)(F)F)cc2)nc2cc(Oc3ccnc(-c4ncc(C(F)(F)F)[nH]4)c3)ccc21] |
| A38<br>Pasireotide diaspartate<br>SIGNIFOR ® | WO2002/010192<br>U.S. Pat. No. 7,473,761 | 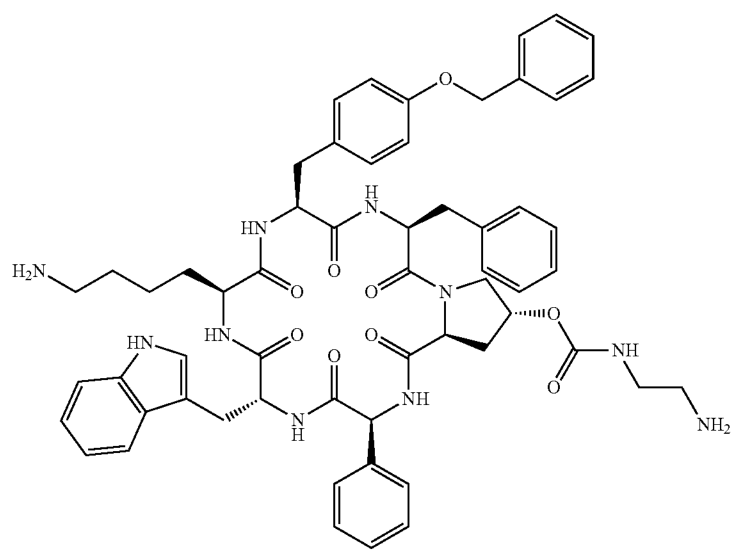 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] |
| A40 | WO 2013/184757 | 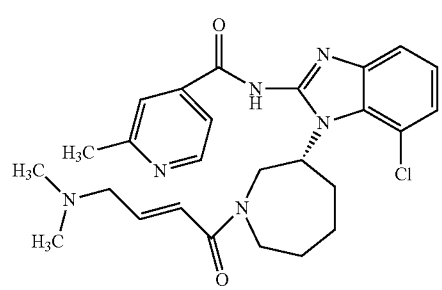 [SMILES: Cc1cc(C(=O)Nc2nc3cccc(Cl)c3n2[C@@H]2CCCCN(C(=O)/C=C/CN(C)C)C2)ccn1] |

TABLE 2-continued

Therapeutic agents that can be administered in combination with the 2'2'-RR-(3'F-A)(3'-F-A) as described herein.

| Compound designation/generic name | Patent/Reference | Compound Structure |
|---|---|---|
| A41 | WO 2006/122806 | 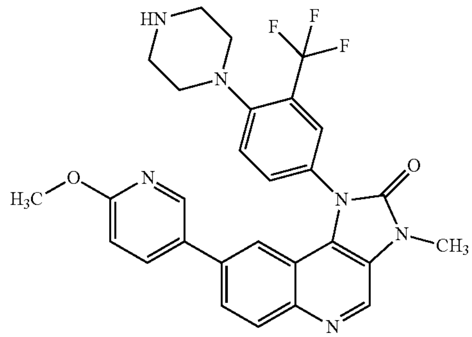 |
| A42 | WO 2008/073687<br>U.S. Pat. No. 8,372,858 | 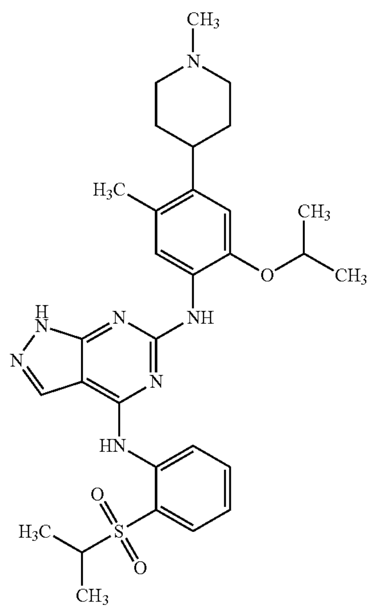 [SMILES: Cc1cc(Nc2nc(Nc3ccccc3S(=O)(=O)C(C)C)c3cn[nH]c3n2)c(OC(C)C)cc1C1CCN(C)CC1] |
| A43 | WO 2010/002655<br>U.S. Pat. No. 8,519,129 | 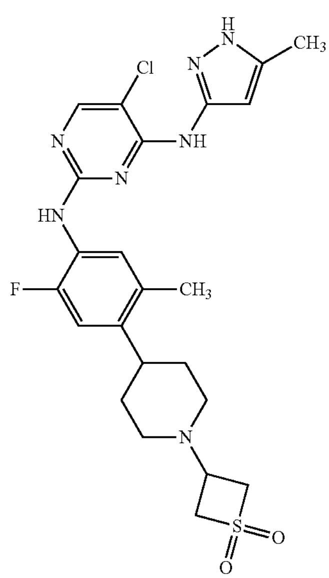 [SMILES: Cc1cc(Nc2nc(Nc3cc(C)c(C4CCN(C5CS(=O)(=O)C5)CC4)cc3F)ncc2Cl)n[nH]1] |

TABLE 2-continued
Therapeutic agents that can be administered in combination with the 2'2'-RR-(3'F-A)(3'F-A) as described herein.
| Compound designation/ generic name | Patent/Reference | Compound Structure |
| --- | --- | --- |
| A44 | WO 2010/002655 U.S. Pat. No. 8,519,129 | 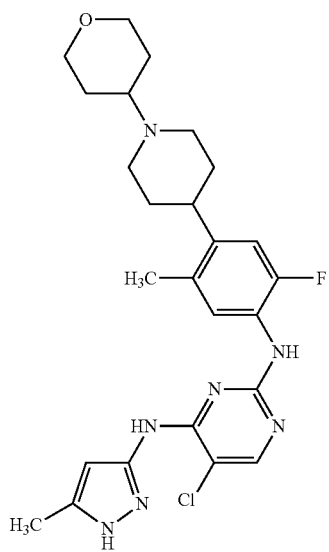 [SMILES: Cc1cc(Nc2nc(Nc3cc(C)c(C4CCN(C5CCOCC5)CC4)cc3F)ncc2Cl)n[nH]1] |
| A45 | WO 2010/002655 | 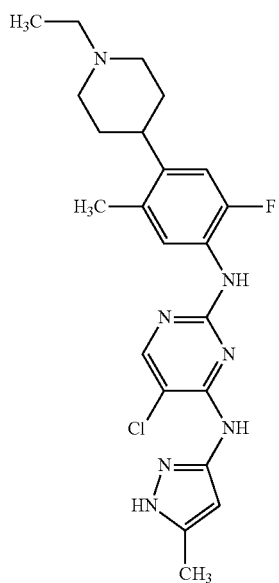 [SMILES: CCN1CCC(c2cc(F)c(Nc3ncc(Cl)c(Nc4cc(C)[nH]n4)n3)cc2C)CC1] |

TABLE 2-continued

Therapeutic agents that can be administered in combination with the 2'2'-RR-(3'F-A)(3'-F-A) as described herein.

| Compound designation/ generic name | Patent/Reference | Compound Structure |
|---|---|---|
| A46 Valspodar AMDRAY ™ | EP 296122 | 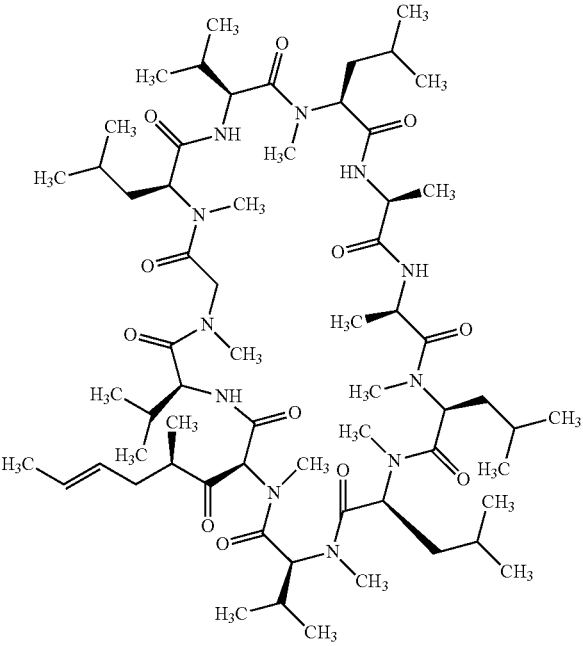 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| A47 Vatalanib succinate | WO 98/35958 | 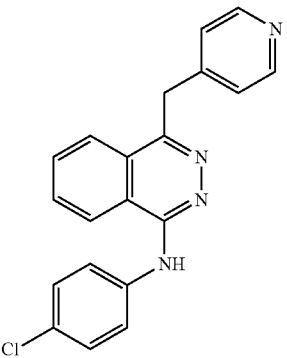 succinate |
| A48 | WO2014/141104 | IDH inhibitor |
| A49 | WO2013/171639 WO2013/171640 WO2013/171641 WO2013/171642 | BCR-ABL inhibitor |
| A50 | WO2014/151616 | cRAF inhibitor |
| A51 | WO2015/066188 | ERK1/2 ATP competitive inhibitor |

Immunomodulatory Cell Lines

By "inactivated tumor cell" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res. 2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

TABLE 1

List of antigens for use in combination with the compound of the present invention, such as 2'2'-RR-(3'F-A)(3'F-A) as described herein.

| Antigen | Reference |
| --- | --- |
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |

TABLE 1-continued

List of antigens for use in combination with the compound of the present invention, such as 2'2'-RR-(3'F-A)(3'F-A) as described herein.

| Antigen | Reference |
| --- | --- |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |

TABLE 1-continued

List of antigens for use in combination with the compound of the present
invention, such as 2'2'-RR-(3'F-A)(3'F-A) as described herein.

| Antigen | Reference |
|---|---|
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_i76795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |

TABLE 1-continued

List of antigens for use in combination with the compound of the present
invention, such as 2'2'-RR-(3'F-A)(3'F-A) as described herein.

| Antigen | Reference |
|---|---|
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, |

TABLE 1-continued

List of antigens for use in combination with the compound of the present invention, such as 2'2'-RR-(3'F-A)(3'F-A) as described herein.

| Antigen | Reference |
| --- | --- |
| | and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

Francisella tularensis antigens

| Antigen | Reference |
| --- | --- |
| Francisella tularensis A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of F. tularensis include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

Malarial antigens

| Antigen | Reference |
| --- | --- |
| Circumsporozoite protein (CSP); SSP2; HEP17; Exp-1 orthologs found in P. falciparum; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A'13; AJ494905; AJ490565). |

Viruses and viral antigens

| Antigen | Reference |
| --- | --- |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g., NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |

TABLE 1-continued

List of antigens for use in combination with the compound of the present invention, such as 2'2'-RR-(3'F-A)(3'F-A) as described herein.

| Antigen | Reference |
|---|---|
| Toroviruses. | |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HEIV-8), including subtypes A-E, are disclosed in, e.g., Treurnicht, et al. (2002) J. Med. Virul. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, | See, e.g., Barthold, et al. (1993) Lab. Anim. Sci. 43: 425-430; Roner, et al. (1995) Proc. Natl. Acad. Sci. USA 92: 12362-12366; Kedl, et al. |

TABLE 1-continued

List of antigens for use in combination with the compound of the present
invention, such as 2'2'-RR-(3'F-A)(3'F-A) as described herein.

| Antigen | Reference |
|---|---|
| 2, and 3, type 1 Lang, type 2 Jones, and type 3 Dearing. | (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797;NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |

TABLE 1-continued

List of antigens for use in combination with the compound of the present
invention, such as 2'2'-RR-(3'F-A)(3'F-A) as described herein.

| Antigen | Reference |
|---|---|
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9)(5V40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrhoeae, Vibrio cholerae, Salmonella* species (including *typhi, typhimurium*), enterica (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, *The Science and Practice of Pharmacy* $21^{st}$ Edition (Mack Publishing Co., Easton, Pa.) and Nielloud and Marti-Mestres, Pharmaceutical Emulsions and Suspensions: $2^{nd}$ Edition (Marcel Dekker, Inc, New York).

For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters.

Administration via intracoronary stents and intracoronary reservoirs is also contemplated. Intra-tumoral (directly into the tumor mass) or peri-tumoral (around the tumor mass) administration of the compound of the present invention, such as 2'2'-RR-(3'F-A)(3'F-A) may directly activate locally infiltrating DC, directly promote tumor cell apoptosis or sensitize tumor cells to cytotoxic agents. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with a compound of the present invention, such as 2'2'-RR-(3'F-A)(3'F-A) as described herein when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e., the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of 2'2'-RR-(3'F-A)(3'F-A) are preferably pharmaceutically acceptable. Suitable pharmaceutically acceptable salts include those described by P. Heinrich Stahl and Camille G. Wermuth in *Handbook of Pharmaceutical Salts: Properties, Selection, and Use*, $2^{nd}$ ed. (Wiley-VCH: 2011) and also *Remington's Pharmaceutical Sciences*, $18^{th}$ ed. (Mack Publishing, Easton Pa.: 1990) and also *Remington: The Science and Practice of Pharmacy*, $19^{th}$ ed. (Mack Publishing, Easton Pa.: 1995). Salt encompassed within the term "pharmaceutically acceptable salts" refer to non-toxic salts of 2'2'-RR-(3'F-A)(3'F-A).

Salts of a compound of the present invention, such as 2'2'-RR-(3'F-A)(3'F-A) containing a basic amine or other basic functional group may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, glycolate, resinate, lactates, camsylates, tartrates, mandelates, and sulfonates, such as xylenesulfonates, methanesulfonates, propanesulfonates, naphthalene-1-sulfonates and naphthalene-2-sulfonates.

Salts of a compound of the present invention, such as 2'2'-RR-(3'F-A)(3'F-A) containing a phosphate diester, phosphorothioate diester or other acidic functional group can be prepared by reacting with a suitable base. Pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

2'2'-RR-(3'F-A)(3'F-A) as described herein that include salts thereof can be described by structures wherein the —SH of the thiophosphate bonds are represented as —S⁻ with a corresponding cation to form salts of the compounds as described herein. For example, salts of 2'2'-RR-(3'F-A)(3'F-A) can be represented by the following structures:

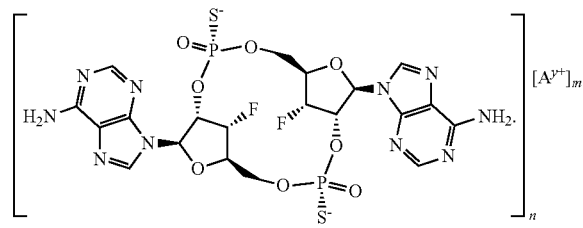

wherein $A^{y+}$ represents a mono or polyvalent salt cation, and n and m are the lowest possible whole number for a given y. For example when $A^{y-}$ is monovalent, i.e., when y is 1, such as Na⁺, K⁺, NH₄⁻, TEAR⁺ or the like, n is 1 and m is 2; when y is 2, such as Ca²⁺, Mg²⁺ and the like, n is 1 and m is 1; when y is 3, e.g., Al³⁺ or the like, n is 3 and m is 2. For example, salts of a monovalent or divalent salt cation can be represented as

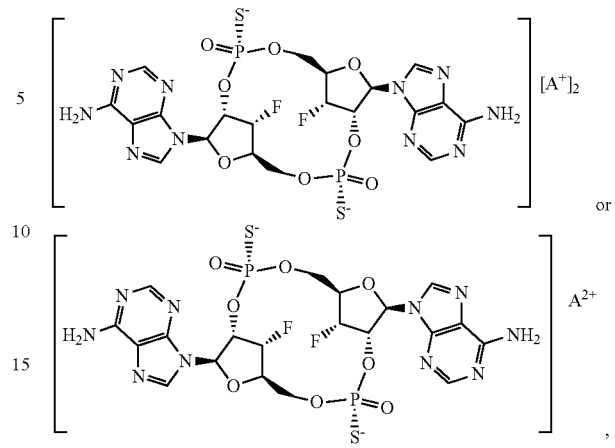

respectively, or in cases where n=1, these can be represented without brackets, e.g., as

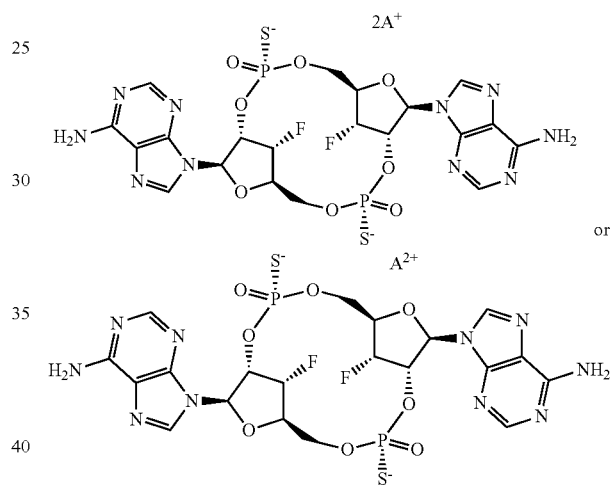

Alternatively, monovalent salts can be depicted with A⁺ adjacent each —S⁻. For example, the sodium salt of 2'2'-RR-(3'F-A)(3'F-A) can be depicted as

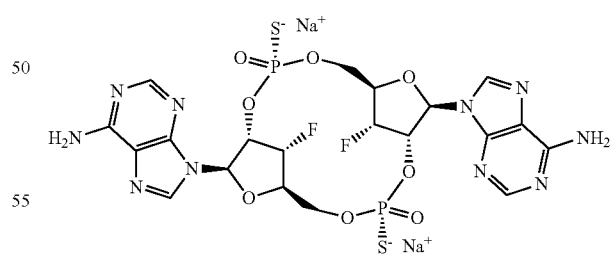

Other non-pharmaceutically acceptable salts, e.g., trifluoroacetate or triethylammonium may be used, for example in the isolation of 2'2'-RR-(3'F-A)(3'F-A), and are included within the scope of this invention.

The invention includes within its scope all possible stoichiometric and non-stoichiometric forms of the salts of 2'2'-RR-(3'F-A)(3'F-A).

If a compound containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of 2'2'-RR-(3'F-A)(3'F-A), or a pharmaceutically acceptable salt, pharmaceutically acceptable solvate or pharmaceutically acceptable hydrate thereof as described herein, for a particular patient may vary depending on factors such as the condition being treated, the overall health of the patient, the route and dose of administration and the severity of side effects. One advantage of a compound of the present invention, such as 2'2'-RR-(3'F-A)(3'F-A), is the lesser variation in binding across hSTING alleles, reducing variability in dosing of from patient to patient depending on their particular hSTING variant. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of a pharmaceutical composition comprising 2'2'-RR-(3'F-A)(3'F-A), or a pharmaceutically acceptable salt, pharmaceutically acceptable solvate or pharmaceutically acceptable hydrate thereof as described herein. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; every 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g., same formulation) such that they are administered at the same time by the same route of administration.

As noted, the compositions of the present invention are preferably formulated as pharmaceutical compositions for parenteral or enteral delivery. A typical pharmaceutical composition for administration to an animal subject comprises a pharmaceutically acceptable vehicle such as aqueous solutions, non-toxic excipients, including salts, preservatives, buffers and the like. See, e.g., *Remington's Pharmaceutical Sciences, 15th Ed.*, Easton ed., Mack Publishing Co., pp 1405-1412 and 1461-1487 (1975); *The National Formulary XIV, 14th Ed.*, American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/2'2'-RR-(3'F-A)(3'F-A) or compositions thereof described herein. The heterologous arm of the regimen may comprise delivery of antigen using one or more of the following strategies:

Inactivated or attenuated bacteria or viruses comprising the antigen of interest, which are particles that have been treated with some denaturing condition to render them ineffective or inefficient in mounting a pathogenic invasion;

Purified antigens, which are typically naturally-produced antigens purified from a cell culture of the pathogen or a tissue sample containing the pathogen, or a recombinant version thereof;

Live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

Antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer); liposomal antigen delivery vehicles; and Naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

EXAMPLES

The following examples serve to illustrate the present invention. These examples are in no way intended to limit the scope of the invention.

General Methods

Anhydrous solvents and reagents suitable for solution phase oligonucleotide synthesis were purchased from commercial suppliers (Aldrich, ChemGenes Corporation, Wilmington, Mass., USA) and handled under dry argon or nitrogen using anhydrous technique. Phosphoramidite coupling reactions and H-phosphonate cyclizations were carried out in anhydrous acetonitrile or pyridine under dry argon or nitrogen. The starting materials for all reactions in dry pyridine were dried by concentration (three times) from pyridine, unless indicated otherwise. Chromatography conditions were as follows unless indicated otherwise in the examples below. Preparative silica gel flash chromatography was carried out under medium pressure chromatography (MPLC) using RediSep Rf silica columns (Teledyne Isco, Lincoln, Nebr.) on a Combiflash Rf+ UV-Vis (Teledyne Isco) using gradients of methanol in dichloromethane. Reverse phase preparative chromatography was executed under MPLC conditions using RediSep Rf C18 Aq columns (Teledyne Isco) on a Combiflash Rf+ UV-Vis using gradients of acetonitrile in aqueous 10 mM TEAA solution. Analytical high pressure liquid chromatography (HPLC) was performed on a Shimadzu Prominence HPLC system with two LC-20AD pumps and a SPD-M30A photodiode array detector monitoring at 254 nm. Gradients of 10 mM TEAA in acetonitrile or 20 mM $NH_4OAc$ in acetonitrile were used with either a 5 micron (Thermo Scientific Acclaim 120) C-18 column (4.6×250 mm) or a 10 micron (Thermo Scientific Hypersil) C-18 column (4.0×250 mm) at room temperature. Ultra-Performance analytical high pressure liquid chromatography (UPLC) was performed on a Shimadzu Nexera X2 LCMS system with two LC-30AD pumps and a SPD-M30A photodiode array detector monitoring at 254 nm. Gradients of 20 mM $NH_4OAc$ in acetonitrile were used with a 1.7 micron (Acquity UPLC® BEH) C-18 column (2.1×30 mm) at room temperature. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 ml/min. Solid phase extractions using C-18 Sep-Pak (Waters) were carried out at loadings of 3% (wt/wt). Analytical LCMS were recorded using a Shimadzu LCMS system featuring a Prominence HPLC coupled to a Shimadzu LCMS-2020 single quadrupole mass spectrometer, using an electrospray ionization source (ESI). Additional or alternative instrumentation and methods may also be provided in the examples that follow.

$^1$H NMR, $^{19}$F NMR, $^{31}$P NMR and $^{13}$C NMR spectra were recorded in $CDCl_3$, d6-DMSO, $CD_3OD$ or $D_2O$ as solvent, using a Bruker 400 MHz spectrometer with a broad band channel and variable temperature probe. The operating frequency for 1H was 400 MHz, $^{19}$F was 376 MHz, $^{31}$P was 162 MHz, and $^{13}$C was 100 MHz. All spectra were recorded at ambient temperature (20-25° C.) unless otherwise noted. The temperature for variable-temperature experiments was calibrated monthly or bimonthly using the ethylene glycol method described in C. Amman, P. Meier and A. E. Merbach, *J. Magn. Reson.* 1982, 46, 319-321.

The final compounds may exist as the triethylammonium ($TEAH^+$ or $Et_3NH^-$) salt, which can be converted to other salt forms (including but not limited to sodium ($Na^+$) or ammonium ($NH_4^-$)) using standard ion exchange techniques or other well known methods.

Assignments of Stereochemistry at the phosphorus were made in analogy to literature methods (Zhao et al. Nucleosides, Nucleotides, and Nucleic Acid 289:352-378, 2009) or as discussed in the examples below.

Compound names were generated using the software program ChemBioDraw Ultra V 14.0 available from CambridgeSoft Corporation, 100 CambridgePark Drive, Cambridge, Mass. 02140 USA (www.cambridgesoft.com). Abridged names of compounds for which a name could not be generated by ChemBioDraw, or reference compounds used in the examples, are provided in the following Table 3. Comparative compounds 3'3'-RR-(2'F-A)(2'F-A) and 2'3'-RR-(3'F-A)(2'F-A) were prepared as described in Example 1 of PCT Publication No. WO2016/145102 or Example 2 of PCT Publication No. WO2017/075477, the disclosures of which are hereby incorporated by reference with respect to such syntheses. Structures in the examples may also be represented as salts, e.g., —O⁻ A⁺ or –S⁻ A⁺, where A⁺ is the salt cation.

TABLE 3

Abridged compound names and structures.

Example 2 Compound 8
2'2'-RR-(3'F-A)(3'F-A)
dithio-(Rp,Rp)-cyclic-[3'-F-A(2',5')p-3'F-A(2',5')p]
(1S,3R,6R,8R,9S,11R,14R,16R,17R,18R)-8,16-bis(6-amino-9H-purin-9-yl)-17,18-difluoro-3,11-dimercapto-2,4,7,10,12,15-hexaoxa-3,11-diphosphatricyclo[12.2.1.1$^{6,9}$]octadecane 3,11-dioxide

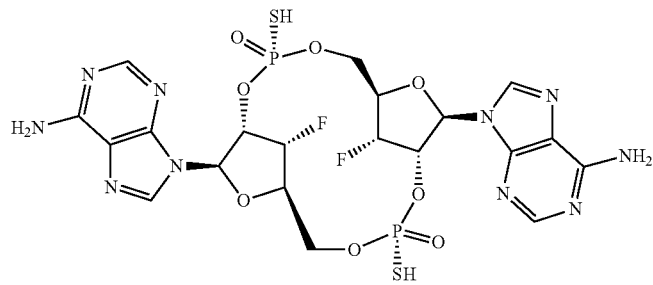 [SMILES: Nc1ncnc2c1ncn2[C@@H]1O[C@@H]2CO[P@@](=O)(S)O[C@@H]3[C@H](F)[C@@H](CO[P@@](=O)(S)O[C@@H]1[C@@H]2F)O[C@H]3n1cnc2c(N)ncnc21]

Example 3 Compound 15
2'2'-RR-(A)(A)
dithio-(Rp,Rp)-cyclic-[A(2',5')p-A(2',5')p]
(1R,3R,6R,8R,9R,11R,14R,16R,17R,18R)-8,16-bis(6-amino-9H-purin-9-yl)-17,18-dihydroxy-3,11-dimercapo-2,4,7,10,12,15-hexaoxa-3,11-diphosphatricyclo[12.1.1.1$^{6,9}$]octadecane 3,11-dioxide

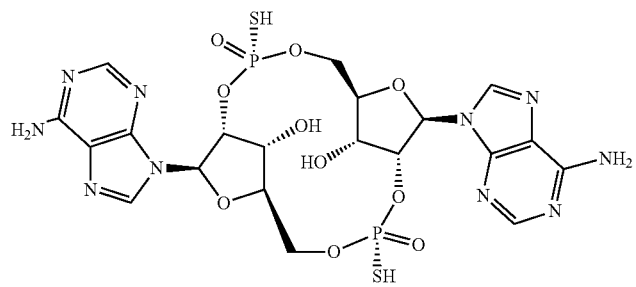 [SMILES: Nc1ncnc2c1ncn2[C@@H]1O[C@@H]2CO[P@@](=O)(S)O[C@@H]3[C@H](O)[C@@H](CO[P@@](=O)(S)O[C@@H]1[C@@H]2O)O[C@H]3n1cnc2c(N)ncnc21]

3'3'-RR-(2'F-A)(2'F-A);
dithio-Rp,Rp)-cyclic-[2'-F-A(3',5')p-2'-F-A(3',5')p]
(2R,3R,3aR,5R,7aR,9R,10R,10aR,12R,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide

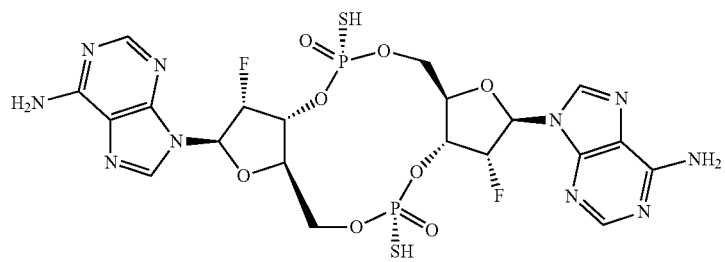 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1F]

TABLE 3-continued

Abridged compound names and structures.

2'3'-RR-(3'F-A)(2'F-A);
dithio-[$R_p,R_p$]-cyclic-[3'F-A(2',5')p-2'F-A(3',5')p]

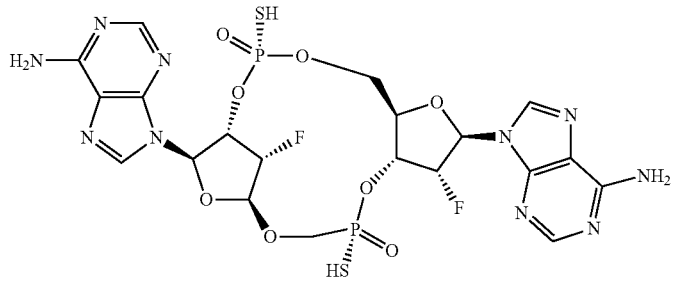 [SMILES: Nc1ncnc2c1ncn2[C@@H]1O[C@@H]2CO[P@@](=O)(S)O[C@@H]3[C@H](F)[C@@H](OC[P@@](=O)(S)O[C@H]2[C@H]1F)O[C@H]3n1cnc2c(N)ncnc21]

Abbreviations and Acronyms. SalPCl=Salicyl chlorophosphite. DCA=dichloroacetic acid. DDTT=((Dimethyl-amino-methylidene)amino)-3H-1,2,4-dithiazaoline-3-thione. DMP=Dess-Martin Periodinane DAST=diethylaminosulfur trifluoride. $NaHCO_3$=sodium bicarbonate. DCM=$CH_2Cl_2$=dichloromethane. IPA=isopropyl alcohol. EtOH=ethanol. EtOAc=ethyl acetate. AcOH=acetic acid. KOAc=potassium acetate. MeCN=acetonitrile. MeOH=methanol. $NH_4OAc$=ammonium acetate. $NH_4OH$=ammonium hydroxide. DMAP=N,N-dimethylpyridin-4-amine. DMOCP=2-chloro-5,5-dimethyl-1,3,2-dioxaphosphinane-2-oxide. DMTCl=4,4'-dimethoxytrityl chloride. DMT=4,4-dimethoxytrityl. N-phenyltriflamide=1,1,1-trifluoro-N-phenyl-N-((trifluoromethypsulfonyl)methanesulfonamide. TBAF=tetrabutylammonium fluoride. TBS=tert-butyldimethylsilyl. TEAA=Triethylammonium acetate. TEA=triethylamine. $TEAH^+$=triethylammonium. TEAB=triethylammonium bicarbonate. TFA=trifluoroacetic acid. TMSCl=trimethylsilyl chloride. HF=hydrofluoric acid. THF=tetrahydrofuran. MeTHF=2-Methyltetrahydrofuran. G=Guanine. $G^{ib}$=isobutyryl guanine. A=adenine. $A^{Bz}$=benzoyl adenine. AMA=ammonium hydroxide/40% methylamine solution in water. Rt=retention time. rt=room temperature. min=minute(s). h=hour(s).

Example 1

Synthesis of Intermediate Compounds

The LCMS or HRMS data in this example, and where indicated in the following examples, were recorded using the indicated methods as follows. In all instances, masses reported are those of the protonated parent ions unless indicated otherwise.

Method A: LCMS data were recorded using a Waters System: Micromass ZQ mass spectrometer; Column: Sunfire C18 3.5 micron, 3.0×30 mm; gradient: 40-98% MeCN in water with 0.05% TFA over a 2.0 min period; flow rate 2 mL/min; column temperature 40° C.).

Method B: LCMS were recorded using a Waters System: Micromass SQ mass spectrometer; Column: Acquity UPLC BEH C18 1.7 micron, 2.1×30 mm; gradient 1% to 30% MeCN to 3.20 min then gradient: 30-98% MeCN in water with 5 mM $NH_4OH$ over a 1.55 min period before returning to 1% MeCN at 5.19 min-total run time 5.2 min; flow rate 1 mL/min; column temperature 50° C.

Method C: LCMS were recorded using a Waters System: Micromass SQ mass spectrometer; Column: Acquity UPLC BEH C18 1.7 micron, 2.1×50 mm; gradient: 2-98% MeCN in water+5 mM $NH_4OH$ over a 4.40 min period isocratic for 0.65 min before returning to 2% MeCN at 5.19 min-total run time 5.2 min; flow rate 1 mL/min; column temperature 50° C.

Method E: HRMS data were recorded using a Waters System: Acquity G2 Xevo QTof mass spectrometer; Column: Acquity BEH 1.7 micron, 2.1×50 mm; gradient: 40-98% MeCN in water with 0.1% Formic acid over a 3.4 min period, isocratic 98% MeCN for 1.75 mins returning to 40% at 5.2 mins; flow rate 1 mL/min; column temperature 50° C.

Method G: LCMS data were recorded using a Waters System: Micromass SQ mass spectrometer; Column: Acquity UPLC BEH C18 1.7 micron, 2.1×30 mm; gradient 1% to 30% MeCN to 1.20 mins then gradient: 30-98% MeCN in water with 5 mM $NH_4OAc$ over a 0.55 min period before returning to 1% MeCN at 2.19 mins-total run time 2.2 mins; flow rate 1 mL/min; column temperature 50° C.

Method H: LCMS data were recorded using a Waters System: Micromass SQ mass spectrometer; Column: Acquity UPLC BEH C18 1.7 micron, 2.1×30 mm; gradient 2% to 98% MeCN to 1.76 mins then isocratic to 2.00 mins and then returning to 2% MeCN using gradient to 2.20 mins in water with 0.1% Formic acid; flow rate 1 mL/min; column temperature 50° C.

Method I: LCMS data were recorded using a Waters System: Micromass SQ mass spectrometer; Column: Acquity UPLC BEH C18 1.7 micron, 2.1×30 mm; gradient 40% to 98% MeCN to 1.40 mins then isocratic to 2.05 mins and then returning to 40% MeCN using gradient to 2.20 mins in water with 0.1% Formic acid; flow rate 1 mL/min; column temperature 50° C.

Intermediate i6 (used in Example 2) was prepared according to the following Scheme 1A:
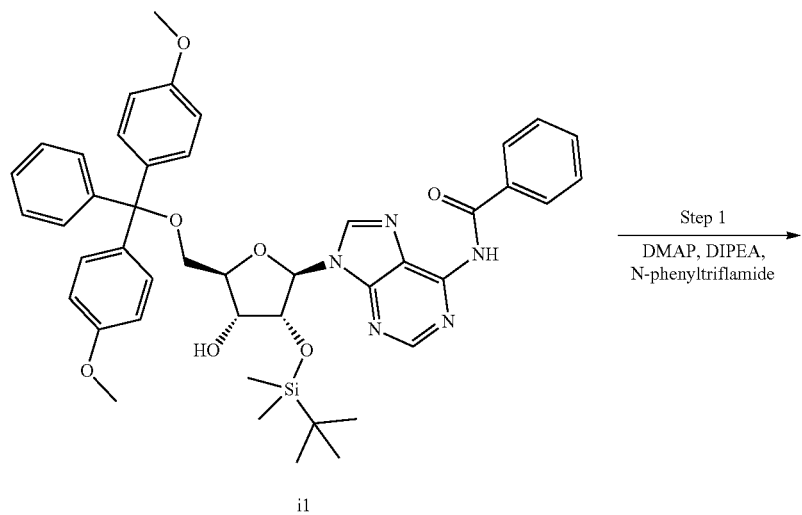
i1
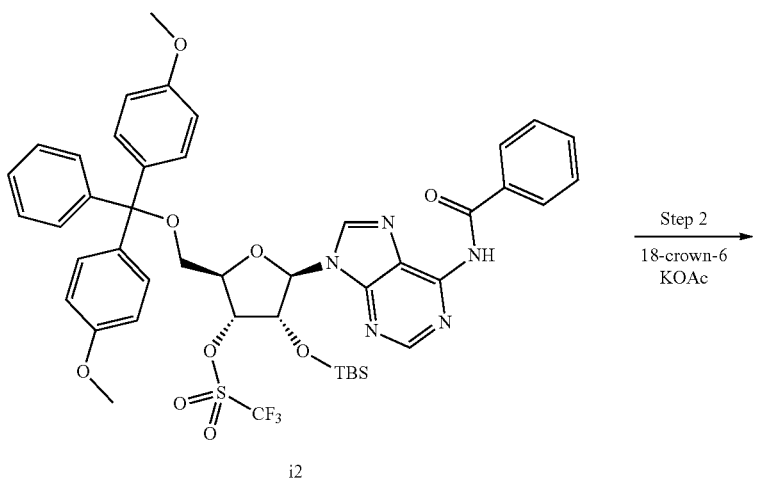
i2
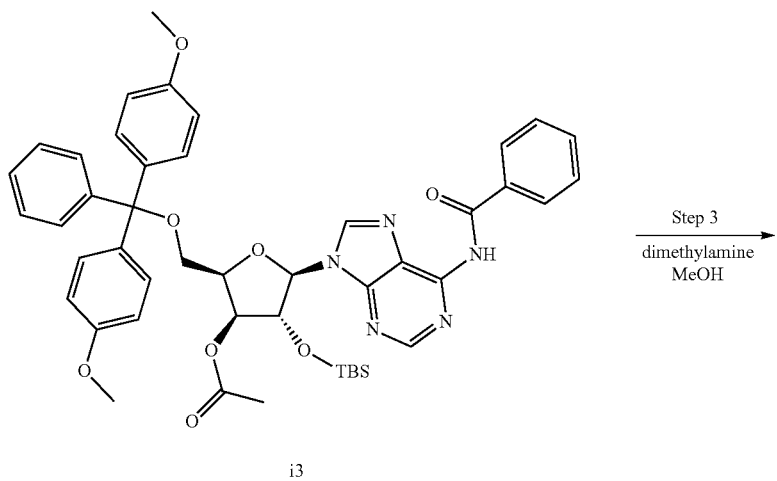
i3

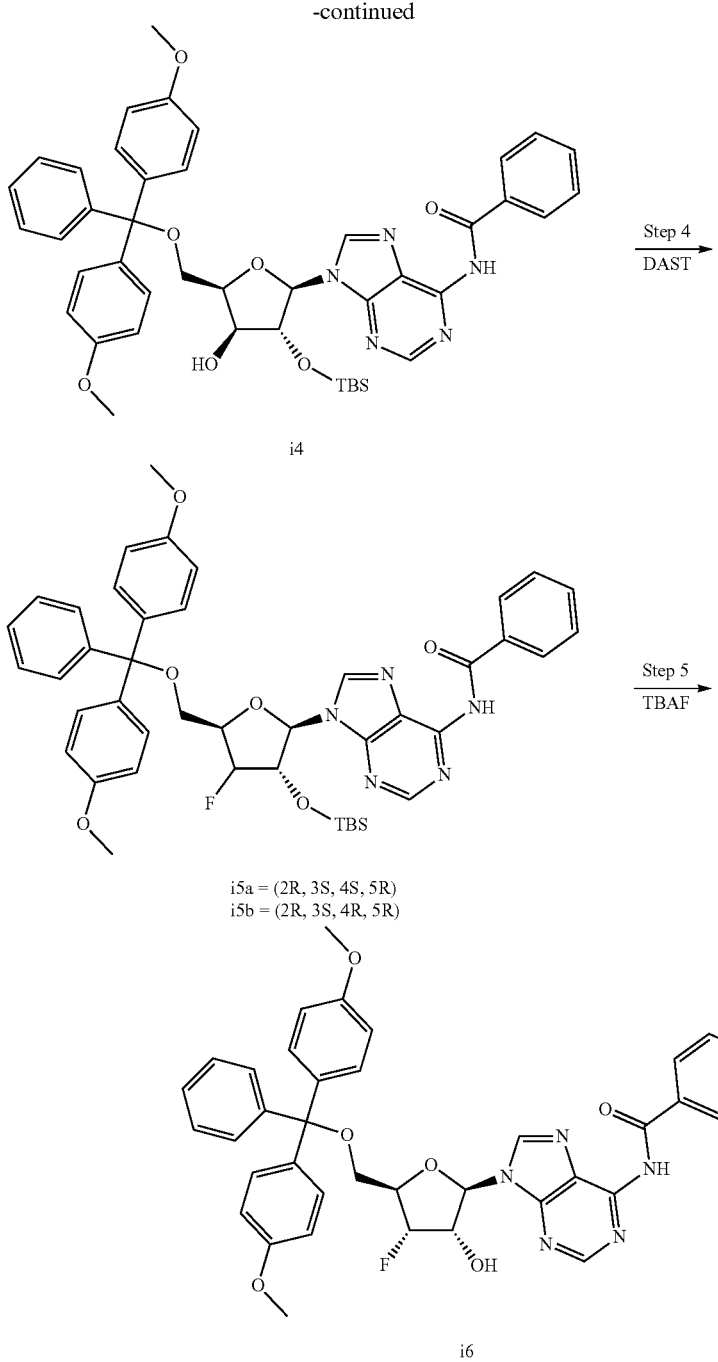

i5a = (2R, 3S, 4S, 5R)
i5b = (2R, 3S, 4R, 5R)

Step 1: Preparation of (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yltrifluoromethane-sulfonate (i2): A mixture of N-(9-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl)benzamide (i1, 5.6 g, 7.11 mmol, ChemGenes) and DMAP (0.174 g, 1.42 mmol) was suspended in anhydrous THF (35 mL), addition of DIPEA (6.21 mL, 35.5 mmol) created a solution to which N-phenyltriflamide (5.08 g, 14.21 mmol), was added. The mixture was stirred for 3.5 h at rt, at which point it was poured into 5% brine (100 mL) and extracted with EtOAc (2×100 mL). The combined organic phases were dried (Na$_2$SO$_4$) the drying agent filtered-off and concentrated on silica gel (10 g) in vacuo. The crude material was purified by chromatography on silica gel (gradient elution 25-100% EtOAc/heptane) to give the desired compound i2 as a tan solid; 5.53 g; $^1$H NMR (400 MHz, CDCl$_3$) δ 9.05 (s, 1H), 8.68 (s, 1H), 8.18 (s, 1H), 8.06 (d, J=7.5 Hz, 2H), 7.66 (t, J=7.4 Hz, 1H), 7.61-7.48 (m, 4H), 7.48-7.25 (m, 7H), 6.88 (d, J=8.8 Hz, 4H), 6.04 (d, J=7.6 Hz, 1H), 5.50 (dd, J=7.5, 4.7 Hz, 1H), 5.32 (d, J=4.5 Hz, 1H), 4.50 (t, J=4.1 Hz, 1H), 3.82 (s, 6H), 3.77 (dt, J=10.8, 5.2 Hz, 1H), 3.41 (dd, J=10.8, 3.7 Hz, 1H), 0.77 (s, 9H), −0.01 (s, 3H), −0.46 (s, 3H); LCMS (Method A) R$_t$=1.65 min; m/z 920.5 [M+H]$^+$.

Step 2: Preparation of (2R,3S,4R,5R)-5-(6-benzamido-9H-purin-9-yl)-2-((bis(4-methoxyphenyl)(phenyl)methoxy)methyl)-4-((tert-butyldimethylsilypoxy)tetrahydrofuran-3-yl acetate (i3): A mixture of compound i2 (5.5 g, 5.98 mmol), KOAc (2.93 g, 29.9 mmol), and 18-crown-6 (1,4,7,10,13,16-hexaoxacyclooctadecane, 0.79 g, 2.99 mmol) in toluene (40 mL) was heated at 110° C. for 4 h. The reaction mixture was then cooled to rt and silica gel (10 g) added and the solvent was removed in vacuo. The crude material was purified by chromatography on silica gel (gradient elution 25-100% EtOAc/heptane) to give the desired compound i3 as a tan solid: 3.3 g; $^1$H NMR (400 MHz, CDCl$_3$) δ 8.70 (s, 1H), 8.58 (s, 1H), 7.93 (s, 1H), 7.84 (d, J=7.5 Hz, 2H), 7.44 (t, J=7.4 Hz, 1H), 7.35 (t, J=7.6 Hz, 2H), 7.28 (d, J=7.2 Hz, 2H), 7.21-7.02 (m, 7H), 6.67 (dd, J=8.9, 2.1 Hz, 4H), 5.98 (s, 1H), 4.97 (dd, J=3.6, 1.4 Hz, 1H), 4.61-4.52 (m, 1H), 4.35 (s, 1H), 3.62 (s, 6H), 3.41 (dd, J=9.8, 6.2 Hz, 1H), 3.18 (dd, J=9.8, 5.6 Hz, 1H), 1.53 (s, 3H), 0.77 (s, 9H), 0.03 (s, 3H), 0.0 (s, 3H). LCMS (Method A) R$_t$ 1.68 min; m/z 830.2 [M+H]$^+$.

Step 3: Preparation of N-(9-((2R,3R,4S,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl)benzamide (i4): Compound i3 (6.78 g, 8.17 mmol) was dissolved in MeOH (120 mL) and a 2.0 M dimethylamine solution in MeOH (20.4 mL, 40.8 mmol) was added. The reaction mixture was stirred for 17 h at rt. Silica gel (12 g) was added and the solvent was removed in vacuo. The crude material was purified by chromatography on silica gel (gradient elution 25-75% EtOAc/heptane) to give the desired compound i4 as a tan solid: 3.9 g; $^1$H NMR (400 MHz, CDCl$_3$) δ 8.94 (s, 1H), 8.65 (s, 1H), 8.16 (s, 1H), 7.97-7.90 (m, 2H), 7.58-7.38 (m, 3H), 7.38-7.32 (m, 2H), 7.32-7.00 (m, 7H), 6.80-6.65 (m, 4H), 5.83 (d, J=1.2 Hz, 1H), 5.38 (d, J=8.0 Hz, 1H), 4.42 (s, 1H), 4.29 (t, J=4.6 Hz, 1H), 4.02-3.95 (m, 1H), 3.75-3.61 (m, 6H), 3.53 (d, J=5.0 Hz, 2H), 0.81 (s, 9H), 0.0 (s, 6H). LCMS (Method A) R$_t$ 1.57 min; m/z 788.2 [M+H]$^+$.

Step 4: Preparation of N-(9-((2R,3S,4S,5R)-5-((bis(4-methoxyphenyl)(phenyl)methoxy)methyl)-3-((tert-butyldimethylsilyl)oxy)-4-fluorotetrahydrofuran-2-yl)-9H-purin-6-yl)benzamide (i5a) and N-(9-((2R,3S,4R,5R)-5-((bis(4-methoxyphenyl)(phenyl)methoxy)methyl)-3-((tert-butyldimethylsilypoxy)-4-fluorotetrahydrofuran-2-yl)-9H-purin-6-yl)benzamide (i5b): Compound i4 (750 mg, 0.952 mmol) was dissolved in anhydrous DCM (7 mL) under an inert nitrogen atmosphere and the solution was cooled to 0° C. A 1.0 M solution of DAST (1.90 mL, 1.90 mmol) was added and the reaction subsequently stirred at −5° C. for 17 h using a cryo-cool to control the reaction temperature. The vessel was warmed to 0° C. and saturated NaHCO$_3$ (2 mL) was added. After 30 min of stirring the mixture was diluted with 5% brine (20 mL) and extracted with EtOAc (2×20 mL). The combined organics were dried (Na$_2$SO$_4$) with the drying agent filtered off, silica gel (2 g) added to the filtrate and the solvent removed in vacuo. The crude material was purified by chromatography on silica gel (gradient elution 10-75% EtOAc/heptane) to give a mixture of diastereoisomers i5a and i5b as a tan solid:193 mg; Major (2R,3S,4S,5R) diastereoisomer LCMS (Method A) R$_t$ 1.53 min; m/z 790.4 (M+H)$^+$; Minor (2R,3S,4R,5R) diastereoisomer R$_t$ 1.58 min; m/z 790.4 [M+H]$^+$.

Step 5: Preparation of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6): The diastereomeric mixture of i5a and i5b (2.0 g, 2.53 mmol) was dissolved in anhydrous THF (100 mL) and cooled to −42° C. under an inert nitrogen atmosphere before 1.0 M TBAF (3.80 mL, 3.80 mmol) was added. The reaction was stirred for 2.5 h, then quenched with saturated NaHCO$_3$ (20 mL). The cold bath was removed, and the slurry was stirred for 10 min before the mixture was diluted with 5% brine (150 mL) and extracted with DCM (2×100 mL). The combined organic phases were dried (Na$_2$SO$_4$), with the drying agent filtered off, silica gel (4 g) added to the filtrate and the solvent removed in vacuo. The crude material was purified by chromatography on silica gel (gradient elution 25-100% EtOAc/heptane) to give the desired compound i6 as a white solid: 355 mg; $^1$H NMR (400 MHz, CDCl$_3$) δ 9.16 (s, 1H), 8.64 (s, 1H), 8.23 (s, 1H), 7.99 (d, J=7.5 Hz, 2H), 7.59 (t, J=7.4 Hz, 1H), 7.48 (t, J=7.6 Hz, 2H), 7.41-7.31 (m, 3H), 7.31-7.11 (m, 7H), 6.79 (d, J=8.9 Hz, 4H), 6.16 (d, J=7.3 Hz, 1H), 5.77 (br s, 1H), 5.27-5.10 (m, 2H), 4.53 (dt, J=28.0 Hz, 3.4 Hz, 1H), 3.77 (s, 6H), 3.51 (dd, J=10.7, 3.7 Hz, 1H), 3.34 (dd, J=10.7, 3.3 Hz, 1H); $^{19}$F NMR (376.4 MHz, CDCl$_3$) δ-197.5; $^{13}$C NMR (101 MHz, CDCl$_3$) δ 164.66, 158.64, 158.62, 152.60, 151.43, 149.34, 144.22, 141.66, 135.29, 135.13, 133.40, 132.93, 129.96, 128.87, 127.99, 127.93, 127.86, 127.07, 122.65, 113.26, 93.85, 92.02, 87.56 (d, J=144 Hz), 83.56 (d, J=23 Hz), 77.30, 74.63 (d, J=16 Hz), 62.82 (d, J=11 Hz), 55.26; LCMS (Method A) R$_t$ 0.89 min; m/z 676.3 [M+H]$^+$.

Alternatively, Intermediate i6 was also prepared according to the following Scheme 1A':

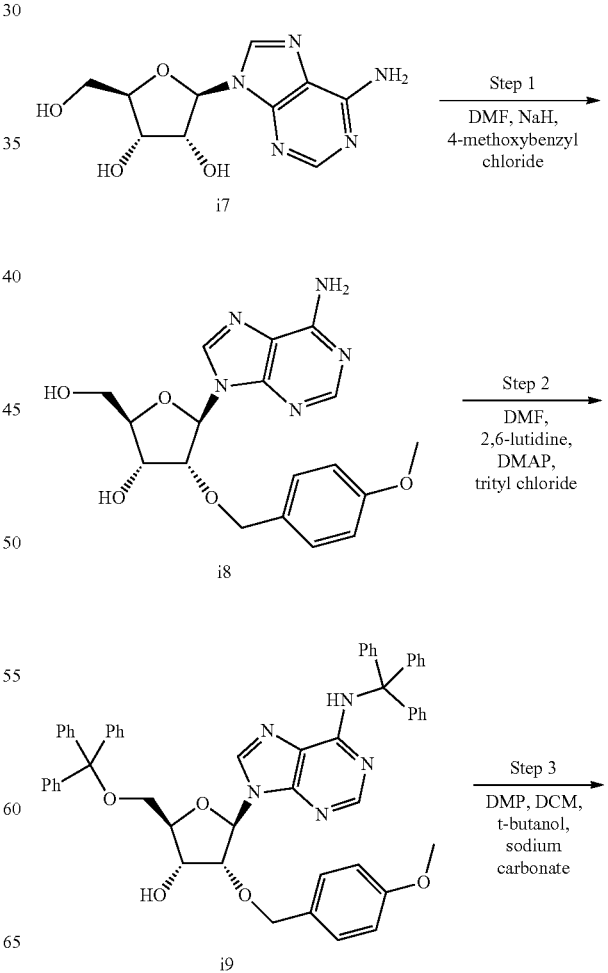

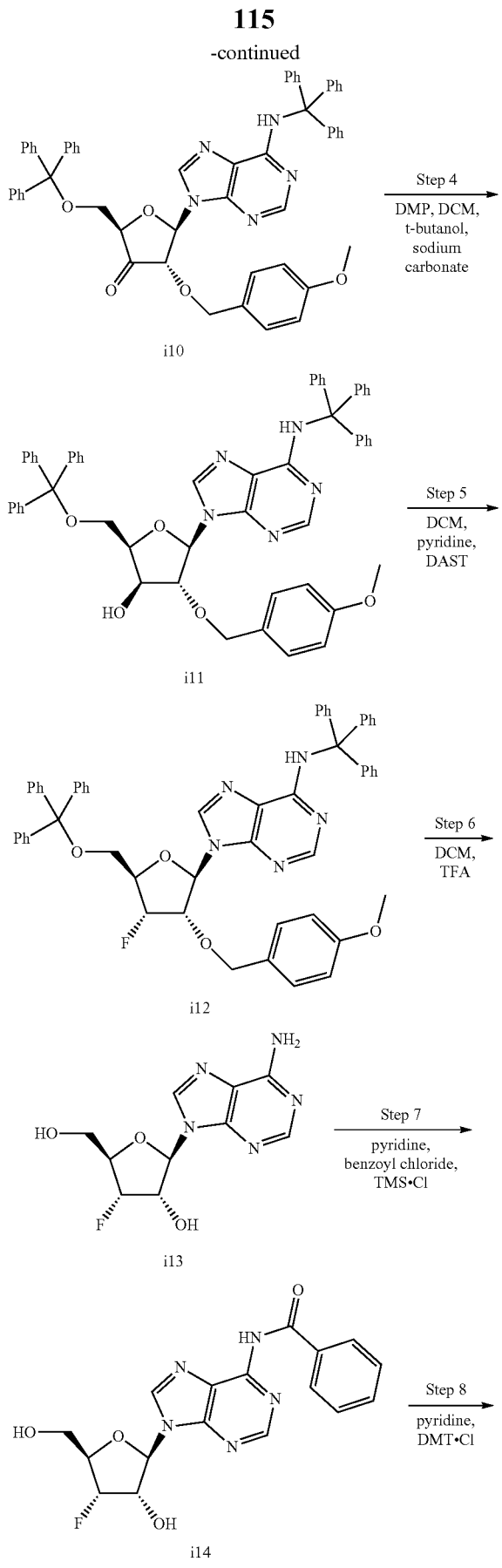

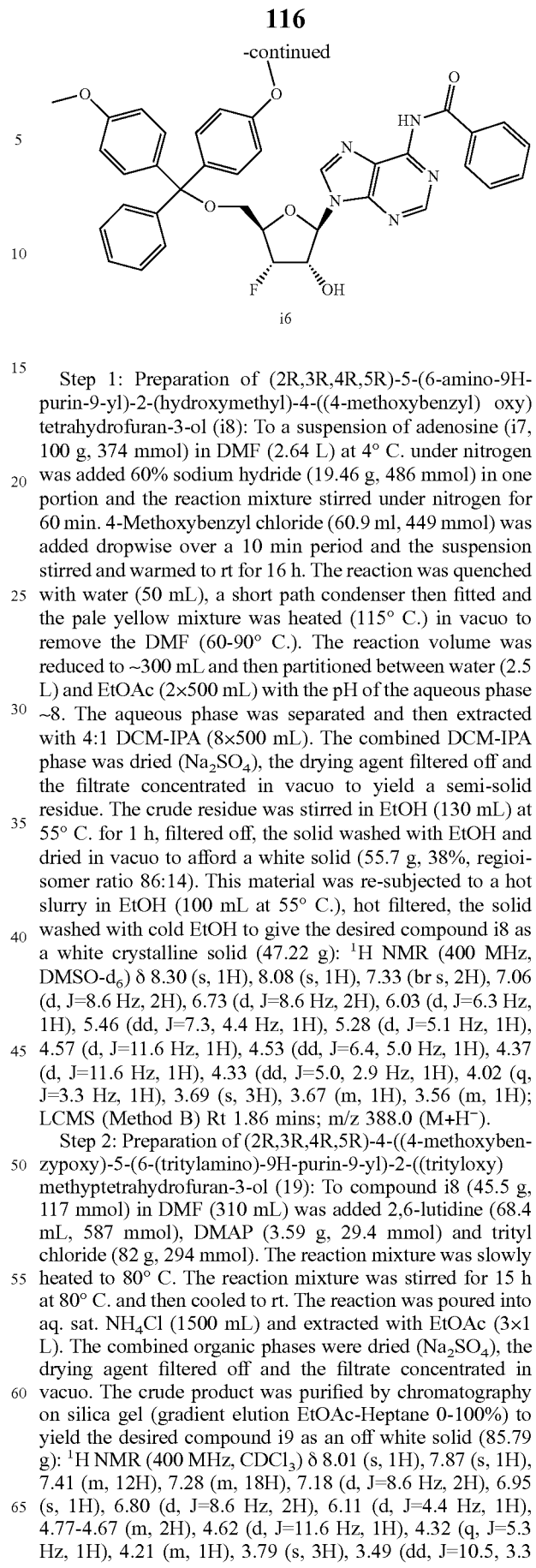

Step 1: Preparation of (2R,3R,4R,5R)-5-(6-amino-9H-purin-9-yl)-2-(hydroxymethyl)-4-((4-methoxybenzyl) oxy)tetrahydrofuran-3-ol (i8): To a suspension of adenosine (i7, 100 g, 374 mmol) in DMF (2.64 L) at 4° C. under nitrogen was added 60% sodium hydride (19.46 g, 486 mmol) in one portion and the reaction mixture stirred under nitrogen for 60 min. 4-Methoxybenzyl chloride (60.9 ml, 449 mmol) was added dropwise over a 10 min period and the suspension stirred and warmed to rt for 16 h. The reaction was quenched with water (50 mL), a short path condenser then fitted and the pale yellow mixture was heated (115° C.) in vacuo to remove the DMF (60-90° C.). The reaction volume was reduced to ~300 mL and then partitioned between water (2.5 L) and EtOAc (2×500 mL) with the pH of the aqueous phase ~8. The aqueous phase was separated and then extracted with 4:1 DCM-IPA (8×500 mL). The combined DCM-IPA phase was dried (Na$_2$SO$_4$), the drying agent filtered off and the filtrate concentrated in vacuo to yield a semi-solid residue. The crude residue was stirred in EtOH (130 mL) at 55° C. for 1 h, filtered off, the solid washed with EtOH and dried in vacuo to afford a white solid (55.7 g, 38%, regioisomer ratio 86:14). This material was re-subjected to a hot slurry in EtOH (100 mL at 55° C.), hot filtered, the solid washed with cold EtOH to give the desired compound i8 as a white crystalline solid (47.22 g): $^1$H NMR (400 MHz, DMSO-d$_6$) δ 8.30 (s, 1H), 8.08 (s, 1H), 7.33 (br s, 2H), 7.06 (d, J=8.6 Hz, 2H), 6.73 (d, J=8.6 Hz, 2H), 6.03 (d, J=6.3 Hz, 1H), 5.46 (dd, J=7.3, 4.4 Hz, 1H), 5.28 (d, J=5.1 Hz, 1H), 4.57 (d, J=11.6 Hz, 1H), 4.53 (dd, J=6.4, 5.0 Hz, 1H), 4.37 (d, J=11.6 Hz, 1H), 4.33 (dd, J=5.0, 2.9 Hz, 1H), 4.02 (q, J=3.3 Hz, 1H), 3.69 (s, 3H), 3.67 (m, 1H), 3.56 (m, 1H); LCMS (Method B) Rt 1.86 mins; m/z 388.0 (M+H$^-$).

Step 2: Preparation of (2R,3R,4R,5R)-4-((4-methoxybenzypoxy)-5-(6-(tritylamino)-9H-purin-9-yl)-2-((trityloxy)methyptetrahydrofuran-3-ol (19): To compound i8 (45.5 g, 117 mmol) in DMF (310 mL) was added 2,6-lutidine (68.4 mL, 587 mmol), DMAP (3.59 g, 29.4 mmol) and trityl chloride (82 g, 294 mmol). The reaction mixture was slowly heated to 80° C. The reaction mixture was stirred for 15 h at 80° C. and then cooled to rt. The reaction was poured into aq. sat. NH$_4$Cl (1500 mL) and extracted with EtOAc (3×1 L). The combined organic phases were dried (Na$_2$SO$_4$), the drying agent filtered off and the filtrate concentrated in vacuo. The crude product was purified by chromatography on silica gel (gradient elution EtOAc-Heptane 0-100%) to yield the desired compound i9 as an off white solid (85.79 g): $^1$H NMR (400 MHz, CDCl$_3$) δ 8.01 (s, 1H), 7.87 (s, 1H), 7.41 (m, 12H), 7.28 (m, 18H), 7.18 (d, J=8.6 Hz, 2H), 6.95 (s, 1H), 6.80 (d, J=8.6 Hz, 2H), 6.11 (d, J=4.4 Hz, 1H), 4.77-4.67 (m, 2H), 4.62 (d, J=11.6 Hz, 1H), 4.32 (q, J=5.3 Hz, 1H), 4.21 (m, 1H), 3.79 (s, 3H), 3.49 (dd, J=10.5, 3.3

Hz, 1H), 3.36 (dd, J=10.5, 4.5 Hz, 1H), 2.66 (d, J=5.7 Hz, 1H); LCMS (Method G) Rt 1.53 mins; m/z 872.0 (M+H⁺).

Step 3: Preparation of (2R,4S,5R)-4-((4-methoxybenzypoxy)-5-(6-(tritylamino)-9H-purin-9-yl)-2-((trityloxy)methyl)dihydrofuran-3(2H)-one (i10): To a solution of Dess-Martin Periodinane (DMP, 3.04 g, 7.17 mmol) in DCM (72 mL) at rt was added tert-butanol (0.713 mL, 7.45 mmol) and sodium carbonate (0.134 g, 1.261 mmol), followed by a dropwise addition over 1 h of a solution of compound i9 (5.00 g, 5.73 mmol) in DCM (72 mL). The resulting reaction mixture was stirred at rt for 4 h before additional DCM (110 mL) was added. After a further 3 h additional DMP (0.63 g) and DCM (50 mL) were added. The reaction stirred for 13 h and then quenched by addition of sat. Na₂S₂O₅ (40 mL), sat. NaHCO₃ (150 mL) and brine (50 mL). The organic phase was separated and the aqueous phase then re-extracted with DCM (2×150 mL). The combined DCM was dried (Na₂SO₄), the drying agent filtered off and the filtrate concentrated in vacuo. The crude material was purified by chromatography on silica gel (gradient elution EtOAc/heptane (0-80%) to afford compound i10 as a white foam (4.36 g): ¹H NMR (400 MHz, CDCl₃) δ 7.95 (s, 1H), 7.78 (s, 1H), 7.46-7.15 (m, 30H), 7.05 (d, J=8.6 Hz, 2H), 6.98 (s, 1H), 6.73 (d, J=8.6 Hz, 2H), 6.13 (d, J=7.8 Hz, 1H), 5.23 (dd, J=7.9, 0.8 Hz, 1H), 4.80 (d, J=11.8 Hz, 1H), 4.72 (d, J=11.8 Hz, 1H), 4.35 (ddd, J=4.0, 2.4, 0.8 Hz, 1H), 3.76 (s, 3H), 3.52 (dd, J=10.5, 4.0 Hz, 1H), 3.43 (dd, J=10.5, 2.4 Hz, 1H); LCMS (Method C) Rt 1.53 mins; m/z 870.0 (M+H⁻).

Step 4: Preparation of (2R,3S,4R,5R)-4-((4-methoxybenzypoxy)-5-(6-(tritylamino)-9H-purin-9-yl)-2-((trityloxy)methyptetrahydrofuran-3-ol (i11): To a solution of compound i10 (98 mg, 0.113 mmol) in DCM (3 mL) at −20° C. was added glacial AcOH (0.15 mL) followed by NaBH₄ (13 mg, 0.34 mmol). After 1 h the reaction mixture was quenched with 5% brine (20 mL) and extracted with EtOAc (25 mL). The organic phase was separated and dried (Na₂SO₄), the drying agent filtered off and the filtrate concentrated in vacuo to a white solid. The crude solid (3S:3R ratio 7:1) was slurried in hot MeOH (3 mL, warmed to 50° C.) with DCM (~0.5 mL) added dropwise and the suspension cooled. The mother liquor was decanted off and the solid was dried in vacuo (63 mg, 3S:3R ratio 13:1). Recrystallization from MeOH:DCM (4 mL, v/v 5:1) gave compound i11 as a single diastereomer (ratio 50:1): ¹H NMR (400 MHz, CDCl₃) δ 7.90 (s, 1H), 7.74 (s, 1H), 7.48-7.13 (m, 32H), 6.95-6.84 (m, 2H), 5.80 (s, 1H), 4.68 (d, J 11.3 Hz, 1H), 4.49 (d, J11.3 Hz, 1H), 4.36 (s, 1H), 4.33-4.27 (m, 1H), 4.23 (d, J3 Hz, 1H), 3.83 (s, 3H), 3.59-3.52 (m, 2H); LCMS (Method H) Rt 1.76 mins; m/z 872.2 (M+H)⁺.

Step 5: Preparation of 9-((2R,3S,4R,5R)-4-fluoro-3-((4-methoxybenzypoxy)-5-((trityloxy)methyptetrahydro-furan-2-yl)-N-trityl-9H-purin-6-amine (i12): To a solution of compound i11 (240 mg, 0.275 mmol) in anhydrous DCM (15 mL) at 0° C. was added anhydrous pyridine (0.223 mL, 2.75 mmol). After 5 min, diethylaminosulfur trifluoride (DAST, 0.182 mL, 1.38 mmol) was added dropwise. After 5 min, the cooling bath was removed and the reaction stirred for 4.5 h. The reaction mixture was diluted with chloroform (20 mL), dry silica gel was added, and the mixture concentrated in vacuo before adding toluene (20 mL) and concentrating to dryness in vacuo. The crude material was purified by chromatography on silica gel (gradient elution 10-50% EtOAc/heptane) to give the desired compound i12 as a white solid (121 mg): ¹H NMR (400 MHz, CDCl₃) δ 7.93 (s, 1H), 7.82 (s, 1H), 7.42-7.20 (m, 30H), 7.13-7.05 (m, 3H), 6.74 (d, J 8.3 Hz, 2H), 6.09-6.05 (m, 1H), 5.15-5.06 (m, 1H), 5.00 (dd, J 54.4, and 4.4 Hz, 1H), 4.60-4.50 (m, 2H), 4.49-4.39 (m, 1H), 3.77 (s, 3H), 3.51-3.38 (m, 1H), 3.32 (dd, J=10.6, 4.0 Hz, 1H); ¹⁹F NMR (376.4 MHz, CDCl₃) δ−198.09; LCMS (Method I) Rt 1.27 mins; m/z 874.5 (M+H)⁺.

Step 6: Preparation of (2R,3S,4S,5R)-2-(6-amino-9H-purin-9-yl)-4-fluoro-5-(hydroxymethyl)tetrahydrofuran-3-ol (i13): To a solution of compound i12 (70 mg, 0.080 mmol) in DCM (1 mL) was added TFA (0.5 mL, 6.49 mmol). After 45 min the reaction mixture was diluted with MeOH (10 mL) and concentrated in vacuo. The crude material was dissolved in MeOH (10 mL) and TEA (0.1 mL) was added before silica gel was added and the suspension concentrated in vacuo. The crude material was purified by chromatography on silica gel (gradient elution 0-10% MeOH/DCM) to give the desired compound i13 as a white solid (21 mg) containing TEA.TFA salt and used as is: ¹H NMR (400 MHz, Methanol-d₄) δ 8.33 (s, 1H), 8.21 (s, 1H), 6.02 (d, J7.9 Hz, 1H), 5.12 (dd, J54.5, 4.3 Hz, 1H), 4.96 (ddd, J25.1, 8.0, 4.3 Hz, 1H), 4.44 (dt, J27.6, 2.5 Hz, 1H), 3.94-3.69 (m, 2H); ¹⁹F NMR (376.4 MHz, Methanol-d₄) δ−200.02; LCMS (Method G) Rt 0.51 mins; m/z 270.1 (M+H)⁺.

Step 7: Preparation of N-(9-((2R,3S,4S,5R)-4-fluoro-3-hydroxy-5-(hydroxymethyptetrahydrofuran-2-yl)-9H-purin-6-yl)benzamide (114): To compound i13 (3.88 g, 14.41 mmol) in pyridine (65 mL) at 0° C. was added benzoyl chloride (8.36 mL, 72.1 mmol) slowly followed by TMSCl (9.21 mL, 72.1 mmol). The reaction mixture was stirred while warming to rt for 4 h. After another 1 h the solution was quenched with water (35 mL), followed by conc. NH₄OH (17 mL) after 5 min resulting in a pale tan solid. The mixture was diluted with water (100 mL) and extracted with MeTHF (3×75 mL). The combined organic phases were dried (Na₂SO₄), the drying agent filtered off and the filtrate concentrated in vacuo to a tan semi-solid crude material, which was purified by chromatography on silica gel (gradient elution 0-20% MeOH/DCM) to give the desired compound i14 (2.75 g): ¹H NMR (400 MHz, CDCl₃) δ 8.78 (s, 1H), 8.09 (s, 1H), 8.08-8.01 (m, 2H), 7.66 (t, J=7.4 Hz, 1H), 7.57 (t, J=7.5 Hz, 2H), 6.13 (br s, 1H), 5.92 (d, J=7.9 Hz, 1H), 5.41-5.11 (m, 2H), 4.60 (d, J=28.4 Hz, 1H), 4.13-3.98 (m, 2H), 3.86 (d, J=13.0 Hz, 1H). ¹⁹F NMR (376.4 MHz, CDCl₃) δ−199.36; LCMS (Method G) Rt 0.72 mins; m/z 374.2 (M+H)⁺.

Step 8: Preparation of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (16): To compound i14 (2.73 g, 10.14 mmol) in pyridine (55 mL) was added DMTCl (4.12 g, 12.17 mmol) in one portion. The reaction was stirred at rt for 72 h before the yellowish solution was quenched by addition of MeOH (20 mL) and then concentrated in vacuo to a semi-solid following addition of toluene (2×50 mL) to azeotrope residual pyridine. The resulting material was dissolved in DCM (100 mL), washed with sat. NaHCO₃ (100 mL), brine then dried (Na₂SO₄). The drying agent was filtered off and the filtrate evaporated in vacuo. The resulting residue was purified by chromatography on silica gel (gradient elution 0-10% MeOH/DCM with 0.04% TEA) to give compound i6 as a white solid (3.70 g): ¹H NMR (400 MHz, CDCl₃) δ 9.16 (s, 1H), 8.64 (s, 1H), 8.23 (s, 1H), 7.99 (d, J 7.5 Hz, 2H), 7.59 (t, J 7.4 Hz, 1H), 7.48 (t, J 7.6 Hz, 2H), 7.41-7.31 (m, 3H), 7.31-7.11 (m, 7H), 6.79 (d, J8.9 Hz, 4H), 6.16 (d, J 7.3 Hz, 1H), 5.77 (br s, 1H), 5.27-5.10 (m, 2H), 4.53 (dt, J 28.0 Hz, 3.4 Hz, 1H), 3.77 (s, 6H), 3.51 (dd, J 10.7, 3.7 Hz, 1H), 3.34 (dd, J 10.7, 3.3 Hz, 1H); ¹⁹F NMR (376.4 MHz, CDCl₃) δ−197.5; ¹³C NMR (101 MHz, CDCl₃) δ 164.66, 158.64, 158.62, 152.60, 151.43, 149.34, 144.22, 141.66, 135.29, 135.13, 133.40, 132.93, 129.96, 128.87, 127.99, 127.93, 127.86, 127.07, 122.65, 113.26, 93.85, 92.02, 87.56 (d, J 144 Hz), 83.56 (d, J 23 Hz), 77.30, 74.63 (d, J 16 Hz), 62.82 (d, J 11 Hz), 55.26; LCMS (Method C) Rt 2.72 mins; m/z 676.3 (M+H)+.
Example 2
Synthesis of 2'2'-RR-(3'F-A)(3'F-A) (8)
(1S,3R,6R,8R,9S,11R,14R,16R,17R,18R)-8,16-bis(6-amino-9H-purin-9-yl)-17,18-difluoro-3,11-dimercapto-2,4,7,10,12,15-hexaoxa-3,11-diphosphatricyclo[12.2.1.1$^{6,9}$]octadecane 3,11-dioxide (8) also referred to as 2'2'-RR-(3'F-A)(3'F-A), bis 2'-5'-RR-(3'F-A)(3'F-A), or dithio-(Rp,Rp)-cyclic-[3'F-A(2',5')p-3'F-A(2',5')p], was prepared according to the following Scheme 2:
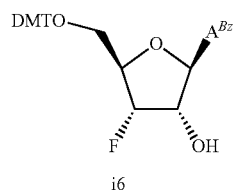
i6
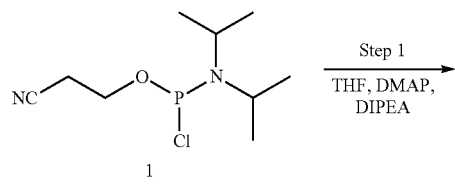
1
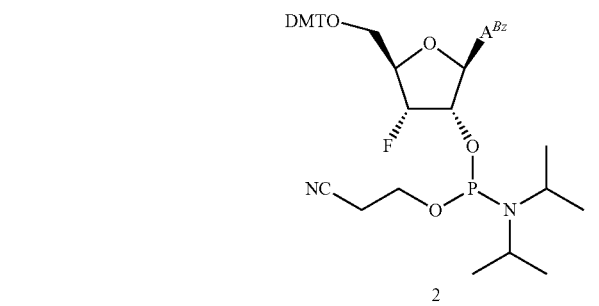
2
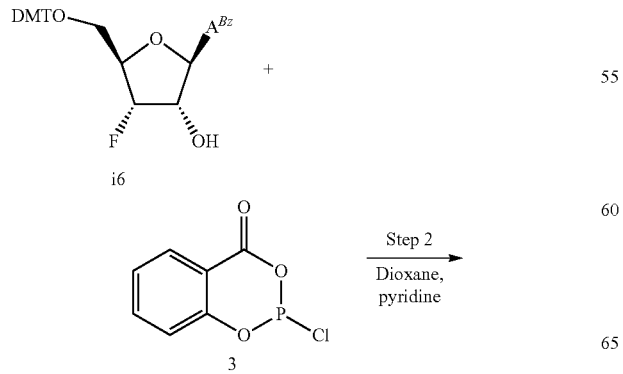
3
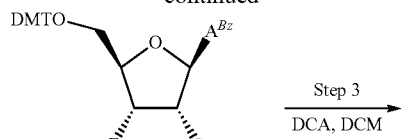
4
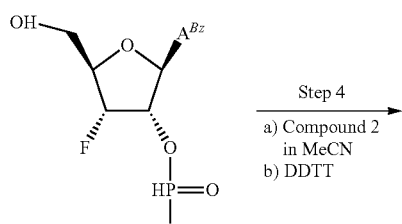
5
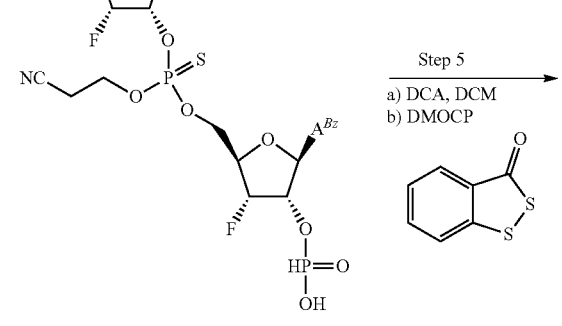
6
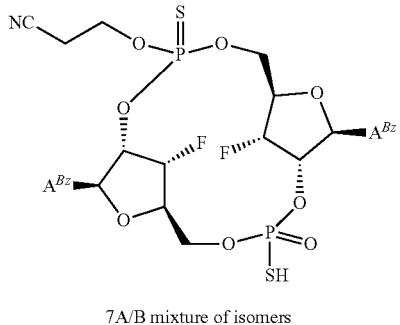
7A/B mixture of isomers
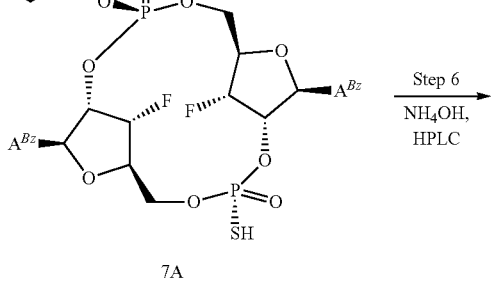
7A -continued

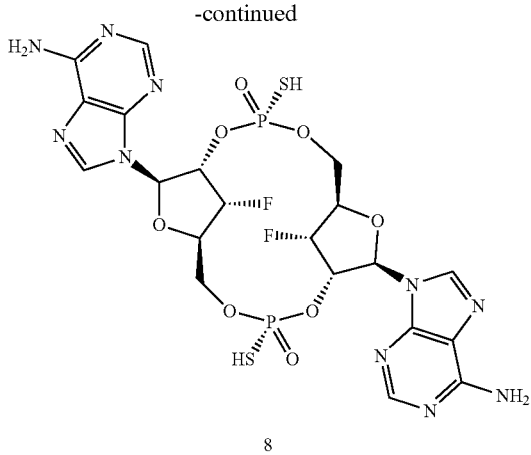

8

Step 1: Preparation of (2R,3S,4R,5R)-2-(6-benzamido-9H-purin-9-yl)-5-((bis(4-methoxyphenyl)(phenyl)methoxy)methyl)-4-fluorotetrahydrofuran-3-yl (2-cyanoethyl) diisopropylphosphoramidite (2): To a solution of Compound i6 (1, 1 g, 1.5 mmol, 1 eq) (dried via co-evaporation in vacuo with anhydrous MeCN (3×3 mL)) in anhydrous THF (6 mL) was added DMAP (18 mg, 0.15 mmol, 0.1 eq) and DIPEA (0.98 mL, 5.9 mmol, 4 eq). 2-cyanoethyl N,N-diisopropyl chlorophosphoramidite (360 µL, 1.6 mmol, 1.1 eq, ChemGenes) was added and the reaction was stirred overnight. The mixture was diluted with 100 mL of EtOAc (prewashed with 5% NaHCO$_3$) and washed with brine (5×50 mL). The EtOAc layer dried over Na$_2$SO$_4$, filtered and concentrated in vacuo. Flash chromatography (40 g silica gel, isocratic gradient-50:44:4 DCM:Hexanes:TEA) gave 1.08 g of the compound 2.

Step 2: Preparation of (2R,3S,4R,5R)-2-(6-benzamido-9H-purin-9-yl)-5-((bis(4-methoxyphenyl)(phenyl)methoxy)methyl)-4-fluorotetrahydrofuran-3-yl hydrogen phosphonate (4): To a solution of Compound i6 (1.5 g, 2.7 mmol, 1 eq) in anhydrous dioxane (17 mL) was added anhydrous pyridine (4.7 mL, 69 mmol, 26 eq) followed by a solution of 2-chloro-1,3,2-benzodioxaphosphorin-4-one (3, 540 mg, 3.2 mmol, 1.2 eq, Sigma Aldrich) in 1,4-dioxane (8.3 mL). The reaction mixture was stirred for 1 h then diluted with 10 mL water and NaHCO$_3$ (3.72 g in 100 mL of water). The suspension was extracted with EtOAc (3×100 mL), the organic layers were combined, dried with Na$_2$SO$_4$, filtered and concentrated. Chromatography (80 g of SiO$_2$, 0-50% MeOH (with 0.5% pyridine) and DCM) gave compound 4.

Step 3: Preparation of (2R,3S,4R,5R)-2-(6-benzamido-9H-purin-9-yl)-4-fluoro-5-(hydroxymethyptetrahydrofuran-3-yl hydrogen phosphonate (5): To a solution of compound 4 (0.78 g, 1.1 mmol, 1 eq) in DCM (13 mL) was added water (190 µL, 11 mmol, 10 eq) and a solution of DCA (760 µL 9.2 mmol, 8.7 eq) in DCM (13 mL). The mixture was stirred for 10 min and quenched with pyridine (1.5 mL, 18 mmol, 17 eq). The mixture was concentrated in vacuo and co-evaporated with anhydrous MeCN (3×10 mL) to provide compound 5 in 4 mL of MeCN.

Step 4: Preparation of (2R,3S,4R,5R)-2-(6-benzamido-9H-purin-9-yl)-5-((((((2R,3S,4R,5R)-2-(6-benzamido-9H-purin-9-yl)- 5-((bis(4-methoxyphenyl)(phenyl)methoxy)methyl)-4-fluorotetrahydrofuran-3-yl)oxy)(2-cyanoethoxy) phosphorothioyl)oxy)methyl)-4-fluorotetrahydrofuran-3-yl hydrogen phosphonate (6): Compound 2 (1.1 g, 1.2 mmol, 1.1 eq) was dried via co-evaporation in vacuo with anhydrous MeCN (3×10 mL leaving 8 mL). This solution was added to the solution of compound 5 from Step 3 and stirred for 5 min. DDTT (240 mg, 1.2 mmol, 1.1 eq) was added and the mixture was stirred for 30 min then concentrated in vacuo to provide compound 6.

Step 5: Preparation of N,N'-(((1S,3R,6R,8R,9S,11R,14R,16R,17R,18R)-3-(2-cyanoethoxy)-17,18-difluoro-11-mercapto-11-oxido-3-sulfido-2,4,7,10,12,15-hexaoxa-3,11-diphosphatricyclo[12.2.1.1$^{6,9}$]octadecane-8,16-diyObis(9H-purine-9,6-diyl))dibenzamide (7A): To a solution of compound 6 in DCM (25 mL) was added water (190 µL, 11 mmol, 10 eq) and a solution of DCA (1.5 mL, 18 mmol, 17 eq) in DCM (25 mL). The mixture was stirred for 10 min, then quenched with pyridine (11 mL, 130 mmol, 120 eq), then concentrated in vacuo to approximately 13 mL. An additional 30 mL of anhydrous pyridine was added. The solution was treated with DMOCP (580 mg, 3.2 mmol, 3 eq) and stirred for 3 min, after which water (570 µL, 32 mmol, 30 eq) was added followed immediately by 3H-1,2-benzodithiol-3-one (260 mg, 1.6 mmol, 1.5 eq). After 5 min the solution was poured into saturated NaHCO$_3$ (100 mL) and extracted with EtOAc (2×100 mL). The organic layers were combined and concentrated to give ~2.5 g of crude mixture of isomers 7A/B. Chromatography (80 g SiO$_2$, MeOH:DCM 0-15% over 54 min) gave 128 mg of compound 7A.

Step 6: Preparation of (1S,3R,6R,8R,9S,11R,14R,16R,17R,18R)-8,16-bis(6-amino-9H-purin-9-yl)-17,18-difluoro-3,11-dimercapto-2,4,7,10,12,15-hexaoxa-3,11-diphosphatricyclo[12.2.1.1$^{6,9}$]octadecane 3,11-dioxide (8): To a solution of 7A (70 mg) in MeOH (1.5 mL) was added NH$_4$OH (1.5 mL). The reaction mixture was heated to 50° C. for 2.5 h then cooled, sparged with N$_2$ and concentrated in vacuo. Purification (RP MPLC—5.5 g C18—0-20% MeCN/TEAA (10 mM) over 90 column volumes) to give after lyophilization 10 mg of Compound 8. LCMS-ESI: 693.70 [M–H]$^-$ (calculated for C$_{20}$H$_{22}$F$_2$N$_{10}$O$_8$P$_2$S$_2$: 694.05); R$_t$: 8.174 min by LCMS conditions (20 mM NH$_4$OAc, 2% to 50%). $^1$H NMR. (400 MHz, 45° C., D$_2$O) δ 8.08 (s, 1H), 7.99 (s, 1H), 6.17 (d, J=8.4, 1H), 5.84 (dd, J=52.4, 3.6 1H), 5.19-5.11 (m, 1H), 4.77 (m, 1H), 4.46-4.2 (m, 1H), 4.10-4.09 (m, 1H), 3.09 (q, J=7.2, 6H), 1.17 (t, J=7.6 Hz, 9H).

Example 3

Synthesis of 2'2'-RR-(A)(A) (15)

(1R,3R,6R,8R,9R,11R,14R,16R,17R,18R)-8,16-bis(6-amino-9H-purin-9-yl)-17,18-dihydroxy-3,11-dimercapto-2,4,7,10,12,15-hexaoxa-3,11-diphosphatricyclo[12.2.1.1$^{6,9}$] octadecane 3,11-dioxide (15), also referred to as 2'2'-RR-(A)(A), bis 2'-5'-RR-(A)(A), or dithio-(Rp,Rp)-cyclic-[A(2',5')p-A(2',5')p] was prepared according to the following Scheme 3:

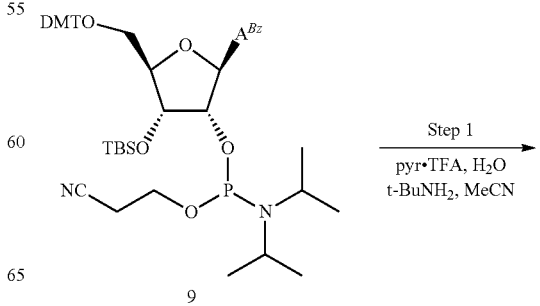

9

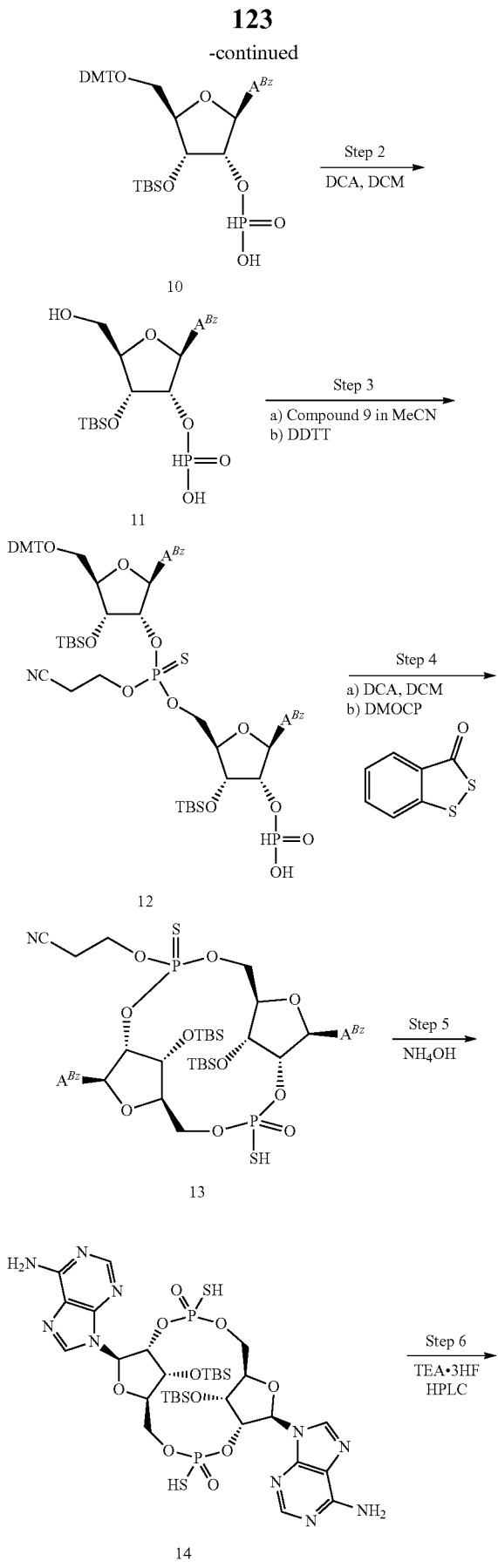

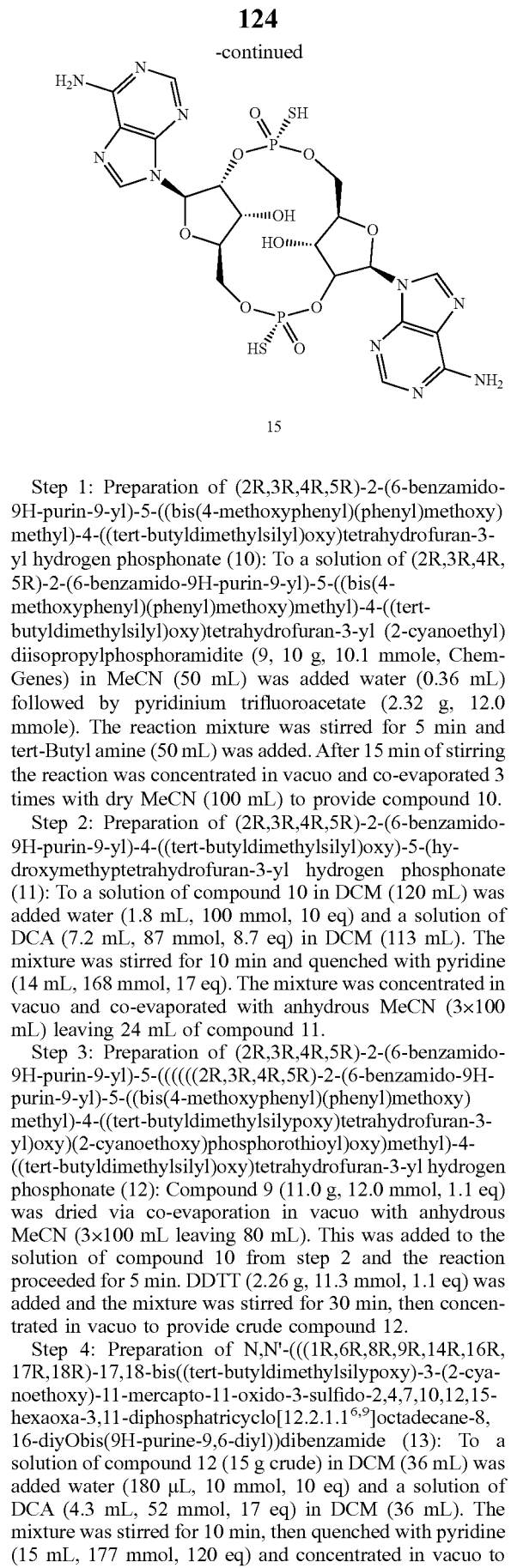

Step 1: Preparation of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl hydrogen phosphonate (10): To a solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (9, 10 g, 10.1 mmole, ChemGenes) in MeCN (50 mL) was added water (0.36 mL) followed by pyridinium trifluoroacetate (2.32 g, 12.0 mmole). The reaction mixture was stirred for 5 min and tert-Butyl amine (50 mL) was added. After 15 min of stirring the reaction was concentrated in vacuo and co-evaporated 3 times with dry MeCN (100 mL) to provide compound 10.

Step 2: Preparation of (2R,3R,4R,5R)-2-(6-benzamido-9H-purin-9-yl)-4-((tert-butyldimethylsilyl)oxy)-5-(hydroxymethyptetrahydrofuran-3-yl hydrogen phosphonate (11): To a solution of compound 10 in DCM (120 mL) was added water (1.8 mL, 100 mmol, 10 eq) and a solution of DCA (7.2 mL, 87 mmol, 8.7 eq) in DCM (113 mL). The mixture was stirred for 10 min and quenched with pyridine (14 mL, 168 mmol, 17 eq). The mixture was concentrated in vacuo and co-evaporated with anhydrous MeCN (3×100 mL) leaving 24 mL of compound 11.

Step 3: Preparation of (2R,3R,4R,5R)-2-(6-benzamido-9H-purin-9-yl)-5-((((((2R,3R,4R,5R)-2-(6-benzamido-9H-purin-9-yl)-5-((bis(4-methoxyphenyl)(phenyl)methoxy)methyl)-4-((tert-butyldimethylsilypoxy)tetrahydrofuran-3-yl)oxy)(2-cyanoethoxy)phosphorothioyl)oxy)methyl)-4-((tert-butyldimethylsilyl)oxy)tetrahydrofuran-3-yl hydrogen phosphonate (12): Compound 9 (11.0 g, 12.0 mmol, 1.1 eq) was dried via co-evaporation in vacuo with anhydrous MeCN (3×100 mL leaving 80 mL). This was added to the solution of compound 10 from step 2 and the reaction proceeded for 5 min. DDTT (2.26 g, 11.3 mmol, 1.1 eq) was added and the mixture was stirred for 30 min, then concentrated in vacuo to provide crude compound 12.

Step 4: Preparation of N,N'-(((1R,6R,8R,9R,14R,16R,17R,18R)-17,18-bis((tert-butyldimethylsilypoxy)-3-(2-cyanoethoxy)-11-mercapto-11-oxido-3-sulfido-2,4,7,10,12,15-hexaoxa-3,11-diphosphatricyclo[12.2.1.1$^{6,9}$]octadecane-8,16-diyObis(9H-purine-9,6-diyl))dibenzamide (13): To a solution of compound 12 (15 g crude) in DCM (36 mL) was added water (180 µL, 10 mmol, 10 eq) and a solution of DCA (4.3 mL, 52 mmol, 17 eq) in DCM (36 mL). The mixture was stirred for 10 min, then quenched with pyridine (15 mL, 177 mmol, 120 eq) and concentrated in vacuo to approximately 30 mL. The solution was treated with DMOCP (1.75 g, 9.6 mmol, 3 eq) and stirred for 3 min, after which water (1.6 mL, 90 mmol, 30 eq) was added followed immediately by 3H-1,2-benzodithiol-3-one (390 mg, 2.4 mmol, 1.5 eq). After 5 min the solution was poured into saturated NaHCO$_3$ (150 mL) and extracted with EtOAc (2×150 mL). The organic layers were combined and concentrated to give 8 g of crude material. Chromatography (220 g SiO$_2$, MeOH:DCM) provided 260 mg of compound 13 as a mixture of diastereomers.

Step 5: Preparation of (1R,6R,8R,9R,14R,16R,17R,18R)-8,16-bis(6-amino-9H-purin-9-yl)-17,18-bis((tert-butyldimethylsilypoxy)-3,11-dimercapto-2,4,7,10,12,15-hexaoxa-3,11-diphosphatricyclo[12.2.1.1$^{6,9}$]octadecane 3,11-dioxide (14): To a solution of compound 13 (260 mg) in MeOH (4.3 mL) was added concentrated NH$_4$OH (4.3 mL). The reaction mixture was heated to 50° C. for 2.5 h then cooled, sparged with N$_2$ and concentrated in vacuo to give compound 14 as a mixture of diastereomers.

Step 6: Preparation of (1R,3R,6R,8R,9R,11R,14R,16R,17R,18R)-8,16-bis(6-amino-9H-purin-9-yl)-17,18-dihydroxy-3,11-dimercapto-2,4,7,10,12,15-hexaoxa-3,11-diphosphatricyclo[12.2.1.1$^{6,9}$]octadecane 3,11-dioxide (15): To the mixture of compound 14 (113 mg) was added TEA.3HF (1.2 mL). The reaction was heated to 50° C. for 2.5 h. The mixture was poured into a solution of TEA (2.2 mL) and TEAB (6.4 mL) while stirring. The solution was desalted and purified using a prep-MPLC-C18 (100% 20 mM NH$_4$OAc to 0% MeCN/20 mM NH$_4$OAc). Additional purification using prep HPLC (6-24% acetonitrile/TEAA (10 mM)) gave 11 mg of Compound 15. LCMS-ESI: 689.20 [M−H]$^-$ (calculated for C$_{20}$H$_{24}$N$_{10}$O$_{10}$P$_2$S$_2$: 690.06); R$_t$: 8.8 min by LCMS conditions (20 mM NH$_4$OAc, 2% to 50% over 20 min). $^1$H NMR. (400 MHz, 45° C., D$_2$O) δ 8.98 (s, 1H), 8.37 (s, 1H), 6.46 (d, J=8.0, 1H), 5.4-5.3 (m, 1H), 4.78 (s, 1H), 4.66 (s, 1H), 4.63 (s, 2H), 3.33 (q, J=7.2, 6H), 1.42 (t, J=7.2 Hz, 9H).

Example 4

In Vitro Binding Analysis of CDN Compounds with Purified STING Protein

DNA encoding amino acids 140-379 (amino acid numbering corresponding to Swiss Prot Q86WV6) was amplified from plasmids containing the full length sequence of human STING alleles via polymerase chain reaction with the following primers: forward TACTTCCAATCCAATGCAGCCCCAGCTGAGATCTCTG (SEQ ID NO: 7) and reverse TTATCCACTTCCAATGTTATTATTATCAAGAGAAATCCGTGCGGAG (SEQ ID NO: 8). STING variant alleles were assigned according to Yi, et al, (2013), PLoS One, 8(10), e77846 (DOI: 10.1371/journal.pone.0077846. PCR products were cloned into bacterial expression vector encoding a N-terminal hexa-histidine affinity tag (6×HIS) (SEQ ID NO: 22) followed by a small ubiquitin-like modifier (SUMO) solubility sequence (Butt, et al, (2005) Protein expression and purification 43.1, 1-9) and tobacco etch virus protease cleavage site (TEV) using ligation independent cloning (Aslanidis, et al, (1990) Nucleic acids research, 18.20, 6069-6074).

Plasmids encoding 6×HIS-SUMO-TEV-STING amino acids 140-379 were transformed into Rosetta2 (DE3) E. coli cells (EMD Millipore) for protein expression. Cells were grown in lysogeny broth at 37° C. until a 600 nM absorbance of 0.6 was reached. Cells were then transferred to 18° C. and protein expression was induced overnight by the addition of isopropyl β-D-1-thiogalactopyranoside to the media at a concentration of 0.25 mM. Cells were harvested by centrifugation at 6,000 times gravity for 10 minutes. Cell pellets were resuspended on ice in a buffer containing 50 mM Tris hydrochloride (Tris-HCl) pH 7.5, 500 mM sodium chloride (NaCl), 20 mM imidazole, 10% glycerol, 1 mM tris(2-carboxyethyl)phosphine hydrochloride (TCEP) and protease inhibitor tablet (Pierce) (Buffer A). Cells were lysed using an S-450D sonifier (Emmerson industrial) on ice. Cell lysate was centrifuged at 15,000 times gravity for 30 minutes at 4° C. Soluble material was applied to nickel-nitrilotriacetic acid (Ni-NTA) coupled Sepharose CL-6B (Qiagen) for 1 hour with gentle rocking at 4° C. After transfer to a gravity flow poly-prep column (Bio-Rad), resin was washed extensively in buffer A. Protein was eluted from the column in a buffer containing 20 mM Tris-HCl pH 7.5, 150 mM NaCl, 300 mM imidazole, 10% glycerol and 0.5 mM TCEP. To remove the 6×HIS-SUMO tag eluted protein was mixed with TEV protease (Sigma) at a ratio of 1:250 (w:w) and dialyzed overnight against a buffer containing 20 mM Tris-HCl pH 7.5, 150 mM NaCl, 5 mM imidazole, 10% glycerol and 0.5 mM TCEP. TEV protease and 6×HIS-SUMO tags were depleted by the addition of Ni-NTA resin (Qiagen) to the sample, purified STING amino acids 140-379 was collected by removal of the resin using a poly-prep column. STING AA140-379 was concentrated with a 10,000 Dalton molecular weight cutoff centrifuge concentrator (EMD Millipore) to a final concentration of approximately 10 mg/ml. Protein was aliquoted, flash frozen in liquid nitrogen and stored at −80° C. until use.

The resulting amino acid sequence for the STING WT allele is as follows:

Allele Name: WT

Amino Acid Sequence:

(SEQ ID NO: 9)
APAEISAVCEKGNFNVAHGLAWSYYIGYLRLILPELQARIRTYNQHYNNLL

RGAVSQRLYILLPLDCGVPDNLSMADPNIRFLDKLPQQTGDRAGIKDRVYS

NSIYELLENGQRAGTCVLEYATPLQTLFAMSQYSQAGFSREDRLEQAKLFC

RTLEDILADAPESQNNCRLIAYQEPADDSSFSLSQEVLRHLRQEEKEEVTV

GSLKTSAVPSTSTMSQEPELLISGMEKPLPLRTDFS.

The resulting amino acid sequences for the STING REF allele is as follows:

Allele Name: REF

Amino Acid Sequence:

(SEQ ID NO: 10)
APAEISAVCEKGNFNVAHGLAWSYYIGYLRLILPELQARIRTYNQHYNNLL

RGAVSQRLYILLPLDCGVPDNLSMADPNIRFLDKLPQQTGDHAGIKDRVYS

NSIYELLENGQRAGTCVLEYATPLQTLFAMSQYSQAGFSREDRLEQAKLFC

RTLEDILADAPESQNNCRLIAYQEPADDSSFSLSQEVLRHLRQEEKEEVTV

GSLKTSAVPSTSTMSQEPELLISGMEKPLPLRTDFS.

The resulting amino acid sequences for the STING HAQ allele is as follows: Allele Name: HAQ Amino Acid Sequence:

(SEQ ID NO: 11)
APAEISAVCEKGNFNVAHGLAWSYYIGYLRLILPELQARIRTYNQHYNNLL

RGAVSQRLYILLPLDCGVPDNLSMADPNIRFLDKLPQQTADRAGIKDRVYS

NSIYELLENGQRAGTCVLEYATPLQTLFAMSQYSQAGFSREDRLEQAKLFC

QTLEDILADAPESQNNCRLIAYQEPADDSSFSLSQEVLRHLRQEEKEEVTV

GSLKTSAVPSTSTMSQEPELLISGMEKPLPLRTDFS.

Differential scanning fluorometry (DSF) is a technique that measures the ability of ligands to bind to and stabilize purified proteins (Niesen, et al, (2007) Nature protocols 2.9, 2212-2221). The protein is heated in the presence of a dye that binds to and fluoresces in hydrophobic environments. The protein is thermally denatured by heating resulting in increased dye binding to the unfolded protein and fluorescence. The temperature midpoint ($T_m$) of a proteins denaturation is established by calculating the half maximal value of the denaturation curve. The temperature midpoint of the protein in the presence of a ligand is directly related to the affinity of the ligand for the protein and therefore its ability to stabilize the protein at higher temperatures.

DSF was performed in a 20 µl reaction comprising 20 mM Tris-HCl pH 7.5, 150 mM NaCl, 1:500 dilution of SYPRO Orange (Life Technologies), 1 mg/ml purified STING AA140-379 protein and ligand at a concentration of 1 mM. Each of wild type hSTING, HAQ allele hSTING and REF allele hSTING were used with each of the invention compound 2'2'-RR-(3'F-A)(3'F-A) and comparison STING agonists 3'3'-RR-(2'F-A)(2'F-A); 2'3'-RR-(3'F-A)(2'F-A); and 2'2'-RR-(A)(A), as well as the natural ligand 2'3'-(G)(A). Samples were placed in hard shell PCR plate (Bio-Rad). The fluorescence as a function of temperature was recorded in a CFX 96 real time PCR machine (Bio-Rad) reading on the HEX channel, excitation 450-490, emission 560-580 nm. The temperature gradient was from 15-80° C. ramping 0.5° C. per 15 seconds and recording every 0.5° C. After subtraction of the background signal from a sample lacking protein and ligand. The midpoint temperature ($T_m$) was calculated by fitting the curves of the fluorescence as a function of temperature to a Boltzmann sigmoidal function (Graph Pad Prism). The change in thermal stability of STING AA140-379 in the presence of ligand ($T_m$ Shift) was calculated by subtracting the $T_m$ (Protein and Ligand) from $T_m$ (Protein alone). The results are shown in the following Table 4.

TABLE 4

$T_m$ shifts in hSTING WT, HAQ allele and REF allele

| Compound | hSTING $T_m$ Shift (° C.) | | |
|---|---|---|---|
| | WT | HAQ | REF |
| 2'2'-RR-(3'F-A)(3'F-A) | 13.9 | 19.7 | 12.5 |
| 3'3'-RR-(2'F-A)(2'F-A) | 19.3 | 32.4 | 9.1 |
| 2'3'-RR-(3'F-A)(2'F-A) | 14.5 | 26 | 10.5 |
| 2'3'-(G)(A) | 16.1 | 27.8 | 7.2 |
| 2'2'-RR-(A)(A) | 3.4 | 5.1 | 3.6 |

The invention compound 2'2'-RR-(3'F-A)(3'F-A) binds strongly to all three hSTING proteins, as shown in significantly improved binding as compared to the di-OH compound 2'2'-RR-(A)(A). Also, quite surprisingly 2'2'-RR-(3'F-A)(3'F-A) shows less variability in binding to the various alleles as compared to the 3'3'-RR-(2'F-A)(2'F-A) and 2'3'-RR-(3'F-A)(2'F-A), and the natural ligand 2'3'-(G)(A). This could provide advantages to dosing a varied patient population without having to assay hSTING variations.

The WT and REF proteins were similarly prepared for use in an ITC binding assay. Expression plasmids were transformed into BL21 Rosetta 2 (DE3) (EMD Millipore) *E. coli* cells for protein expression. 50 ml starter cultures were grown overnight in 2×YT supplemented with 50 µg/ml kanamycin and 30 µg/ml chloramphenicol. Multi-liter large scale cultures of the same growth media as the starter were inoculated at a ratio of 1:1,000 (V/V) and allowed to grow at 37° C. to an optical density of 0.6, cultures were then shifted to 18° C. Protein expression was induced by the addition of isopropyl β-D-1-thiogalactopyranoside to a final concentration of 0.3 mM. Protein expression was allowed to proceed for 18-24 hrs. Pelleted cells were resuspended in 50 mM Tris pH 7.5, 500 mM NaCl, 10% glycerol, 20 mM imidazole, 1 mM TCEP and complete protease inhibitor cocktail (Sigma). Cells were lysed by sonication (Branson) and insoluble material was removed by centrifugation. Proteins were purified on Ni-NTA resin and concentrated to >10 mg/ml. 6×H-SUMO-STING LBD was further purified by gel filtration chromatography using a High Load 26/600 Superdex 75 column (GE Healthcare) in a buffer of 20 mM Tris pH 7.5, 150 mM NaCl, 5% glycerol and 1 mM TCEP. Peak fractions were concentrated to between 10-15 mg/ml via ultrafiltration aliquoted and flash frozen in liquid nitrogen and stored at ~80° C.

The resulting amino acid sequence for the STING WT allele is as follows:
Allele Name: WT
Amino Acid Sequence:

(SEQ ID NO: 12)
MGSSHHHHHHGSSMASMSDSEVNQEAKPEVKPEVKPETHINLKVSDGSSEI

FFKIKKTTPLRRLMEAFAKRQGKEMDSLRFLYDGIRIQADQTPEDLDMEDN

DIIEAHREQIGGIEENLYFQSNAAPAEISAVCEKGNFNVAHGLAWSYYIGY

LRLILPELQARIRTYNQHYNNLLRGAVSQRLYILLPLDCGVPDNLSMADPN

IRFLDKLPQQTGDRAGIKDRVYSNSIYELLENGQRAGTCVLEYATPLQTLF

AMSQYSQAGFSREDRLEQAKLFCRTLEDILADAPESQNNCRLIAYQEPADD

SSFSLSQEVLRHLRQEEKEEVTVGSLKTSAVPSTSTMSQEPELLISGMEKP

LPLRTDFS.

The resulting amino acid sequences for the STING REF allele is as follows:
Allele Name: REF
Amino Acid Sequence:

(SEQ ID NO: 13)
MGSSHHHHHHGSSMASMSDSEVNQEAKPEVKPEVKPETHINLKVSDGSSEI

FFKIKKTTPLRRLMEAFAKRQGKEMDSLRFLYDGIRIQADQTPEDLDMEDN

DIIEAHREQIGGIEENLYFQSNAAPAEISAVCEKGNFNVAHGLAWSYYIGY

LRLILPELQARIRTYNQHYNNLLRGAVSQRLYILLPLDCGVPDNLSMADPN

IRFLDKLPQQTGDHAGIKDRVYSNSIYELLENGQRAGTCVLEYATPLQTLF

-continued

AMSQYSQAGFSREDRLEQAKLFCRTLEDILADAPESQNNCRLIAYQEPADD

SSFSLSQEVLRHLRQEEKEEVTVGSLKTSAVPSTSTMSQEPELLISGMEKP

LPLRTDFS.

Proteins were dialyzed overnight in 20 mM HEPES pH 7.5, 150 mM NaCl. Insoluble material was removed by centrifugation at 31,000×g. The invention compound 2'2'-RR-(3'F-A)(3'F-A) and comparison STING agonists 3'3'-RR-(2'F-A)(2'F-A); 2'3'-RR-(3'F-A)(2'F-A) were resuspended in dialysis buffer. The concentration of both the protein and ligands were checked by spectroscopy and adjusted if necessary.

STING protein was added to the ITC sample cell at a final concentration of 0.1 mM. The CDN ligand was at a final concentration of 0.35 mM in the syringe. An injection cycle of 19 injections of 2.39 µl spaced 200 seconds apart with stir speed of 350 rpm was used. Data was collected at 25° C. on a TA Instruments Nano ITC device.

Data was processed and fit with NanoAnalyze (TA Instruments). The background heat from the dilution of the ligand into buffer was subtracted from a duplicate run with no protein. Peaks representing the reaction heat were integrated and the area (kcal/mol) of ligand injected was plotted against the molar ratio of protein to ligand (binding isotherm). The data was curve fit in NanoAnalyze using the least squares method and binding parameters derived. The results are shown in the following Table 5.

TABLE 5

$K_D$ (nM) from ITC assay for hSTING WT and REF allele.

| Compound | hSTING $K_D$ nM | |
|---|---|---|
| | WT | REF |
| 2'2'-RR-(3'F-A)(3'F-A) | 98 | 170 |
| 3'3'-RR-(2'F-A)(2'F-A) | 74 | 591 |
| 2'3'-RR-(3'F-A)(2'F-A) | 109 | 333 |

Similarly to the DSF assay, the invention compound 2'2'-RR-(3'F-A)(3'F-A) shows less variation in binding between the WT and REF alleles.

Example 5

CDN Compounds Potently Activate Human STING Signaling in THP1 Cells

To determine the relative level of type I interferon induced in human cells by 2'2'-RR-(3'F-A)(3'F-A) as a signature of adjuvant potency, 100,000 THP1-Dual cells (a human monocyte cell line containing the hSTING HAQ allele transfected with an IRF-3 inducible secreted luciferase reporter gene (Invivogen) which express secreted luciferase under the control of a promoter comprised of five IFN-stimulated response elements) were activated with 30 ng/ml phorbol 12-myristate 13-acetate overnight in a 96-well dish. Cells were washed with fresh media and incubated for 30 min at 37° C. with 5% $CO_2$ with compounds in 3-fold titration steps from 2,000 to 0.0338 µM in PB buffer (50 mM 4-(2-hydroxyethyl)-1-piperazineethanesulfonic acid, 100 mM KCl, 3 mM $MgCl_2$, 0.1 mM dithiothreitol, 85 mM sucrose, 1 mM ATP, 0.1 mM GTP and 0.2% bovine serum albumin). After 30 minutes, cells were washed and fresh RPMI media containing 10% FBS was added, and cells were incubated at 37° C. with 5% $CO_2$. Cell culture supernatants from each sample were collected after overnight incubation, and 10 µl of the cell culture supernatants was added to 50 µl QUANTI-Luc reagent (Invivogen). Type I interferon activation was determined by measuring secreted luciferase levels on a SpectraMax M3 spectrophotometer (Molecular Devices). The EC50 value for the same compounds as tested in Example 4 was determined from the dose-response curve for the 10 concentrations from the serial dilution of the compounds in this assay. Table 6 shows the results for the assay without digitonin.

TABLE 6

EC50 without digitonin in THP1 cells (HAQ allele).

| Compound | EC50 (µM) |
|---|---|
| 2'2'-RR-(3'F-A)(3'F-A) | 16.6 |
| 3'3'-RR-(2'F-A)(2'F-A) | 15.6 |
| 2'3'-RR-(3'F-A)(2'F-A) | 4.5 |
| 2'2'-RR-(A)(A) | >150 |
| 2'3'-(G)(A) | >150 |

The 2'2'-RR-(3'F-A)(3'F-A) is a very active STING agonists as shown in the THP-1 assay, having an EC50 of less than 20 µM.

Example 6

Induction of Type I Interferon by 2'2'-RR-(3'F-A)(3'F-A) in hPBMCs

The induction of type I interferon was measured in human primary blood mononuclear cells (hPBMCs) to evaluate the potency of 2'2'-RR-(3'F-A)(3'F-A) as described herein. hPBMCs from six donors were used: three donors homozygous for the wild type (WT) STING allele ($STING^{WT/WT}$), two donors homozygous for the reference (REF) (R232H) STING allele ($STING^{REF/REF}$), and a donor homozygous for the HAQ (R71H, G230A, R293Q) STING allele ($STING^{HAQ/HAQ}$). The STING genotype of these donors was determined by PCR amplification and sequencing: genomic DNA was isolated from hPBMCs using Quick Extract DNA Extraction Solution (Epicentre) and was used to amplify regions of exon 3, 6, and 7 of the human STING gene. Primers for amplification and sequencing were:

```
hSTING exon3F
                                        (SEQ ID NO: 14)
GCTGAGACAGGAGCTTTGG, hSTING exon3R
                                        (SEQ ID NO: 15)
AGCCAGAGAGGTTCAAGGA, hSTING exon6F
                                        (SEQ ID NO: 16)
GGCCAATGACCTGGGTCTCA, hSTING exon6R
                                        (SEQ ID NO: 17)
CACCCAGAATAGCATCCAGC, hSTING exon7F
                                        (SEQ ID NO: 18)
TCAGAGTTGGGTATCAGAGGC, hSTING exon7R
                                        (SEQ ID NO: 19)
ATCTGGTGTGCTGGGAAGAGG.
```

STING variant alleles were assigned according to Yi, et al., 2013, PLoS One, 8(10), e77846 (DOI: 10.1371/journal.pone.0077846).

Cryopreserved hPBMCs were thawed and $10^6$ cells were either left untreated or treated with 10 μM or 100 μM of reference compound 2'3'-(G)(A) (natural activator of hSTING) or 2'2'-RR-(3'F-A)(3'F-A) in RMPI media supplemented with 10% fetal bovine serum, 1% HEPES, and 1% Penicillin/Streptomycin. After 2 hours stimulation, cells were harvested by centrifugation and washed once in phosphate-buffered saline. Cellular RNA was isolated using the Aurum Total RNA 96 Kit, normalized by concentration across samples, and cDNA was synthesized using the iScript cDNA Synthesis Kit. Gene expression was assessed by qRT-PCR using PrimePCR probe assays and the CFX96 gene cycler (all reagents and equipment from Bio-Rad Laboratories). IFNβ expression was expressed relative to untreated cells. Results for these samples are shown in FIG. 1. The relative IFNβ expression for 2'2'-RR-(3'F-A)(3'F-A) is similar to or exceeding that of reference compound 2'3'-(G)(A). These results demonstrate that 2'2'-RR-(3'F-A)(3'F-A) compound is a potent STING activator in human cells homozygous for each of three of the prevalent STING alleles present in the human population.

Example 7

Anti-tumor Efficacy of 2'2'-RR-(3'F-A)(3'F-A)

To assess the ability of 2'2'-RR-(3'F-A)(3'F-A) to promote anti-tumor immunity in a murine tumor model, 6-8 week old female BALB/c mice (n=8/group) were implanted in both the left and the right flanks with 4T1 mammary carcinoma cells ($2\times10^5$ cells in 100 μL PBS). Mice were treated with 2'2'-RR-(3'F-A)(3'F-A) at 0.1, 1, 10 and 100 μg in a total volume of 40 μL HBSS and compared to Hank's Balanced Salt Solution (HBSS) vehicle control. Compound was administered when tumors reached a volume of approximately 40-50 mm$^3$ on day 8 post tumor implantation (indicated by dotted line on the x-axis in tumor growth graphs). The compound was administered by a single subcutaneous injection into the center of the tumor (intratumoral, IT) using a 27 gauge needle. Tumors were measured twice weekly.

As shown in FIGS. 2A-2E, in the 4T1 mammary carcinoma flank model, 2'2'-RR-(3'F-A)(3'F-A) induced potent dose-dependent tumor inhibition in both the primary (injected or "R") and distal (non-injected or "L") flank tumor as compared to HBSS. 2'2'-RR-(3'F-A)(3'F-A) demonstrated potent tumor regression efficacy, showing 100% (i.e., 8 out of 8 or N=8) cures of the primary tumor and 37.5% (i.e., 3 out of 8 or N=3) cures and delayed growth of the distal tumor at the 10 μg dose. These data demonstrate the potent anti-tumor effects of 2'2'-RR-(3'F-A)(3'F-A) in an aggressive syngeneic murine tumor model.

Example 8

T Cell Mediated Anti-Tumor Immunity Induced by 2'2'-RR-(3'F-A)(3'F-A)

To demonstrate that the anti-tumor effect of 2'2'-RR-(3'F-A)(3'F-A) is mediated by T cell (adaptive) immune responses, blood was collected from mice from Example 7 on day 7 post IT injection. Lympholyte (Cedarlane) gradient-purified PBMCs (~$1\times10^6$) were pre-incubated with anti-CD16/32 monoclonal antibody to block potential non-specific binding and labeled with murine T-Select H-2L$^d$ MuLV gp70 Tetramer-SPSYVYHQF-PE (SEQ ID NO: 20, AH1 peptide with PE fluorescent label, MBL), anti-CD4-BUV737 (RMA4-5), anti-CD8α-BUV395 (53-6.7) (BD Biosciences); anti-CD90.2 BV510 (30-H12) (BioLegend) and the Fixable LIVE/DEAD Near-IR viability dye (ThermoFisher). Data were acquired using a LSRFortessa X-20 cytometer with FACSDiva software (BD) and analyzed with FlowJo software (Tree Star).

Figure 3:
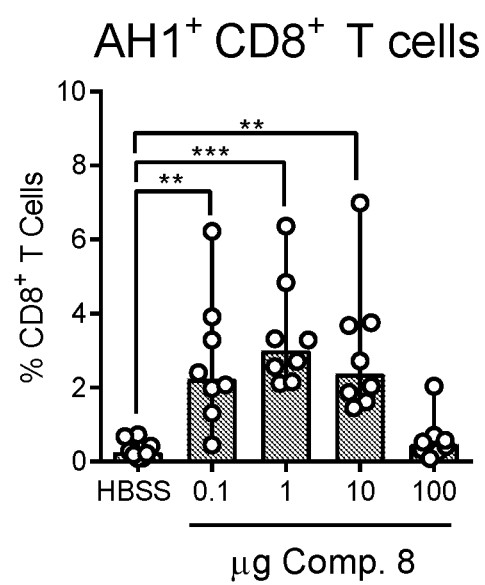
FIG. 3 depicts the percentage of tumor specific T cells in blood from a 4T1 mammary carcinoma mouse model, seven days post intratumoral injection of HBSS vehicle or Compound 8 at 0.1, 1, 10 or 100 μg.
Figure 4A:
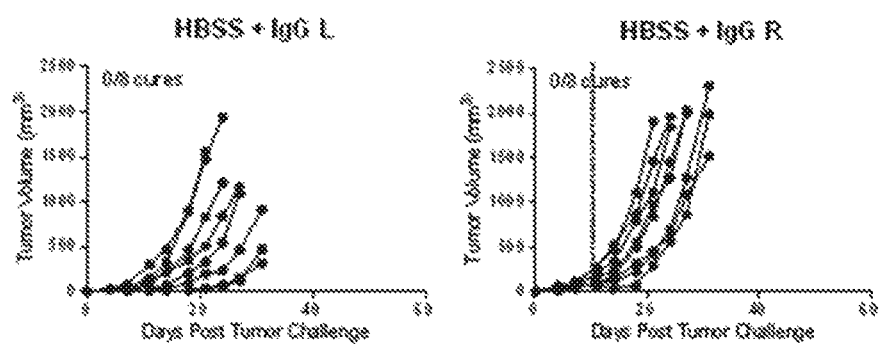
FIGS. 4A-4E depict the tumor volume in injected and distal tumors in a 4T1 mammary carcinoma mouse model, following a single intratumoral injection of Compound 8 at 1 μg with intraperitoneal injection of IgG (4C) or anti-PD-1 antibody (4D) or with anti-PD-1 antibody and anti-CD8α antibody (4E), compared to IgG alone (4A) or anti-PD-1 antibody alone (4B).
Figure 4B:
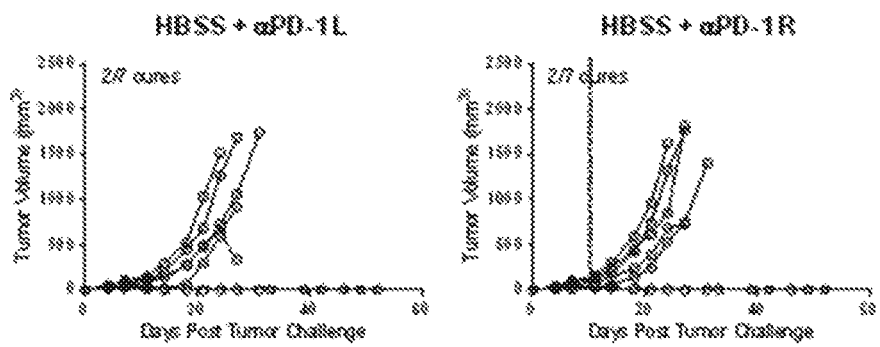
Figure 4C:
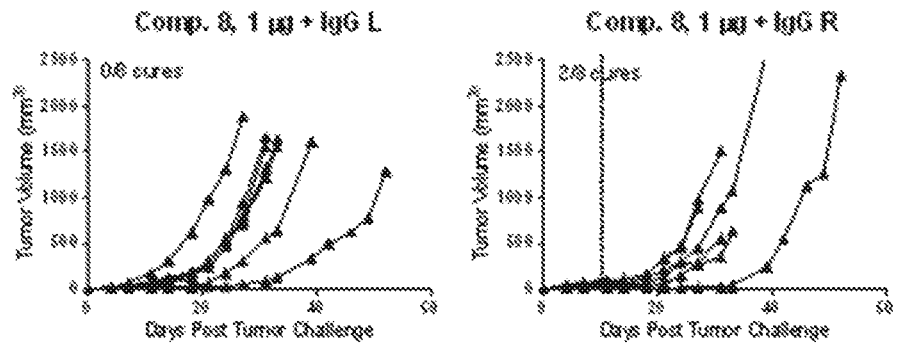
Figure 4D:
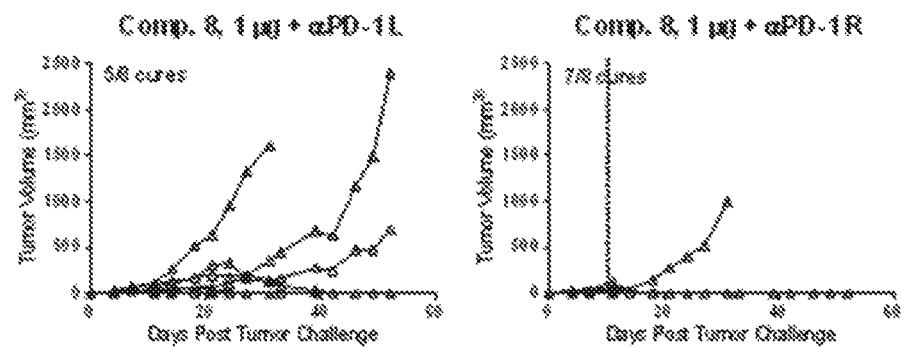
Figure 4E:
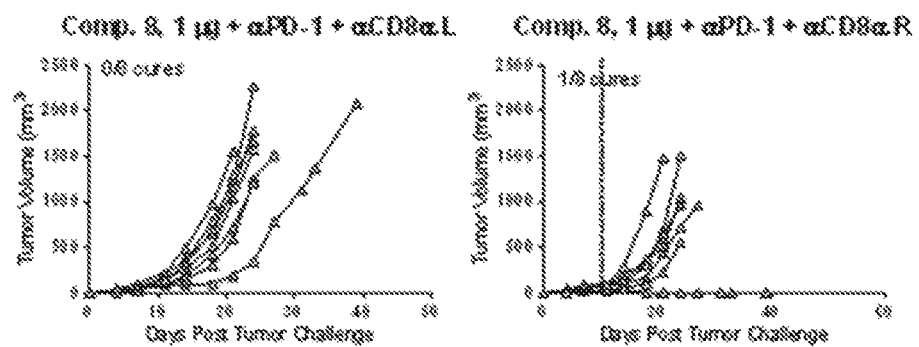

As shown in FIG. 3, 2'2'-RR-(3'F-A)(3'F-A) elicits a significantly higher frequency of tumor-specific systemic T cells at 0.1, 1 and 10 μg IT doses as compared to HBSS (P<0.01, *P<0.001, one-way ANOVA). By eliciting significant tumor-specific T cell responses at the 0.1 μg dose, 2'2'-RR-(3'F-A)(3'F-A) exhibits desirable dose-sparing properties.

Example 9

Enhancement of Anti-Tumor Efficacy by Combining 2'2'-RR-(3'F-A)(3'F-A) with Anti-PD-1 Antibody To assess the ability of 2'2'-RR-(3'F-A)(3'F-A) to promote anti-tumor immunity in murine tumor models in combination with an antagonistic anti-PD-1 antibody, 6-8 week old female BALB/c mice (n=8/group) were implanted in both the left and the right flanks with 4T1 mammary carcinoma cells ($2\times10^5$ cells in 100 aL PBS, day 0). Mice were treated with vehicle alone or 1 μg 2'2'-RR-(3'F-A)(3'F-A) in a total volume of 40 aL HBSS by IT injection using a 27 gauge needle when tumors reached a volume of approximately 40-50 mm$^3$ on day 8 post tumor implantation (indicated by dotted line on the x-axis in tumor growth graphs). Mice were given intraperitoneal (IP) injections of 200 μg control IgG or anti-PD-1 (clone RMP1-14, BioXCell) beginning on the day of 2'2'-RR-(3'F-A)(3'F-A) treatment and then continuing twice per week throughout the duration of the experiment. Some mice were given IP injection of 100 μg anti-CD8 (clone 2.43, BioXCell) on study days 6, 8, 10, 14, and 17 to deplete CD8$^+$ T cells. Tumors were measured twice weekly.

As shown in FIGS. 4A-4E, when combined with anti-PD-1 antibody therapy in the 4T1 mammary carcinoma flank model, 1 μg 2'2'-RR-(3'F-A)(3'F-A) induced potent tumor inhibition in both the primary (injected or "R", 87.5% cures) and distal (non-injected or "L", 62.5% cures) flank tumor as compared to mice receiving either HBSS+control IgG (0% cures in injected/non-injected) or 1 μg 2'2'-RR-(3'F-A)(3'F-A)+IgG (25% cures in injected/0% cures in non-injected). When mice were treated with anti-CD8 antibody (effectively depleting CD8$^+$ T cells), the therapeutic effect garnered by the combination of 2'2'-RR-(3'F-A)(3'F-A) and anti-PD-1 was lost, as tumors in CD8 depleted animals grow similar to that of treatment control animals. These data demonstrate that the potent anti-tumor effects of 2'2'-RR-(3'F-A)(3'F-A) combined with anti-PD-1 are dependent on cytotoxic T cells and therefore a result of adaptive immune-mediated anti-tumor responses capable of eradicating distal, non-injected tumors.

Example 10

Enhancement of Anti-Tumor T Cell Responses by Combining 2'2'-RR-(3'F-A)(3'F-A) with Anti-PD-1

To directly quantify the effect of combining 2'2'-RR-(3'F-A)(3'F-A) with anti-PD-1 on tumor-specific T cells, a cohort of mice from Example 9 were euthanized on day 7 post IT injection and non-injected tumors dissociated into a single cell suspension. Tumor-infiltrating lymphocytes (TILs) were incubated for 6 hours with or without 1 μM AH1 peptide (SPSYVYHQF, SEQ ID NO: 20) in the presence of brefeldin A and monensin to block cytokine secretion. After peptide stimulation, TILs were pre-incubated with anti-CD16/32 monoclonal antibody to block potential nonspecific binding and labeled with murine T-Select H-2L$^d$ MuLV gp70 Tetramer-SPSYVYHQF-PE (SEQ ID NO: 20, AH1 peptide, MBL), anti-CD4-BUV737 (RMA4-5), anti-CD8α-BUV395 (53-6.7) (BD Biosciences); anti-CD90.2 BV510 (30-H12) (BioLegend) and the Fixable LIVE/DEAD Near-IR viability dye (ThermoFisher). Data were acquired using a LSRFortessa X-20 cytometer with FACSDiva software (BD) and analyzed with FlowJo software (Tree Star).

Figure 5:
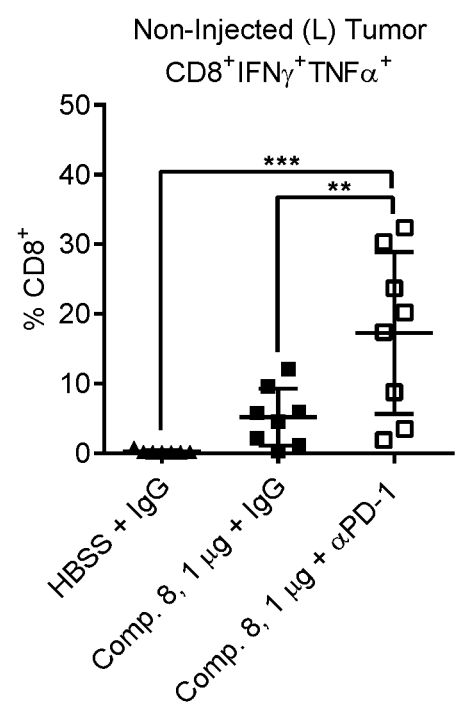
FIG. 5 depicts the percentage of tumor specific T cells in the distal tumor of a 4T1 mammary carcinoma mouse model, seven days post intratumoral injection of HBSS vehicle, or Compound 8 at 1 μg with or without intraperitoneal injection of anti-PD-1 antibody.

As shown in FIG. 5, while 2'2'-RR-(3'F-A)(3'F-A) elicits a tumor-specific T cell response measurable above background, the combination of 2'2'-RR-(3'F-A)(3'F-A) with anti-PD-1 elicits a statistically significant increase in polyfunctional IFNγ$^+$TNFα$^+$ CD8 T cells specific for the AH1 peptide in the tumor microenvironment (P<0.01, *P<0.001, one-way ANOVA). The presence of this enhanced T cell response in the distal tumor correlates with increased CD8$^+$ T cell-dependent tumor burden control demonstrated in Example 9. The ability to effectively synergize with anti-PD-1 checkpoint therapy to bring about substantial tumor clearance through a CD8$^+$ T cell dependent mechanism is a significant characteristic of 2'2'-RR-(3'F-A)(3'F-A).

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patent applications, patents, publications and other references mentioned in the specification are indicative of the levels of those of ordinary skill in the art to which the invention pertains and are each incorporated herein by reference. The references cited herein are not admitted to be prior art to the claimed invention.

Unless otherwise defined, all technical and scientific terms used herein have the same meaning as commonly understood by one of ordinary skill in the art to which this invention belongs. In the case of conflict, the present specification, including definitions, will control.

The use of the articles "a", "an", and "the" in both the description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of".

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 10% more or less than the specified value. In another embodiment, the term "about" refers to a range of values which are 5% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the terms "between X and Y" and "range from X to Y, are inclusive of X and Y and the integers there between. On the other hand, when a series of individual values are referred to in the disclosure, any range including any of the two individual values as the two end points is also conceived in this disclosure. For example, the expression "a dose of about 100 mg, 200 mg, or 400 mg" can also mean "a dose ranging from 100 to 200 mg", "a dose ranging from 200 to 400 mg", or "a dose ranging from 100 to 400 mg".

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound having the structure:

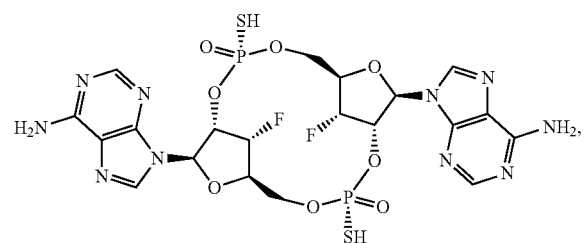 [SMILES: Nc1ncnc2c1ncn2[C@@H]1O[C@@H]2CO[P@@](=O)(S)O[C@@H]3[C@H](F)[C@@H](CO[P@@](=O)(S)O[C@@H]1[C@@H]2F)O[C@H]3n1cnc2c(N)ncnc21]

or a tautomer, pharmaceutically acceptable salt, pharmaceutically acceptable solvate or pharmaceutically acceptable hydrate thereof.

2. A composition comprising the compound according to claim (i) a pharmaceutically acceptable excipient; or (ii) a delivery vehicle which enhances cellular uptake and/or stability of the compound; or (iii) one or more agents selected from the group consisting of an immune checkpoint inhibitor; a Toll-like Receptor (TLR) agonist; a composition that mediates innate immune activation via TLRs, via (NOD)-like receptors (NLRs), via Retinoic acid inducible gene-based (RIG)-1-like receptors (RLRs), via C-type lectin receptors (CLRs), or via pathogen-associated molecular patterns ("P AMPs"); and a chemotherapeutic agent; or (iv) an inactivated tumor cell which expresses and secretes one or more cytokines which stimulate dendritic cell induction, recruitment and/or maturation, or one or more heat shock proteins.

3. The composition according to claim 2, wherein the composition does not include an agent that enhances cellular permeability of the compound or an agent that enhances uptake of the compound into a cell.

4. The composition according to claim 2, wherein the delivery vehicle comprises one or more agents selected from the group consisting of lipids, liposomes, hydrogels, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

5. The composition according to claim 2, wherein the one or more agents is an immune checkpoint inhibitor, which is optionally selected from the group consisting of a CTLA-4 pathway antagonist, a PD-I pathway antagonist, a Tim-3 pathway antagonist, a Vista pathway antagonist, a BTLA pathway antagonist, a LAG-3 pathway antagonist, and a TIGIT pathway antagonist.

6. The composition according to claim 2, wherein the one or more agents is a histone deacetylase inhibitor, which is optionally selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745.

7. The composition according to claim 2, wherein the inactivated tumor cell expresses and secretes one or more cytokines selected from the group consisting of GM-CSF, CCL20, CCL3, IL-12p70 and FLT-3 ligand.

8. The composition according to claim 2, wherein the inactivated tumor cell expresses and secretes a gp96-Ig fusion protein.

9. A method for treating an individual suffering from cancer, comprising:
administering to the individual in need thereof an effective amount of the compound according to claim 1.

10. The method according to claim 9, wherein the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a Merkel-cell carcinoma, a lymphoma and a multiple myeloma.

11. The method according to claim 9, wherein the administration is intra-tumoral, peri-tumoral, or directly into the tumor-draining lymph node(s).

12. The method according to claim 9, wherein the method further comprises administering one or more additional cancer therapies to the individual.

13. The method according to claim 12, wherein the one or more additional cancer therapies comprise (i) radiation therapy, surgery, a chemotherapy, or an immunotherapy; or (ii) administering one or more therapeutic antibodies to the individual; or (iii) administering one or more checkpoint inhibitors to the individual; or (iv) administering an inactivated tumor cell that expresses and secretes one or more cytokines or one or more heat shock proteins to the individual.

14. The method according to claim 13, wherein the immune checkpoint inhibitor(s) comprise an agent selected from the group consisting of an anti-PD-1 antibody, an anti-PD-L1 antibody, an anti-CTLA-4 antibody, an anti-TIM-3 antibody, an anti-BTLA antibody, an anti-Vista antibody, an anti-B7-H3 antibody, an anti-CD70 antibody, an anti-KIR antibody, and an anti-LAG-3 antibody.

15. The method according to claim 13, wherein the inactivated tumor cell expresses and secretes one or more cytokines selected from the group consisting of GM-CSF, CCL20, CCL3, IL-12p70, and FLT-3 ligand.

16. The method according to claim 13, wherein the inactivated tumor cell expresses and secretes a gp96-Ig fusion protein.

17. The method according to claim 12, wherein the one or more additional cancer therapies comprises administering a histone deacetylase inhibitor to the individual, wherein the histone deacetylase inhibitor is selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745.

* * * * *